United States Patent
Min et al.

(10) Patent No.: US 12,065,692 B2
(45) Date of Patent: Aug. 20, 2024

(54) OPTICAL SUPER-MULTIPLEXING BY POLYYNES

(71) Applicant: The Trustees of Columbia University in the City of New York, New York, NY (US)

(72) Inventors: Wei Min, Fort Lee, NJ (US); Fanghao Hu, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 467 days.

(21) Appl. No.: 16/624,682

(22) PCT Filed: Aug. 3, 2018

(86) PCT No.: PCT/US2018/045271
§ 371 (c)(1),
(2) Date: Dec. 19, 2019

(87) PCT Pub. No.: WO2019/028430
PCT Pub. Date: Feb. 7, 2019

(65) Prior Publication Data
US 2020/0199657 A1 Jun. 25, 2020

Related U.S. Application Data

(60) Provisional application No. 62/616,624, filed on Jan. 12, 2018, provisional application No. 62/540,953, filed on Aug. 3, 2017.

(51) Int. Cl.
| | |
|---|---|
| G01N 21/65 | (2006.01) |
| C12Q 1/6816 | (2018.01) |
| C12Q 1/6827 | (2018.01) |
| C12Q 1/6834 | (2018.01) |
| C12Q 1/686 | (2018.01) |
| B82Y 15/00 | (2011.01) |
| B82Y 30/00 | (2011.01) |
| H04Q 11/00 | (2006.01) |

(52) U.S. Cl.
CPC ......... *C12Q 1/6816* (2013.01); *C12Q 1/6827* (2013.01); *C12Q 1/6834* (2013.01); *C12Q 1/686* (2013.01); *G01N 21/65* (2013.01); *B82Y 15/00* (2013.01); *B82Y 30/00* (2013.01); *C12Q 2565/632* (2013.01); *H04Q 11/0005* (2013.01)

(58) Field of Classification Search
None
See application file for complete search history.

(56) References Cited

U.S. PATENT DOCUMENTS

| | | |
|---|---|---|
| 8,227,590 B2 | 7/2012 | Ranga et al. |
| 2003/0104395 A1 | 6/2003 | McLaughlin et al. |
| 2004/0058058 A1 | 3/2004 | Shchegolikhin et al. |
| 2006/0228733 A1 | 10/2006 | Pierce et al. |
| 2009/0136594 A1 | 5/2009 | McLeroy et al. |
| 2009/0186343 A1 | 7/2009 | Wang et al. |
| 2010/0284917 A1 | 11/2010 | Kustner et al. |
| 2015/0309062 A1 | 10/2015 | Covey et al. |
| 2016/0243261 A1 | 8/2016 | Min et al. |
| 2017/0089823 A1 | 3/2017 | Wagner et al. |
| 2019/0336940 A1* | 11/2019 | Kevlahan ........... B01J 20/28004 |

OTHER PUBLICATIONS

Tykwinski (Synthesis 14:1915-22) (Year: 2012).*
Armitage et al (1954 Journal of the Chemical Society pp. 147-154) (Year: 1954).*
Brady et al (JACS 119:775-88) (Year: 1997).*
Chalifoux et al (Nature Chemistry 2:967-71) (Year: 2010).*
Chalifoux et al (Nature Chemistry 2:967-71 supplemental information) (Year: 2010).*
Lee et al (Tet. Lett. 43:3863-6) (Year: 2002).*
Das et al. "Changes in the electronic structure and properties of graphene induced by molecular charge-transfer," Chem Comm., vol. 41, pp. 5155-5157, Nov. 7, 2008.
Zhang et al. "Stimulated Raman scattering flow cytometry for label-free single-particle analysis," Optica, vol. 4, pp. 103-109, Jan. 11, 2017.
Gracie et al. "Simultaneous detection and quantification of three bacterial meningitis pathogens by SERS," Chem. Sci., vol. 5, pp. 1030-1040, Dec. 20, 2013.
Wel et al. "Sjuper-multiplex vibrational imaging." Nature, vol. 544, pp. 465-47, Apr. 27, 2017.
Watson et al. "A Flow Cytometer for the Measurement of Raman Spectra," Cytometry Part A, vol. 73a, pp. 119-128, Jan. 11, 2008.
MacLaughlin, C.M. "Surface-enhanced raman scattering nanoparticles as optical labels for imaging cell surface proteins," Thesis, Univ of Toronto, Jul. 14, 2014.
Chol et al. "Immuno-Hybridization chain reaction for enhancing detection of individual cytokine-secreting human peripheral mononuclear cells," Anal Chem., vol. 83, pp. 6890-6895, Sep. 1, 2011.
International Search Report for International Patent Application No. PCT/US2018/045271 mailed on Oct. 30, 2018.
International Written Opinion for International Patent Application No. PCT/US2018/045271 mailed on Oct. 30, 2018.
Dean, K.M. et la., Advances in fluorescence labeling strategies for dynamic cellular imaging. Nat. Chem. Biol. 10, 512-523 (2014).
Valm, A.M. et al. Applying systems-level spectral imaging and analysis to reveal the organelle interactome. Nature 546, 162-167 (2017).
Niehörster, T. et al. Multi-target spectrally resolved fluorescence lifetime imaging microscopy. Nat. Methods 13 , 257-262 (2016).

(Continued)

*Primary Examiner* — Christopher M Gross

(74) *Attorney, Agent, or Firm* — Amster, Rothstein & Ebenstein LLP

(57) ABSTRACT

A method for optical super-multiplexing using polyynes to provide enhanced images from stimulated Raman microscopy is disclosed. In some exemplary embodiments, the polyynes are organelle-targeted or spectral barcoded. Imaging can be enhanced by using the polyynes to image whole live cells or specific organelles within live cells. The polyynes can also be used in optical data storage (i.e., encoding) and identification (i.e., decoding) applications.

12 Claims, 16 Drawing Sheets

(56) References Cited

OTHER PUBLICATIONS

Krutzik, P.O. et al., Fluorescent cell barcoding in flow cytometry allows high-throughput drug screening and signaling profiling. Nat. Methods 3, 361-368 (2006).
Lu, J. et al. MicroRNA expression profiles classify human cancers. Nature 435, 834-838 (2005).
Li, Y. et al., Multiplexed detection of pathogen DNA with DNA-based fluorescence nanobarcodes. Nat. Biotechnol. 23, 885-889 (2005).
Leng, Y. et al., Suspension arrays based on nanoparticle-encoded microspheres for high-throughput multiplexed detection. Chem. Soc. Rev. 44, 5552-5595 (2015).
Zijlstra, P. et al., Five-dimensional optical recording mediated by surface plasmons in gold nanorods. Nature 45 9, 410-413 (2009).
Lu, Y. et al. Tunable lifetime multiplexing using luminescent nanocrystals. Nat. Photonics 8, 32-36 (2014).
Nguyen, H.Q. et al. Programmable microfluidic synthesis of over one thousand uniquely identifiable spectral codes. Adv. Opt. Mater. 5, 1600548 (2017).
Fournier-Bidoz, S. et al. Facile and rapid one-step mass preparation of quantum-dot barcodes. Angew. Chem. Int. Ed. Engl. 47, 5577-5581 (2008).
Han, M. et al., Quantum-dot-tagged microbeads for multiplexed optical coding of biomolecules. Nat. Biotechnol. 19, 631-635 (2001).
Cao, Y.C. et al., Nanoparticles with Raman spectroscopic fingerprints for DNA and RNA detection. Science 297, 1536-1540 (2002).
Jin, R. et al., Glass-bead-based parallel detection of DNA using composite Raman labels. Small 2, 375-380 (2006).
Casari, C.S. et al., Polyynes: 1-D systems with tunable properties. Nanoscale 8, 4414-4435 (2016).
Hirsch, A. The era of carbon allotropes. Nat. Mater. 9, 868-871 (2010).
Liu, M. et al., Carbyne from first principles: chain of C atoms, a nanorod or a nanorope. ACS Nano 7, 10075-10082 (2013).
Chalifoux, W.A. et al., Synthesis of polyynes to model the sp-carbon allotrope carbyne. Nat. Chem. 2, 967-971 (2010).
Luu, T. et al. Synthesis, structure, and nonlinear optical properties of diarylpolyynes. Org. Lett. 7, 51-54 (2005).
Milani, A., et al., Carbon nanowires: phonon and pi-electron confinement. Phys. Rev. B 74, 153418 (2006).
Lucotti, A. et al. Absolute Raman intensity measurements and determination of the vibrational second hyperpolarizability of adamantyl endcapped polyynes. J. Raman Spectrosc. 43, 1293-1298 (2012).
Yamakoshi, H. et al. Alkyne-tag Raman imaging for visualization of mobile small molecules in live cells. J. Am. Chem. Soc. 134, 20681-20689 (2012).
Chen, Z. et al. Multicolor live-cell chemical imaging by isotopically edited alkyne vibrational palette. J. Am. Chem. Soc. 136, 8027-8033 (2014).
Liu, Z. et al. Multiplexed multicolor Raman imaging of live cells with isotopically modified single walled carbon nanotubes. J. Am. Chem. Soc. 13 0, 13540-13541 (2008).
Lucotti, A. et al. Evidence for solution-state nonlinearity of sp-carbon chains based on IR and Raman spectroscopy: violation of mutual exclusion. J. Am. Chem. Soc. 131, 4239-4244 (2009).
Freudiger, C.W. et al. Label-free biomedical imaging with high sensitivity by stimulated Raman scattering microscopy. Science 322, 1857-1861 (2008).
Wei, L. et al. Live-cell imaging of alkyne-tagged small biomolecules by stimulated Raman scattering. Nat. Methods 11, 410-412 (2014).
Yamakoshi, H. et al. A sensitive and specific Raman probe based on bisarylbutadiyne for live cell imaging of mitochondria. Bloorg. Med. Chem. Lett. 25, 664-667 (2015).
Wilson, R. et al., Encoded microcarriers for high-throughput multiplexed detection. Angew. Chem. Int. Ed. Engl. 45, 6104-6117 (2006).
Lee, J.H. et al., Dye-labeled polystyrene latex microspheres prepared via a combined swelling-diffusion technique. J. Colloid Interface Sci. 363, 137-144 (2011).
Humar, M. et al., Intracellular microlasers. Nat. Photonics 9, 572-576 (2015).
Agarwal, N.R. et al. Structure and chain polarization of long polyynes investigated with infrared and Raman spectroscopy. J. Raman Spectrosc. 44, 1398-1410 (2013).
Ozeki, Y. et al. High-speed molecular spectral imaging of tissue with stimulated Raman scattering. Nat. Photonics 6, 845-851 (2012).
Liao, C.S. et al. Microsecond scale vibrational spectroscopic imaging by multiplex stimulated Raman scattering microscopy. Light Sci. Appl. 4, e265 (2015).
Choi, HM et al., Next-generation in situ hybridization chain reaction: higher gain, lower cost, greater durability. ACS Nano. 27, 4284-94 (2014).
Lin,R. et al., A hybridization-chain-reaction-based method for amplifying immunosignals. Nat Methods. 15, 275-278 (2018).
Supplementary Extended European Search Report for European Patent Application No. 18 842 004.6 mailed on Mar. 26, 2021.
Lampkowski Jessica S. et al., "Preparation of asyrrmetrical polyynes by a solid-supported Glaser-Hay reaction", Organic & Biomolecular Chemistry, vol. 13, No. 2, Jan. 1, 2015, pp. 424-427.
Lee Seonwoo et al: "Solid-Phase Library Synthesis of Polyynes Similar to Natural Products", Angewandte Chemie International Edition, vol. 46, No. 44, Nov. 12, 2007, pp. 8422-8425.
Tang Yuchen et al: "Single-Bead Quantification of Peptide Loading Distribution for One-Bead One-Compound Library Synthesis Using Confocal Raman Spectroscopy", Analytical Chemistry, vol. 89, No. 13, Jun. 8, 2017, pp. 7000-7008.
Hu Fanghao et al: "Supermultiplexed optical imaging and barcoding with engineered polyynes", Nature Methods, vol. 15, No. 3, Mar. 1, 2018, pp. 194-200.
Communication pursuant to Article 94(3) EPC mailed on Aug. 12, 2022 for European Patent Application No. 18 842 004.6-1118.

\* cited by examiner

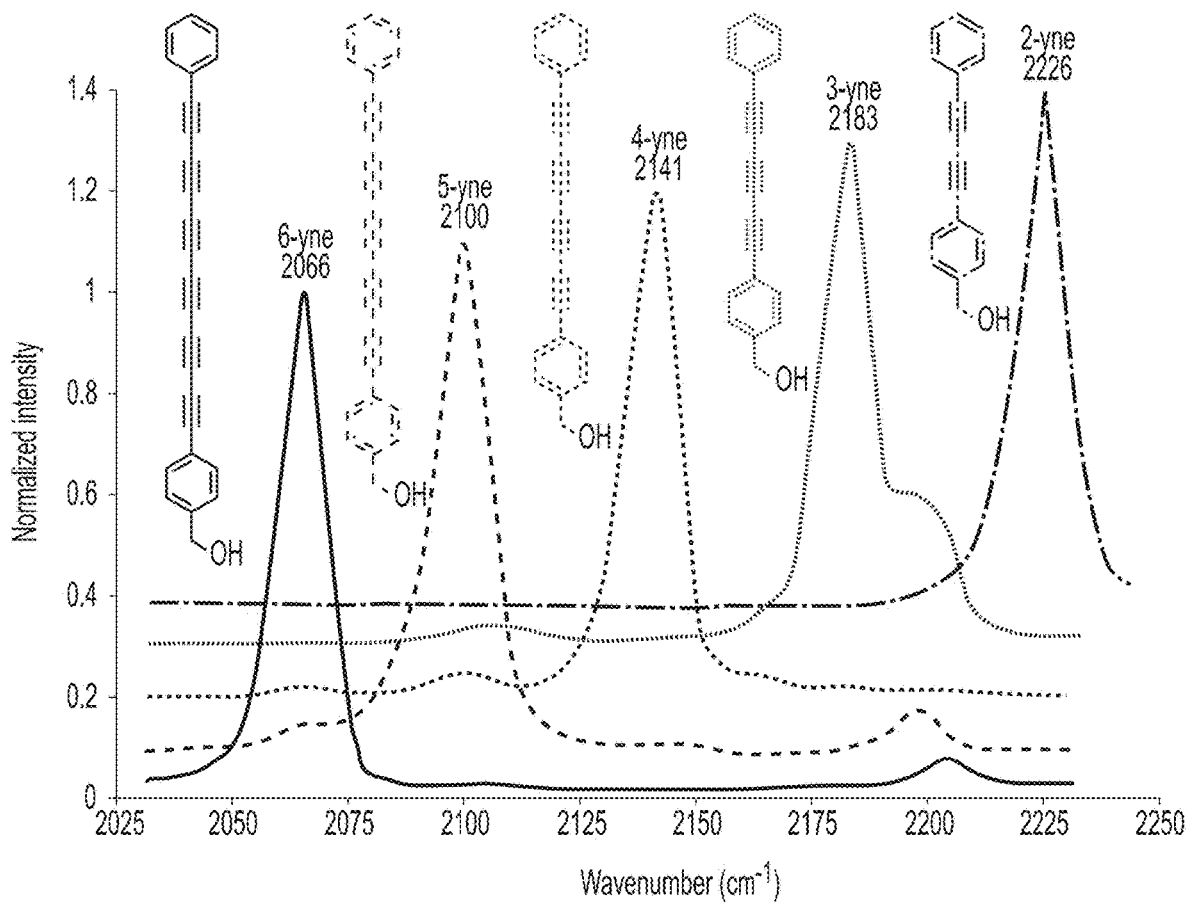

FIG. 1A

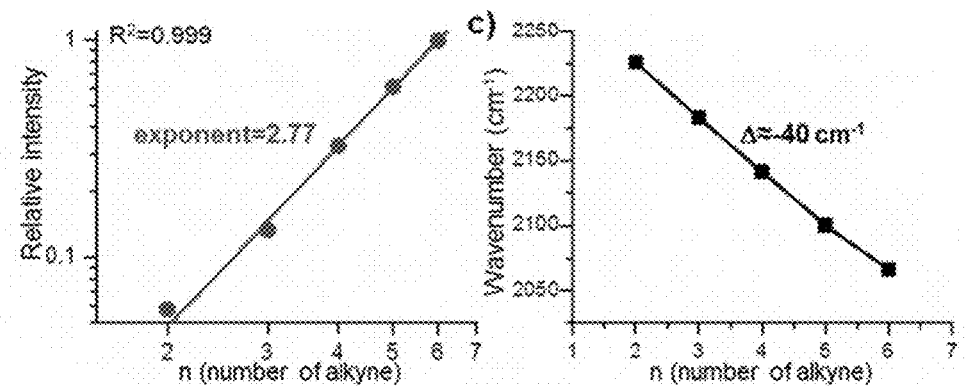

FIG. 1B

Figure 1. Length dependence of Raman vibration in phenyl-capped polyynes. (a) Normalized Raman spectra of polyynes from 2-yne to 6-yne. The spectra are vertically offset for clarity. (b) Raman intensity of polyynes increases superlinearly with conjugation length, following the power-law dependence in the double logarithmic plot. (c) Raman frequency of polyynes decreases almost linearly with increasing length, with an interval of ~40 $cm^{-1}$.

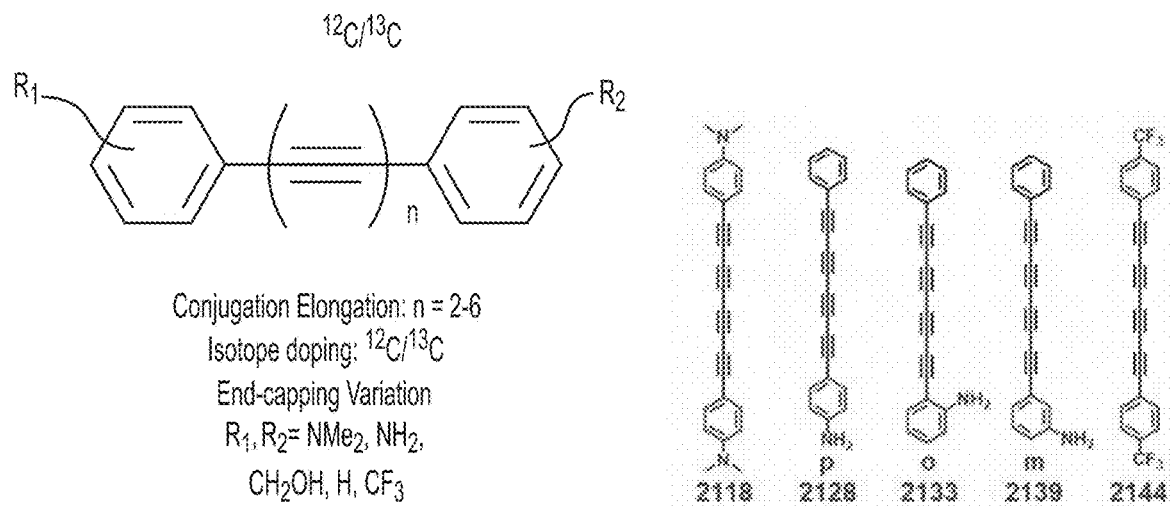

FIG. 2A

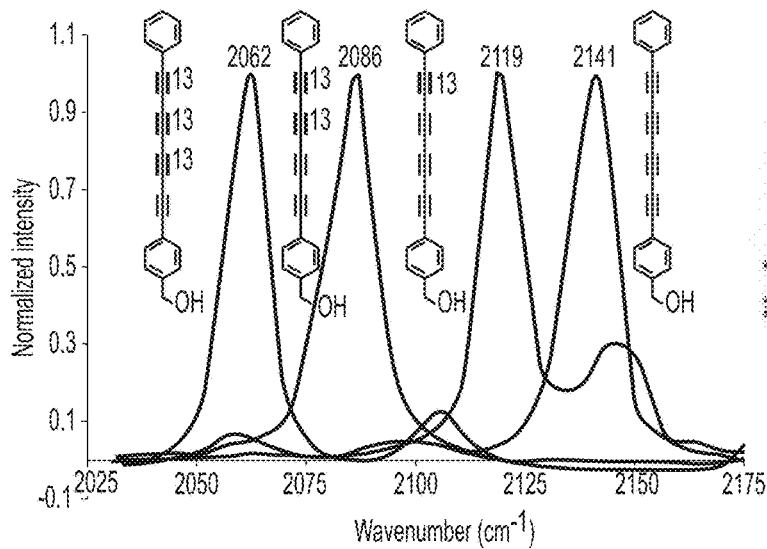

FIG. 2B

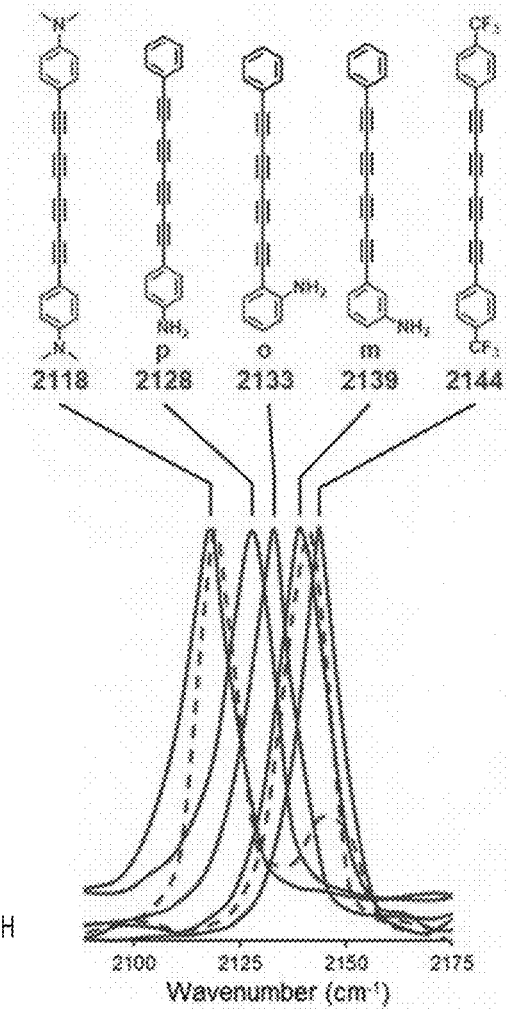

FIG. 2C

Figure 2. Raman frequency expansion of polyynes. (a) Frequency modulation on the unified polyyne scaffold by conjugation elongation, isotope doping and end-capping variations. (b) Frequency coarse-tuning in polyynes with $^{13}C$ isotope labeling (in red). (c) Frequency fine-tuning of polyynes with electron-donating and –withdrawing groups (in blue), which is complementary to the coarse-tuning range (red dash line).

Super-multiplexed carbon-atom wires. (a) Chemical structures of 20 carbon-atom wires with distinct Raman frequencies, which are termed as Carbon rainbow (Carbow). (b) Highly resolved Raman peaks of Carbow in the bioorthogonal spectral window.

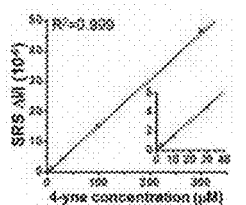 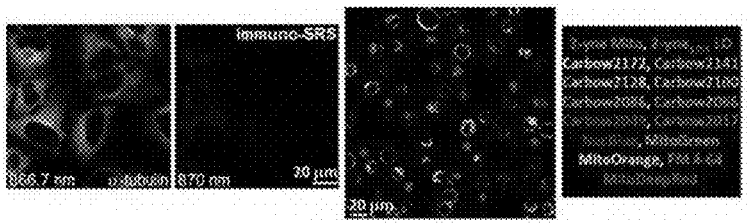

FIG. 4A     FIG. 4B     FIG. 4C

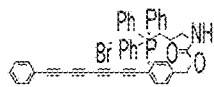  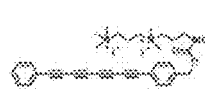 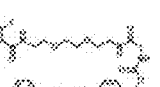 

FIG. 4D    FIG. 4E    FIG. 4F    FIG. 4G    FIG. 4H

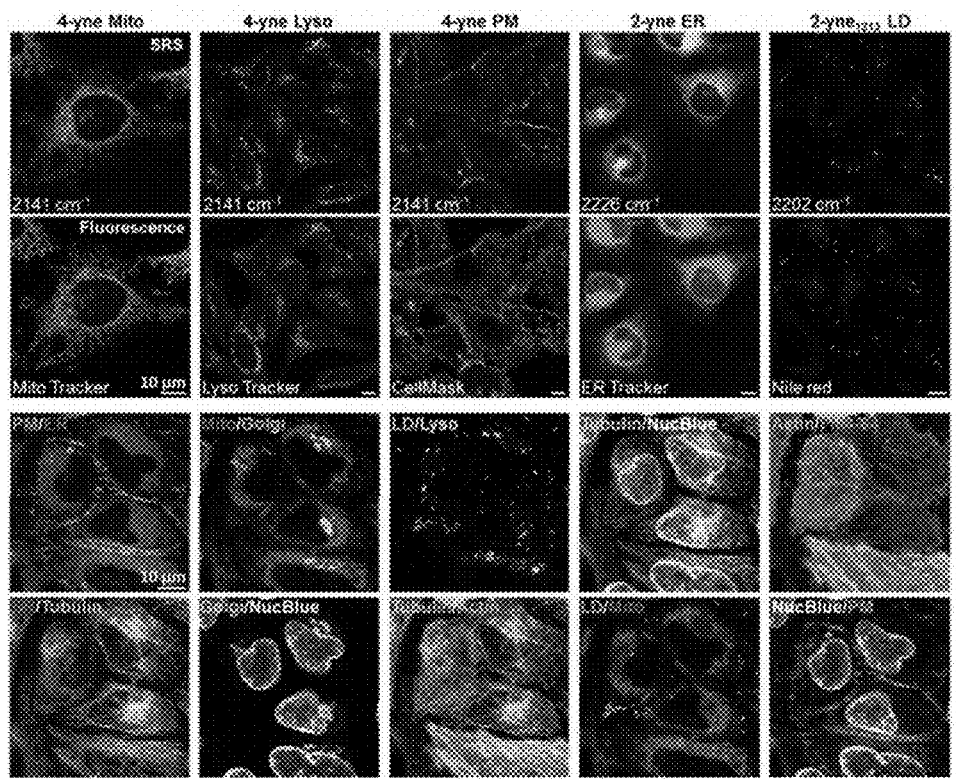

FIG. 4I

Figure 4. Super-multiplexed optical imaging with carbon-atom wires. (a) Linear concentration dependence of 4-yne with sub-µM SRS detection sensitivity. (b) Immuno-staining and imaging of α-tubulin in fixed cells with 4-yne conjugated antibody. (c) 15-color tandem fluorescence-SRS imaging of live cells with super-multiplexed carbon-atom wires. (d-h) Chemical structures of five organelle-targeted probes based on carbon-atom wires for live-cell imaging, including mitochondria Mito (d), lysosome Lyso (e), plasma membrane PM (f), endoplasmic reticulum ER (g) and lipid droplet LD (h). (i) 10-color optical imaging of plasma membrane, ER, Golgi, mitochondria, lipid droplets, lysosome, nucleus, tubulin and actin in living cells. Overlay of two species are shown in each image.

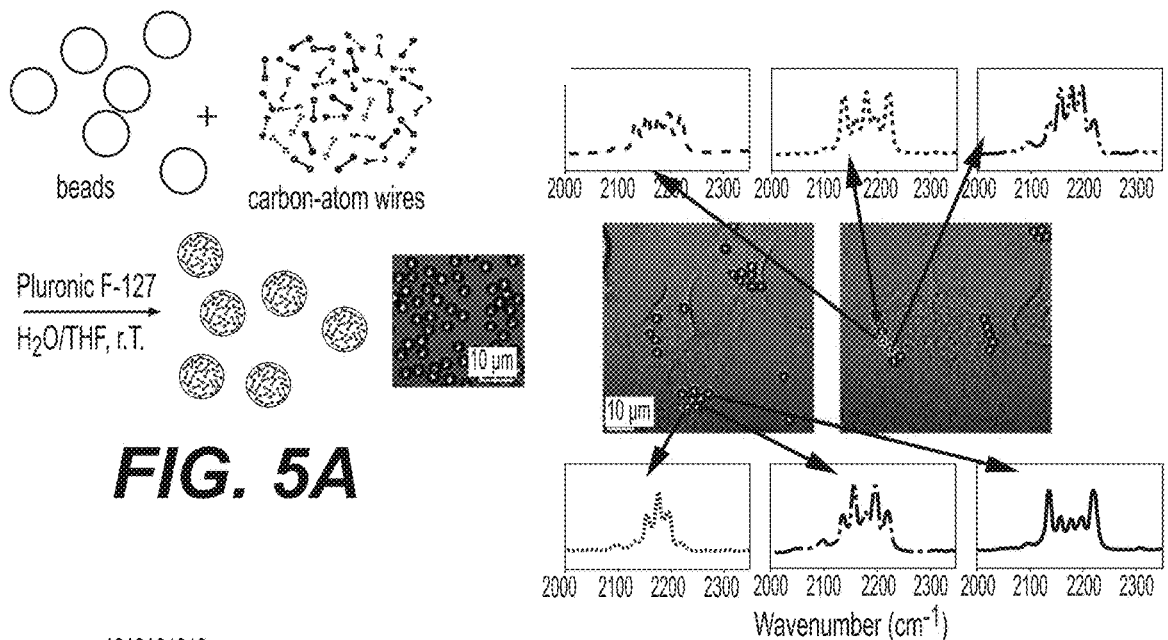
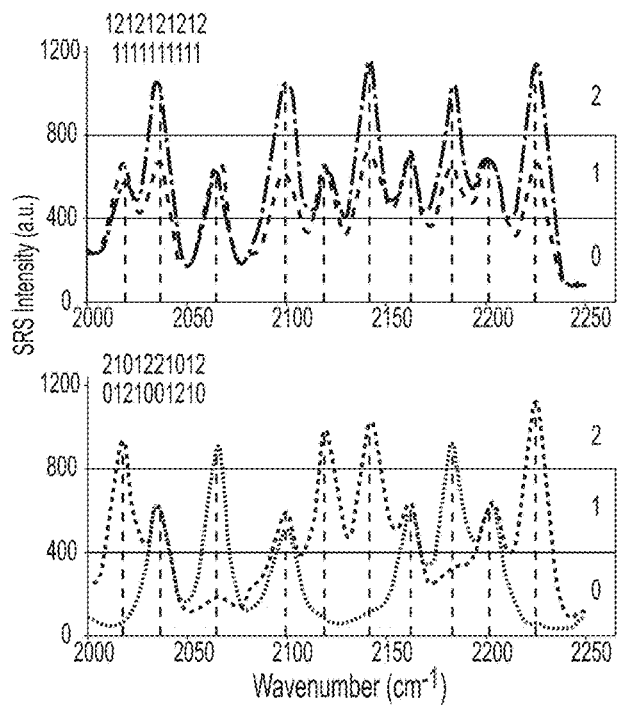
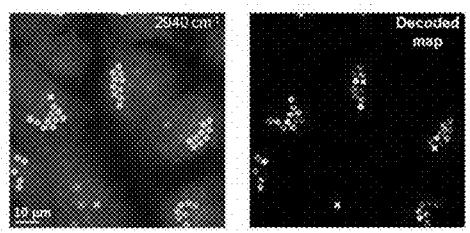

Figure 5. Super-multiplexed optical barcoding with carbon-atom wires. (a) Polymer beads are readily encoded by combinatory loading of carbon-atom wires through physical absorption. Inset shows the bright-field image of barcoded polystyrene beads. (b) Spectral barcoding of carbonatom wires at 10 frequencies and 3 intensities with SRS readout, which can obtain $3^{10}=59049$ distinct barcodes. (c) Cells are labeled with multiple encoded beads, as shown by the bright-field images. The barcode information is well preserved in live cells with clear readout by spontaneous Raman measurement. (d) Rapid decoding and spatial visualization of bead identities with SRS microscopy. Left: 2940 $cm^{-1}$ image of unidentified beads inside living cells; Right: decoded beads in the whole field of view by hyperspectral imaging at characteristic frequencies). The color of each bead in the decoded map corresponds to the spectral barcode in (c).

Figure 6. UV-Vis absorption spectra of polyynes from 2-yne to 6-yne. The spectra are vertically offset for clarity. The absorption maxima redshift ~35 nm with every additional triple bond. Three sets of peaks are clearly observed at the highest wavelengths as vibrational fine structures, indicating strong vibronic coupling.

Figure 7. Frequency exploration of polyynes through conjugation elongation, end-capping variations and isotope doping. 40 structures are synthesized and shown with Raman frequencies (in cm$^{-1}$) measured in DMSO.

Figure 8. 15-color imaging of live cells with super-multiplexed carbon-atom wires. Individual channel of 5 fluorescent dyes and 10 carbon-atom wires with well-resolved frequencies are shown with little crosstalk. Simple unmixing is performed by subtracting the adjacent channel, without the need of complicated matrix unmixing.

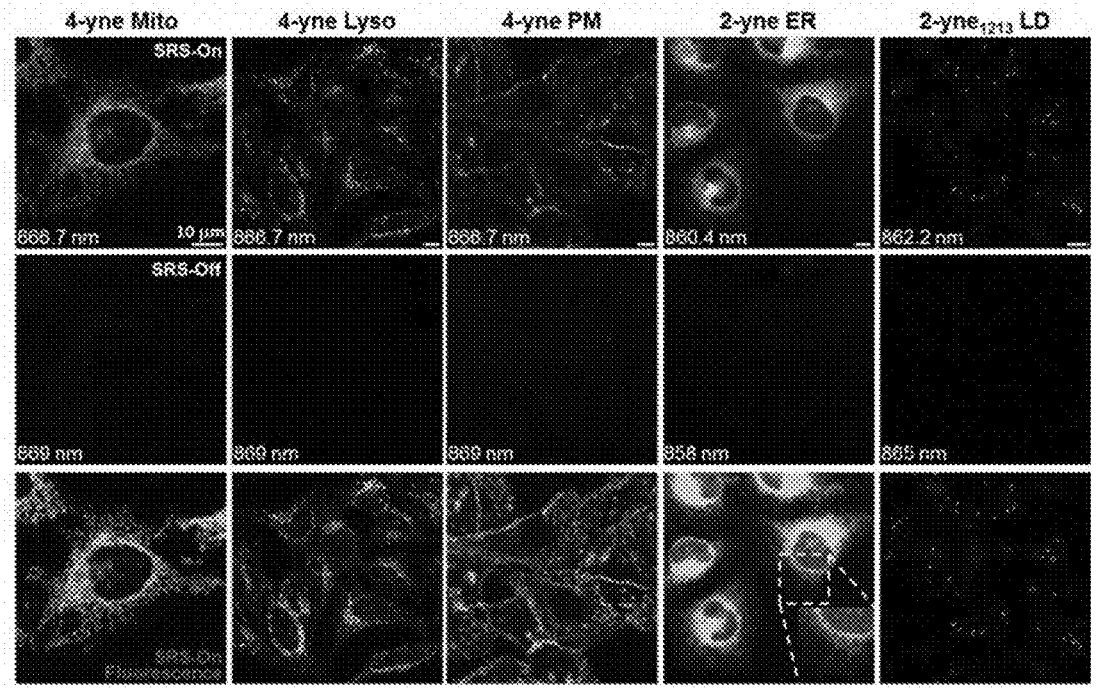

Figure 9. Live-cell SRS imaging of organelle-targeted carbon-atom wires and co-localization with fluorescent organelle markers. Characteristic labeling patterns are shown for each organelle with negligible crosstalk at 3 nm away, which displays the sharp vibrational feature of carbon-atom wires and is far beyond the spectral resolution of fluorescent dyes. High co-localizations are also observed between organelle-targeted carbon-atom wires with commercial fluorescent markers.

*FIG. 9*

Figure 10. Excellent photostability of carbon-atom wires in live cell imaging. HeLa cells are incubated with 2 μM 4-yne Lyso for 1 h, 4 μM 4-yne Mito for 1 h or 10 μM 2-yne$_{1213}$ LD for overnight. Cells are continuously imaged for 100 frames with nearly identical intensity, and the intensity trace shows minimal decay (<2%).

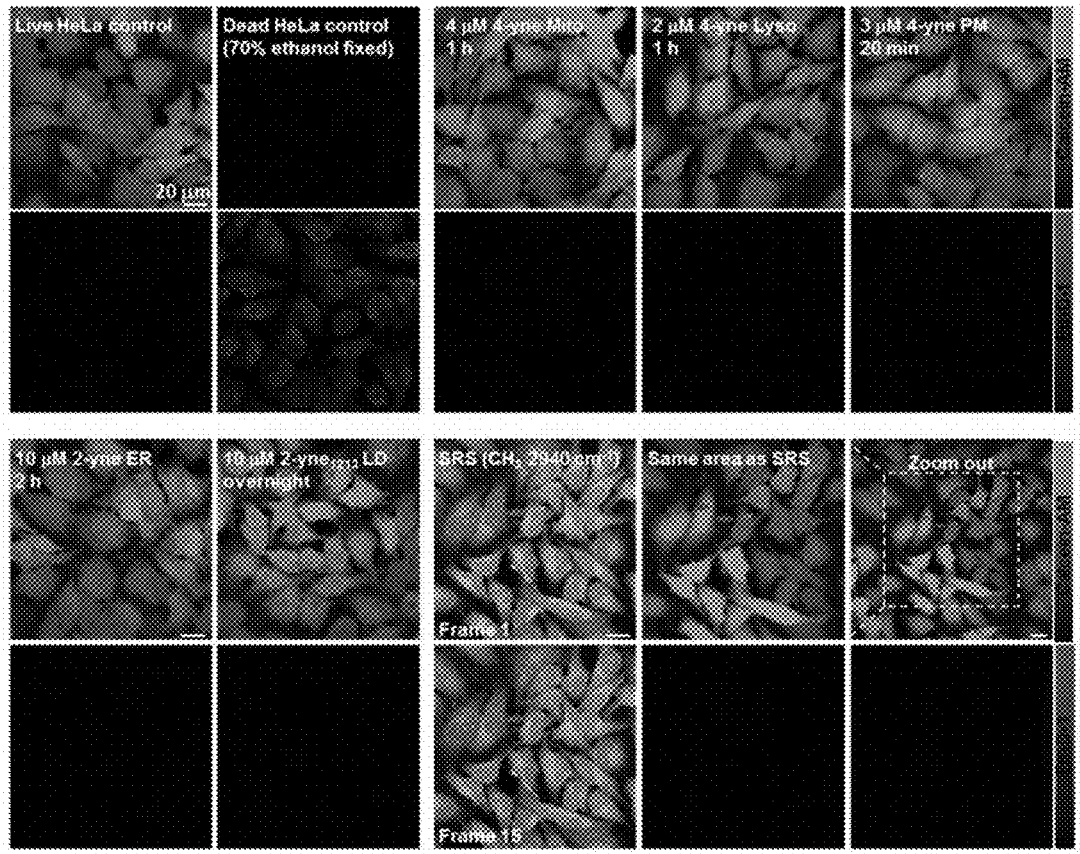

Figure 11. Minimal cytotoxicity of carbon-atom wires in live cells and phototoxicity of SRS lasers. Live and dead HeLa cell standards are verified with Live/Dead viability kit. All five organelle-targeted carbon-atom wires exhibit little cytotoxicity in live cells, as shown by two-color imaging of Calcein-AM (green, live-cell marker) and EthD-1 (red, dead-cell marker). Also, Minimal photo-toxicity is observed in cells with SRS illumination. After 15 frames of continuous SRS imaging at 2940 $cm^{-1}$ (protein $CH_3$) using the same laser power and dwell time in multiplexed live-cell imaging, the same region of cells show no observable cell death in the viability assays, compared to surrounding cells without SRS laser exposure.

FIG. 11

Figure 12. 10 representative spectral barcodes in polystyrene beads by confocal Raman microscope. 5 carbon-atom wires (Carbow2141, Carbow2160, Carbow2183, Carbow2202 and Carbow2226) that are compatible with 532 nm excitation are used in spectral encoding for spontaneous Raman measurement (Table S2).

Figure 13.Hyperspectral SRS imaging of encoded beads in live cells. Bright-field image shows the spatial distribution of unidentified beads in cells. Consecutive SRS imaging at characteristic frequencies of carbon-atom wires allows rapid decoding and visualization of bead identity in space.

Figure 14. Frequency encryption with carbon-atom wires for identity security and anti-counterfeiting. Microscopic Columbia logos on PDMS look similar in the bright-field images and hyperspectral SRS images reveal the true identity of both logos in the frequency domain. For example, Columbia in red is counterfeit and Columbia in blue is authentic.

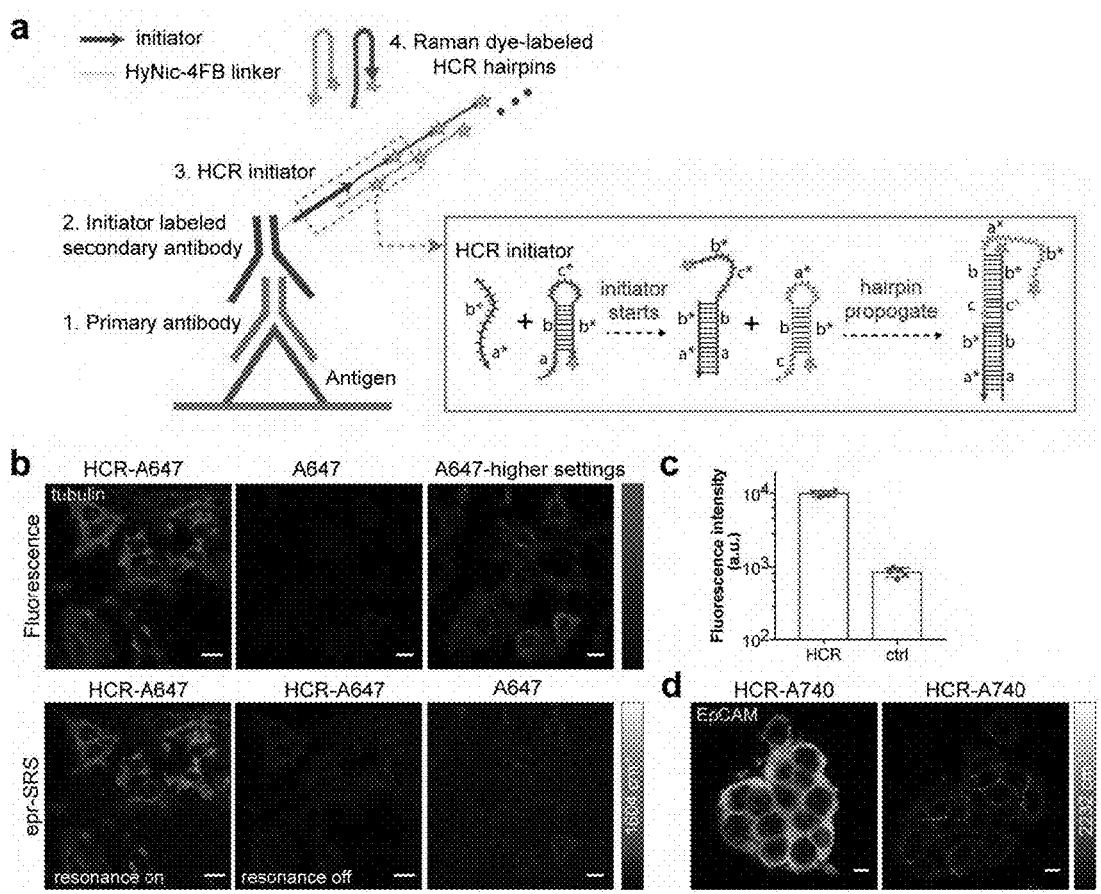

Figure 16. Hybridization Chain Reaction (HCR) amplification can greatly enhance SRS signal in protein imaging.

(a) HCR scheme for protein signal amplification. Interested targets are labeled through normal immunostaining but using a DNA initiator-conjugated secondary antibody. The initiators will start a chain reaction in which two Raman dye-labeled hairpins assemble sequentially into a long double-stranded amplification polymer.
(b) Amplification quantitation on rabbit α-tubulin using Alexa Fluo 647 (A647). Images for HeLa cells immunostained with normal A647-conjugated anti rabbit antibody and HCRamplified with A647-conjugated HCR amplifiers. The top row are detected by fluorescence and the bottom row are detected by SRS. "Higher settings" indicates 10- fold higher laser power. (c) The amplification factor for HCR-A647 vs normal A647 is more than 10-fold. Error bars represent the s.e.m between different field-of-views. (d) HCR method can greatly enhance SRS signal on a low abundance transmembrane tumor marker EpCAM.
Scale bars, 20 μm.

*FIG. 16*

OPTICAL SUPER-MULTIPLEXING BY POLYYNES

CROSS REFERENCE TO RELATED APPLICATION(S)

The application relates to and claims priority from International Patent Application No. PCT/US2018/045271 filed Aug. 3, 2018 which was published as International Publication No. WO 2019/028430 on Feb. 7, 2019 and claims the benefit and priority from U.S. Provisional Patent Application Ser. No. 62/540,953 filed on Aug. 3, 2017 and U.S. Provisional Patent Application Ser. No. 62/616,624 filed on Jan. 12, 2018, the entire disclosures of which are incorporated herein by reference.

STATEMENT REGARDING FEDERALLY SPONSORED RESEARCH

This invention was made with government support under Grant No. EB020892 awarded by the National Institutes of Health. The government has certain rights in the invention.

FIELD OF THE DISCLOSURE

The present disclosure generally relates to optical super-multiplexing applications in live cell imaging using polyynes, as well as libraries of polyynes useful in optical super-multiplexing applications.

BACKGROUND INFORMATION

The current big data era has created increasing demands for rapid accumulation of massive information, where high-throughput multiplexed detection of large number of targets is highly desirable. Optical detection is one of the most efficient methods for non-invasive information readout at far field. As a result, many optical multiplexing techniques have been developed, such as multiplexed microscopy and barcoding. These techniques are primarily based on fluorescence of organic dyes, fluorescent proteins or inorganic luminescent nanomaterials including quantum dots, rare earth nanoparticles and up-conversion nanocrystals.

However, due to the broad linewidth and significant overlap in fluorescence spectra, the number of resolvable features for fluorescence detection is limited. Thus, multiplexed fluorescence microscopy can achieve fewer than 10-color simultaneous imaging, requiring the use of complicated optical setup and spectral un-mixing, and less than 2000 optical barcodes can be created even with combinatory spectral encoding, due to the unavoidable crosstalk and self-quenching issues.

Multiplexing refers to high-throughput simultaneous measurement of a large number of distinctive species. Modern life science and technology has increasing demands for multiplexing techniques, such as simultaneous visualization of multiple components in a protein complex or multiple organelles in a single cell with molecular imaging probes, high-throughput detection of antigens or small molecules for cell sorting, medical diagnostics and drug discovery with bead-based suspension assays and high-density information storage and encryption for identity security and anti-counterfeiting. To achieve multiplexing in a complex system, it requires a matrix of distinguishable codes that can be readily applied and identified, and optical codes are one of the most popular methods for non-invasive and non-destructive readout at far field.

Many luminescent materials have been developed over the last several decades for optical multiplexing. For example, organic dyes and fluorescent proteins are widely applied for multicolor imaging in biological systems and inorganic luminescent materials including quantum dots, metal nanostructures, rare earth nanoparticles, and up-conversion nanocrystals are commonly used in spectral barcoding for multiplexed identification, which is key to high-throughput screening and data security applications. However, because of the broad linewidth and significant spectral overlap, the number of resolvable features in current luminescent materials is limited. Less than 7 colors can be practically imaged in live cells by fluorescence multiplexing microscopy requiring multiple lasers, filters and detectors as well as complicated spectral unmixing and color compensation. And fewer than 2000 spectral barcodes can be reached with combinatory encoding due to the unavoidable crosstalk in organic dyes, FRET energy transfer between different quantum dots limited number of suitable features and complicated decoding procedures with rare-earth nanocrystals and metal nanoparticles. Therefore, new optical materials that can overcome the spectral limitation and break the longstanding "multiplexing ceiling" are greatly needed.

Polyynes are linear chains of sp-hybridized carbon atoms with alternating single and triple bonds, which are also known as carbon-atom wires. Compared to other well-known carbon materials such as sp3-hybridized diamonds and sp2-hybridized low-dimension systems including 2-D graphene, quasi 1-D carbon nanotube, and quasi 0-D fullerene, sp-hybridized carbon-atom wire is one of the least studied carbon allotropes with a true 1-D structure. Difficulty in accessing stable polyynes has made them largely unexplored. In theory, polyynes should have many appealing properties, such as super-high thermal conductivity, strong mechanical strength, and greater stiffness than any known materials. Over the last decade, significant progress has been made toward the chemical synthesis of polyynes with well-defined composition and structure, and an isolable polyyne with 44 contiguous carbon atoms has been synthesized using bulky end-capping groups to sterically stabilize the polyyne chain.

Thus, it may be beneficial to provide exemplary optical super-multiplexing by polyynes, which can overcome at least some of the deficiencies described herein above.

SUMMARY OF EXEMPLARY EMBODIMENTS

Optical multiplexing impacts widely in life science, medicine, and information technology. Current multiplexing techniques are restricted to a limited number due to the spectral overlap and significant crosstalk in luminescent materials.

In one exemplary embodiment, the present disclosure relates to new polyyne-based materials (referred to herein as polyynes), and the exploitation of their optical properties for super-multiplexed detection. In one aspect of such exemplary embodiment, the polyynes are present in libraries which include between 2 and 200 members, more typically, between 10 and 100 members, and still more typically, between 4 and 50 members. In another exemplary embodiment, the present disclosure relates to the use of the polyynes described herein in optical super-multiplexing by Raman scattering, such as stimulated Raman scattering.

In one aspect of such exemplary embodiment, the polyynes have the structure:

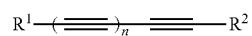

wherein n is an integer from 1 to 19, typically from 2 to 19, and still more typically, from 3 to 5, $R^1$ and $R^2$ are, independently, aryl, $C_{1-20}$ alkyl, trialkylsilyl, aryldialkylsilyl, diarylalkyl silyl, metal, a metal complex, aryl-$C_{1-20}$ alkyl, $C_{1-20}$ alkyl-aryl, heteroaryl, heteroaryl-$C_{1-20}$alkyl, or $C_{1-20}$ alkyl-heteroaryl, wherein each of these groups can optionally be substituted with one or more substituents, one or more of the hydrogens in these groups can be deuterated, and one or more of the carbons in the alkyne moieties can be $^{13}C$ labeled, and wherein the substituents on one or more of the aryl, $C_{1-20}$ alkyl, aryl-$C_{1-20}$ alkyl, $C_{1-20}$ alkyl-aryl, heteroaryl, heteroaryl-$C_{1-20}$ alkyl, or $C_{1-20}$ alkyl-heteroaryl groups include functional groups which can be conjugated to metal nanostructures, antibodies, peptides, nucleic acids, lipids, or carbohydrates; electron withdrawing or electron donating groups which can shift the Raman spectrum of the polyynes relative to unsubstituted groups; groups which target specific organelles, cellular compartments, fluorescent labels (which can allow the polyynes to be detected using both fluorescence and Raman spectroscopy), biotin or streptavidin.

In another aspect of such exemplary embodiment, the polyynes have well-resolved Raman peaks with less than 10% cross-talk.

Representative polyynes include, but are not limited to, Carbow2172, Carbow2141, Carbow 2128, Carbow2100, Carbow2086, Carbow2066, Carbow2049, and Carbow2017, as described in the working examples.

As shown in the working examples, a small library of polyynes has been demonstrated to show 20 distinct frequencies, with single strong peak and minimal crosstalk. These polyynes were prepared using rational engineering of conjugation length, isotope doping, and substitution variations. Using these polyynes, up to 30-channel parallel optical detections can be achieved in tandem with fluorescence. With super-multiplexed polyynes, 15-color live-cell imaging can be demonstrated without the need of complicated un-mixing and 10-color optical imaging of organelles can be achieved in a single living cell with excellent specificity, sensitivity, and photostability and live-cell compatibility.

In another exemplary embodiment, the present disclosure relates to materials conjugated to the polyynes described herein. Representative materials to which the polyynes can be conjugated include, but are not limited to, nanoparticles, including nanobeads, nanorods, nanostars and nanowires, such as metallic nanostructures and carbon nanotubes, microparticles, including microbeads, such as polystyrene microbeads, nanobodies, antibodies, antibody mimetics, including nanobodies, antibody mimetics and antibodies which specifically bind to stem cells, cancer cells, immune cells, neurons, glia, bacteria, fungi, and/or viruses, nucleic acids, including DNA, including genomic DNA and cDNA, RNA, such as siRNA, mRNA, tRNA, tmRNA, ncRNA, rRNA, shRNA, ribozymes, and the like, riboswitches, aptamers, primers, probes, and artificial nucleic acid analogues, such as peptide nucleic acids, morpholino- and locked nucleic acids, glycol nucleic acids, and threose nucleic acids.

In one aspect of such exemplary embodiment, the present disclosure relates to libraries of material-conjugated polyynes. Libraries which include polyynes which can target multiple organelles can be used to image organelles in cells. Libraries which include polyynes linked to antibodies, nanobodies, antibody mimetics, nucleic acids, and the like, which bind to stem cells, cancer cells, immune cells, neurons, glia, bacteria, viruses, and/or fungi can be used to identify the presence of antigens, receptors, genetic materials, and/or the types of, stem cells, cancer cells, immune cells, neurons, glia, bacteria, viruses, and/or fungi present in a biological sample. Certain antibodies, monobodies, nucleic acids, aptamers, and the like can also be used to determine the presence of cellular products such as cytokines, proteins, and other factors.

In another exemplary embodiment, the polyynes are used for optical data storage and identification using super-multiplexed spectral barcoding. A plurality, such as more than 50,000, distinct barcodes can be readily generated in micron-sized beads for high-throughput diagnostic assays, and higher numbers of optical IDs can be obtained for single cell tagging and mapping. Thus, this application greatly extends the current limit of optical multiplexing and facilitates multiplexed live-cell imaging, high-throughput medical diagnostics, and cell atlas in vivo.

In another exemplary embodiment, the polyynes are used to image cultured live cells. The methods involve culturing live cells, which can be derived from an in vitro tissue cell culture of interest, extracted from an in vivo subject of interest, seeding the cultured live cells in wells, and labelling each well with a single color of polyynes in culture media, wherein the polyynes comprise one or more colors. The labelled cultured live cells are then added to an imaging chamber for stimulated Raman microscopy, and the cells are imaged using stimulated Raman microscopy, wherein each cell is maintained with a single color during the imaging period.

In another exemplary embodiment, the polyynes are used to image organelles in cultured live cells. The methods involve culturing live cells, which can be derived from an in vitro tissue cell culture of interest or extracted from an in vivo subject of interest, incubating the cultured live cells with polyynes in culture media, wherein the polyynes each comprise a specific organelle-targeted probe, labelling the cultured live cells with the polyynes, and imaging the cells using stimulated Raman microscopy. In one aspect of such exemplary embodiment, the cultured live cells are seeded in a well before they are incubated and labelled with the polyynes, and then the cells are labelled with the polyynes, wherein the polyynes each comprise a specific organelle-targeted probe, which probes specifically target different organelles. Representative organelle-targeted probes include probes which target the plasma membrane, endoplasmic reticulum (ER), Golgi, mitochondria, lipid droplets, lysosome, nucleus, and tubulin in the cultured live cells.

In another exemplary embodiment, the polyynes are used in methods of live-cell tagging using spectral barcoded beads. The methods involve mixing polymeric microbeads, such as polystyrene beads, with spectral barcoded polyynes, binding the beads with the spectral barcoded polyynes to form barcoded beads, and culturing live cells, which can be derived from in vitro tissue cell culture of interest, or extracted from an in vivo subject of interest. The barcoded beads are incubated with the cultured live cells in culture media, which labels the cultured live cells with the barcoded beads. The cultured live cells can then be imaged using stimulated Raman microscopy, and the spectral barcodes of the barcoded beads in the whole field of view can be decoded based on hyperspectral SRS (Stimulated Raman scattering) images.

In another exemplary embodiment, the polyynes are used to identify a population of cancer cells using flow cytometry, or other methods for sorting/counting cells. The methods involve associating one or more polyynes (also referred to herein as "carbon atom wires") with live cells of a subject of interest, wherein the carbon atom wires are conjugated with antibodies that detect, and bind to, specific cell surface markers of the live cells, and further wherein the antibodies bind to cell surface markers of the live cells. The live cells are positioned in a focused flow stream of a flow cytometer; and illuminated within the focused flow stream of the flow cytometer with a predetermined wavelength of light. The cells are exposed to the illumination, and light is deflected as it comes into contact with the cells. The resulting scattered light from the live cells is detected in the frequency domain, and the Raman scattering spectrum is analyzed to identify individual groups of live cells. Cells that are not cancer cells are not linked to the carbon atom wire-conjugated antibodies, whereas cancer cells are linked to the carbon atom wire-conjugated antibodies. The cancer cells are detected based on the Raman spectra of scattered light produced by the carbon atom wires conjugated with antibodies.

The particular cell type can be detected based on the Raman spectra of scattered light, rather than the absorption, at a single wavelength. The scattering is not Rayleigh scattering, but rather, Raman scattering, which has different wavelengths compared to that of excitation light. By looking at the Raman spectrum, it is possible to separately identify cancer cells and non-cancer cells. In one exemplary embodiment, the scattered light is detected using a detector which detects a broad range of wavelength, for example, using spectrograph and/or a camera.

In another exemplary embodiment, the polyynes are used in methods of flow cytometry-based high throughput medical diagnosis. The methods involve associating one or more carbon atom wires (which may be conjugated to one or more antibodies, nucleic acids or other molecules which form a complex with specific biological markers on specific subpopulations of cells which are indicative of a particular disease state with live cells of a subject of interest, wherein specific subpopulations of the live cells are specifically associated with distinct sets of carbon atom wires. The live cells are positioned in a flow cytometer, and the live cells are illuminated within the focused flow stream of the flow cytometer, wherein the carbon atom wires are exposed to the illumination. Scattered light from the live cells is detected, and analyzed to identify individual groups of live cells. An analysis of the Raman scattering spectrum can provide a diagnosis of a specific disease, based on the binding of the carbon atom wires to specific subpopulations of cells, if present in the cell population. When bound to the carbon atom wires, the members of the specific subpopulations of cells will scatter light at specific wavelengths that unbound cells will not scatter. Thus, the presence of cells within one or more sub-populations can be detected, and correlated with a particular disease state. For example, where it is unclear whether a patient has a bacterial or viral infection, carbon atom wires conjugated to antibodies, nucleic acids or other molecules can be used which bind to bacteria, preferably to one or more specific bacteria, and if a bacteria, ideally a specific type of bacteria, is detected, appropriate antibiotics can be administered, and if a bacteria is not detected, antibiotic administration can be avoided. This can be particularly advantageous where a patient has sepsis or bacterial meningitis, and real-time assays can be particularly preferred over typical cell culture-based approaches, which often cause delays in patients receiving appropriate care.

Another exemplary embodiment involves methods of cell sorting. The methods involve associating carbon atom wires with live cells of a subject of interest, wherein specific subpopulations of the live cells are specifically associated with distinct sets of carbon atom wires. The specific subpopulations of live cells are sorted using spectroscopy, based on the specific association of the subpopulation of cells with a distinct set of carbon atom wires. Rather than using fluorescence to identify the cells, stimulated Raman spectroscopy can be used. When libraries of carbon atom wires are used, each of which binds to a different subpopulation of cells, and each of which has a different "spectral barcode," a single biological sample can be screened for multiple subpopulations of cell types.

In another exemplary embodiment, the polyynes are used to produce a cell atlas in vivo. The methods involve associating carbon atom wires with live cells of a subject of interest, wherein specific subpopulations of the live cells are specifically associated with distinct sets of carbon atom wires; mapping relationships between the specific subpopulations of live cells, wherein the specific subpopulations of live cells are distinguishable by their specific association with a distinct set of carbon atom wires.

In other embodiments, the polyynes are used in non-biological systems for identification and/or encryption purposes. In an exemplary embodiment, the polyynes are used in anti-counterfeiting methods which involve frequency encryption. The methods involve imaging a product for commercial sale using hyperspectral SRS images to identify the presence of one or more polyynes used to label the product, wherein the product for commercial sale is labelled with one or more polyynes during product manufacture, and further wherein the absence of the one or more polyynes in the hyperspectral SRS images is an indication the product is counterfeit.

In another exemplary embodiment, the polyynes are used in methods of identity security by frequency encryption. The methods involve imaging an identifying tag using hyperspectral SRS images to identify the presence of one or more polyynes used to label the tag, wherein the tag is labelled with one or more polyynes during its manufacture, and further wherein the absence of the one or more polyynes in the hyperspectral SRS images is an indication the tag is fake. In one aspect of such exemplary embodiment, the identifying tag can also include another detection method, such as a magnetic strip or a chip, which allows for two-.

A library comprising two or more polyynes can be present in a kit for imaging cultured live cells. The kit can include one or more non-specifically targeted polyynes, organelle-targeted polyynes, spectral barcoded polyynes, polyynes attached to a bead or other microparticle, and/or polyynes attached to metal nanostructures, as well as instructions for using the polyynes in cultured live cell imaging. In an exemplary embodiment, the kit comprises non-specifically targeted polyynes, organelle-targeted polyynes, and spectral barcoded polyynes, as well as instructions for using the polyynes in cultured live cell imaging.

In one exemplary embodiment, where the method and/or kit is used to search for cancer cells, stem cells, immune cells, neurons, glia, bacteria, fungi, viruses, and/or other types of biological particles, the polyynes are attached to a solid support, such as a nanoparticle, microparticle, or metal nanostructure, such as a gold particle. In one aspect of this exemplary embodiment, the diameter of the particle is between about 2 and about 200 nm, more typically, between about 2 and about 100 nm, and still more typically, between about 4 and about 50 nm.

In another exemplary embodiment, where the method and/or kit is used to identify DNA, one or more primers and/or probes are conjugated to one or more polyynes, such as polyynes of Formula I, and the one or more primers and/or probes are used in screening methods where fluorescently-labeled primers and/or probes might otherwise be used, except that, whereas fluorescence is used to detect the presence or absence of fluorescently-labeled primers and/or probes, Raman spectroscopy is used to detect the presence or absence of primers and/or probes labeled with the polyynes described herein.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 1 is length dependence of Raman vibration in phenyl-capped polyynes. (a) Normalized Raman spectra of polyynes from 2-yne to 6-yne. The spectra are vertically offset for clarity. (b) Raman intensity of polyynes increases superlinearly with conjugation length, following the power-law dependence in the double logarithmic plot. (c) Raman frequency of polyynes decreases almost linearly with increasing length, with an interval of ~40 cm-1 deviation;

FIG. 2 is Raman frequency expansion of polyynes. (a) Frequency modulation on the unified polyyne scaffold by conjugation elongation, isotope doping and end-capping variations. (b) Frequency coarse-tuning in polyynes with 13C isotope labeling (in red). (c) Frequency fine-tuning of polyynes with electron-donating and—withdrawing groups (in blue), which is complementary to the coarse-tuning range (red dash line);

FIG. 4 is super-multiplexed optical imaging with polyynes. (a) Linear concentration dependence of 4-yne with sub-μM SRS detection sensitivity. (b) Immuno-staining and imaging of α-tubulin in fixed cells with 4-yne conjugated antibody. (c) 15-color tandem fluorescence-SRS imaging of live cells with super-multiplexed polyynes. (d-h) Chemical structures and corresponding SRS (upper panel) and fluorescence images (lower panel) of five organelle-targeted probes based on polyynes for live-cell imaging, including mitochondria Mito (d), lysosome Lyso (e), plasma membrane PM (f), endoplasmic reticulum ER (g) and lipid droplet LD (h). (i) 10-color optical imaging of plasma membrane, ER, Golgi, mitochondria, lipid droplets, lysosome, nucleus, tubulin, and actin in living cells. Overlay of two species are shown in each image;

FIG. 5 is super-multiplexed optical barcoding with polyynes. (a) Polymer beads are readily encoded by combinatory loading of polyynes through physical absorption. Inset shows the bright-field image of barcoded polystyrene beads. (b) Spectral barcoding of polyynes at 10 frequencies and 3 intensities with SRS readout, which can obtain $3^{10}=59049$ distinct barcodes. (c) Cells are labeled with multiple encoded beads, as shown by the bright-field images. The barcode information is well preserved in live cells with clear readout by spontaneous Raman measurement. (d) Rapid decoding and spatial visualization of bead identities with SRS microscopy. Left: 2940 cm-1 image of unidentified beads inside living cells; Right: decoded beads in the whole field of view by hyperspectral imaging at characteristic frequencies). The color of each bead in the decoded map corresponds to the spectral barcode in (c);

FIG. 9 is live-cell SRS imaging of organelle-targeted polyynes and co-localization with fluorescent organelle markers. Characteristic labeling patterns are shown for each organelle with negligible crosstalk at 3 nm away, which displays the sharp vibrational feature of polyynes and is far beyond the spectral resolution of fluorescent dyes. High co-localizations are also observed between organelle-targeted polyynes with commercial fluorescent markers;

FIG. 11 is minimal cytotoxicity of polyynes in live cells and phototoxicity of SRS lasers. Live and dead HeLa cell standards are verified with Live/Dead viability kit. All five organelle-targeted polyynes exhibit little cytotoxicity in live cells, as shown by two-color imaging of Calcein-AM (green, live-cell marker) and EthD-1 (red, dead-cell marker). Also, Minimal photo-toxicity is observed in cells with SRS illumination. After 15 frames of continuous SRS imaging at 2940 cm-1 (protein CH3) using the same laser power and dwell time in multiplexed live-cell imaging, the same region of cells show no observable cell death in the viability assays, compared to surrounding cells without SRS laser exposure;

FIGS. 16a-d are photographs showing that hybridization chain reaction (HCR) amplification can greatly enhance SRS signal in protein imaging. 16 (a) shows an HCR scheme for protein signal amplification. Interested targets are labeled through normal immunostaining but using a DNA initiator-conjugated secondary antibody. The initiators will start a chain reaction in which two Raman dye-labeled hairpins assemble sequentially into a long double-stranded amplification polymer. 16 (b) shows amplification quantitation on rabbit α-tubulin using Alexa Fluo 647 (A647). Images for HeLa cells immunostained with normal A647-conjugated anti rabbit antibody and HCRamplified with A647-conjugated HCR amplifiers. The top row are detected by fluorescence and the bottom row are detected by SRS. "Higher settings" indicates 10-fold higher laser power. 16 (c) shows the amplification factor for HCR-A647 vs normal A647 is more than 10-fold. Error bars represent the s.e.m between different field-of-views. 16 (d) shows that the HCR method can greatly enhance SRS signal on a low abundance transmembrane tumor marker EpCAM. In these figures, the scale bars are 20 µm.

Figure 3A:
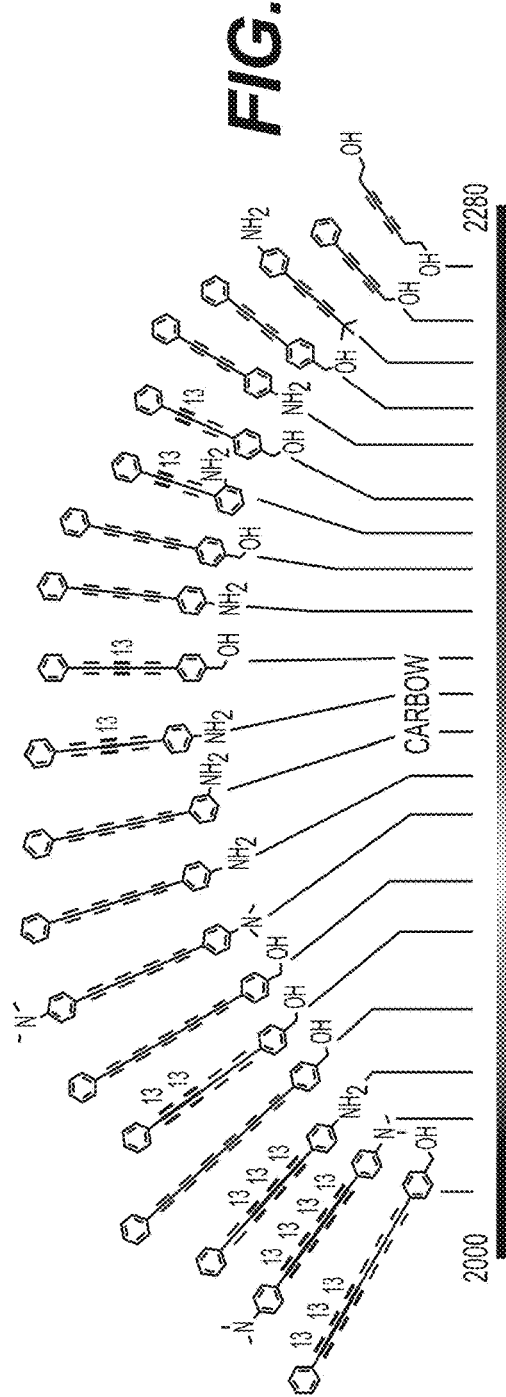
FIG. 3 is super-multiplexed polyynes. (a) Chemical structures of 20 polyynes with distinct Raman frequencies, which are termed as Carbon rainbow (Carbow). (b) Highly resolved Raman peaks of Carbow in the bioorthogonal spectral window.
Figure 3B:
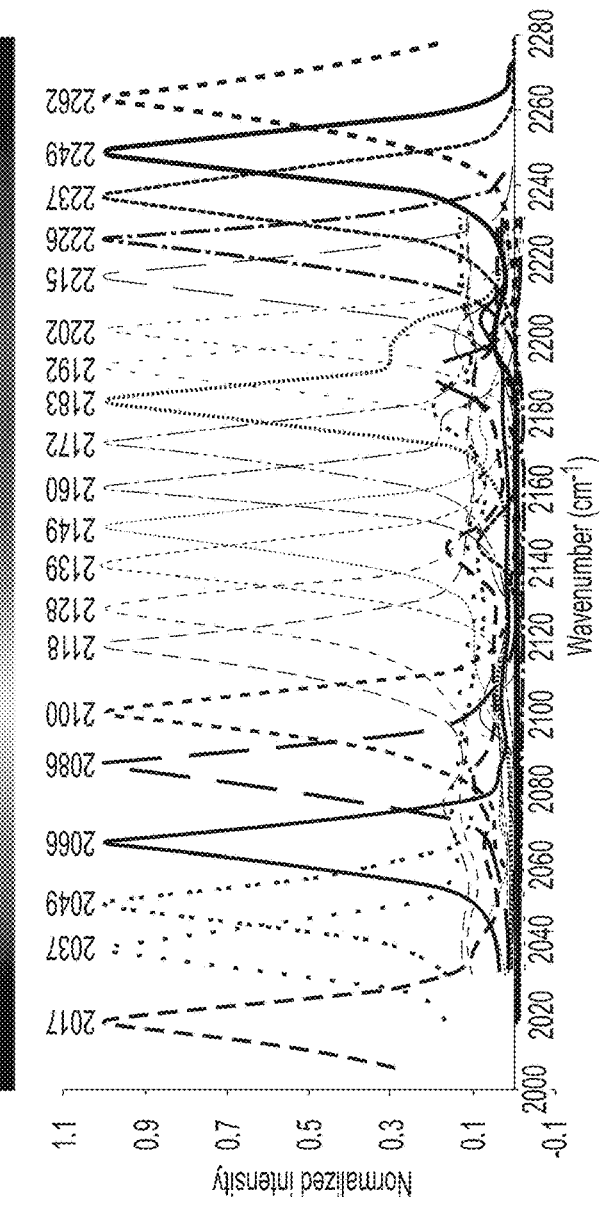

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Some modes for carrying out the present disclosure are presented in terms of its aspects, herein discussed below. However, the present disclosure is not limited to the described embodiment and a person skilled in the art will appreciate that many other embodiments of the present disclosure are possible without deviating from the basic concept of the present disclosure, and that any such work around will also fall under scope of this application. It is envisioned that other styles and configurations of the present disclosure can be easily incorporated into the teachings of the present disclosure, and only one particular configuration shall be shown and described for purposes of clarity and disclosure and not by way of limitation of scope.

Headings used herein are for organizational purposes only and are not meant to be used to limit the scope of the description or the enclosed claims. As used throughout this application, the word "may" is used in a permissive sense (i.e., meaning having the potential to), rather than the mandatory sense (i.e., meaning must). The terms "a" and "an" herein do not denote a limitation of quantity, but rather denote the presence of at least one of the referenced items.

Ranges may be expressed herein as from "about" one particular value, and/or to "about" another particular value. When such a range is expressed, another exemplary embodiment includes from the one particular value and/or to the other particular value. Similarly, when values are expressed as approximations, by use of the antecedent "about," it will be understood that the particular value forms another exemplary embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

Various exemplary embodiments of the present disclosure will be better understood with reference to the following exemplary and non-limiting definitions:

I. Exemplary Definitions

The term "independently" can be used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "alkyl," as used herein, unless otherwise specified, can refer to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, carbonate, urea, phosphonic acid, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. Specifically included are $CF_3$ and $CH_2CF_3$.

In the text, whenever the term C(alkyl range) is used, the term independently can include each member of that class as if specifically and separately set out. The term "alkyl" can include $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" can refer to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" can refer to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" can refer to an amino group that has one or two alkyl or aryl substituents, respectively.

The term "acyl" can refer to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "aliphatic" can refer to hydrocarbons which are not aromatic, including those having an open chain structure, such as alkanes, alkenes, and alkynes, ideally those with from 1-12 carbons, and cyclic hydrocarbons, ideally those with from 3-10 carbons.

The terms "alkoxy" and "alkoxyalkyl" can embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" can denote "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "aryl", alone or in combination, can mean a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties.

The terms "alkaryl" or "alkylaryl" can refer to an alkyl group with an aryl substituent. The terms "aralkyl" or "arylalkyl" refer to an aryl group with an alkyl substituent.

The term "heteroatom," as used herein, can refer to oxygen, sulfur, nitrogen and phosphorus.

The terms "heteroaryl" or "heteroaromatic," as used herein, can refer to an aromatic that includes at least one sulfur, oxygen, nitrogen or phosphorus in the aromatic ring. In some exemplary embodiments, the heteroaryl ring can be a a moiety with 5-10 ring atoms, of which 1-5 ring atoms are heteroatoms.

The term "heteroarylalkyl" can refer to a heteroaryl moiety attached to a C1-12 alkyl group.

The aryl, arylalkyl, alkylaryl, heteroaryl, and heterarylalkyl groups can optionally be substituted with any moiety that does not adversely affect the ability of the polyynes to be detected, including but not limited to those described above for alkyl moieties. Non-limiting examples of substituted aryl include heteroarylamino, N-aryl-N-alkylamino, N-heteroarylamino-N-alkylamino, heteroaralkoxy, arylamino, arylalkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy. The term "halo," as used herein, can include chloro, bromo, iodo and fluoro.

The term "heterocyclic," "heterocyclyl," and cycloheteroalkyl can refer to a nonaromatic cyclic group wherein there is at least one heteroatom, such as oxygen, sulfur, nitrogen, or phosphorus in the ring.

Nonlimiting examples of heteroaryl and heterocyclic groups can include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkylpyrimidines, N5-benzylpyrimidines, N5-halopyrimidines, N5-vinylpyrimidine, N5-acetylenic pyrimidine, N5-acyl pyrimidine, N5-hydroxyalkyl purine, and N6-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "nucleic acid" can refer to DNA, including genomic DNA and cDNA, RNA, such as siRNA, mRNA, tRNA, tmRNA, ncRNA, rRNA, shRNA, ribozymes, and the like, riboswitches, aptamers, primers, probes, and artificial nucleic acid analogues, such as peptide nucleic acids, morpholino- and locked nucleic acids, glycol nucleic acids, and threose nucleic acids.

The term "peptide" can refer to a natural or synthetic compound containing two to one hundred amino acids linked by the carboxyl group of one amino acid to the amino group of another.

The term "protected", as used herein and unless otherwise defined, can refer to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "spectral barcoded polyynes" can relate to where multiple polyynes are used, each of which has a unique spectral band. These multiple polyynes can be conjugate to, or encapsulated within, a solid support, such as a nanoparticle or microparticle. Nanoparticles typically have a size between about 2 and about 100 nm, and microparticles typically have a diameter between about 0.1 and 100 m. The solid support can also be conjugated to a binding member which is known to bind specifically to a biological particle of interest. By measuring the peaks of polyynes in the Raman spectrum from the biological sample, one can determine whether a biological particle of interest is present in a biological sample. The presence of multiple polyynes allows for the generation of multiple spectral bands, which provides a unique "barcode" to the solid support. In some exemplary embodiments, the spectral barcoding of polyynes in solid supports can be achieved by controlled physical absorption, such as using microfluidics, or controlled chemical synthesis.

The term "solid support" as used herein refers to any type of solid support to which one or more of the polyynes, and, ideally, a binding member, such as an antibody, nucleic acid, and the like, are bound. Examples include, but are not limited to, nanoparticles, including nanobeads, nanorods, nanostars and nanowires, such as metallic nanostructures and carbon nanotubes, microparticles, including microbeads, such as polystyrene microbeads, and chips.

As used herein, flow cytometry can be a laser- or impedance-based, biophysical technology employed in cell counting, cell sorting, biomarker detection and protein engineering. Cells are suspended in a stream of fluid, and passed through an electronic detection apparatus. A flow cytometer allows simultaneous multiparametric analysis of the physical and chemical characteristics of up to thousands of particles per second. A common variation involves linking the analytical capability of the flow cytometer to a sorting device, to physically separate and thereby purify particles of interest based on their optical properties. Such a process is called cell sorting, and the instrument is commonly termed a "cell sorter".

Modern flow cytometers can be used to analyze many thousand particles per second, in "real time," and, if configured as cell sorters, can actively separate and isolate particles at similar rates having specified optical properties.

A flow cytometer can have, e.g., five main components: a flow cell, a measuring system, a detector, an amplification system, and a computer for analysis of the signals. The flow cell has a liquid stream (sheath fluid), which carries and aligns the cells so that they pass single file through the light beam for sensing. The measuring system commonly use measurement of impedance (or conductivity) and optical systems—lamps (mercury, xenon); high-power water-cooled lasers (argon, krypton, dye laser); low-power air-cooled lasers (argon (488 nm), red-HeNe (633 nm), green-HeNe, HeCd (UV)); diode lasers (blue, green, red, violet) resulting in light signals. The detector and analog-to-digital conversion (ADC) system converts analog measurements of forward-scattered light (FSC) and side-scattered light (SSC) as well as dye-specific fluorescence signals into digital signals that can be processed by a computer. The amplification system can be linear or logarithmic.

The process of collecting data from samples using the flow cytometer can be termed 'acquisition'. Acquisition can be mediated by a computer physically connected to the flow cytometer, and the software which handles the digital interface with the cytometer. The software is capable of adjusting parameters (e.g., voltage, compensation) for the sample being tested, and also assists in displaying initial sample information while acquiring sample data to ensure that parameters are set correctly.

Flow cytometers can typically have multiple lasers and fluorescence detectors. Increasing the number of lasers and detectors allows for multiple antibody labeling, and can more precisely identify a target population by their phenotypic markers. Certain instruments can even take digital images of individual cells, allowing for the analysis of fluorescent signal location within or on the surface of cells.

As used herein, stimulated Raman spectroscopy flow cytometry can be a technique which combines stimulated Raman spectroscopy with flow cytometry. SRS flow cytometry, and, more specifically, a multiplex stimulated Raman scattering process, is described, for example, in Zhang et al., "Stimulated Raman scattering flow cytometry for label-free single-particle analysis," Optica, Vol. 4, No. 1/January 2017. For example, by using a 32-channel detector array, an SRS flow cytometer can detect single particles with spectral coverage of 200 $cm^{-1}$ and a throughput over 10,000 particles per second.

Stimulated Raman scattering (SRS) microscopy can be an imaging technique that looks at the vibrational frequencies of chemical bonds. Different types of bonds will have different frequencies based on the surrounding molecular environment. For example, a C—H bond on a DNA molecule (2,956 cm-1) is going to have a slightly different vibrational frequency compared to a C—H bond on proteins (2,931 cm-1) or lipids (2,854 cm-1). Unlike traditional Raman spectroscopy, SRS can obtain data on a sample rapidly, allowing for real-time, in vivo studies.

Hyperspectral imaging can be part of a class of techniques commonly referred to as spectral imaging or spectral analysis. Hyperspectral imaging is related to multispectral imaging. Hyperspectral imaging (HSI) uses continuous and contiguous ranges of wavelengths (e.g. 400-1100 nm in steps of 0.1 nm) whilst multispectral imaging (MSI) uses a subset of targeted wavelengths at chosen locations (e.g. 400-1100 nm in steps of 20 nm).

Multispectral imaging deals with several images at discrete and somewhat narrow bands. Being "discrete and somewhat narrow" is what distinguishes multispectral imaging in the visible wavelength from color photography. A multispectral sensor may have many bands covering the spectrum from the visible to the longwave infrared. Multispectral images do not produce the "spectrum" of an object.

Hyperspectral imaging can deal with imaging narrow spectral bands over a continuous spectral range, producing the spectra of all pixels in the scene. A sensor with only 20 bands can also be hyperspectral when it covers the range from 500 to 700 nm with 20 bands each 10 nm wide. In hyperspectral imaging, the recorded spectra have fine wavelength resolution and cover a wide range of wavelengths. Hyperspectral imaging measures contiguous spectral bands, as opposed to multispectral imaging which measures spaced spectral bands.

As used herein, the term "vibrational microscopy" can include spontaneous Raman microscopy, such as confocal Raman and line-scan Raman microscopy, surface-enhanced Raman scattering (SERS) microscopy, Tip-enhanced Raman scattering (TERS) microscopy, infrared microscopy, infrared-AFM microscopy, infrared photothermal microscopy, and coherent Raman microscopy, such as coherent anti-Stokes Raman scattering (CARS) microscopy.

In light of the exemplary and non-limiting definitions provided above, described below are the polyynes, conjugates of the polyynes with various biological and non-biological moieties, libraries comprising a plurality of the polyynes, the use of the polyynes in biological applications, and the use of the polyynes in non-biological applications, including non-imaging applications.

I. Polyynes

The polyynes described herein can represent a new class of 1-D optical material with wide application in super-multiplexed imaging and analysis. These compounds extend the current limit of optical super-multiplexing techniques and provides new opportunities in life science, medical diagnostics, drug discovery and data security.

A class of polyyne compounds with phenyl, alkyl, or other end-capping groups has been designed, synthesized and characterized, and their unique optical properties for super-multiplexed detection have been exploited. Polyynes are linear chains of sp-hybridized carbon atoms with alternating single and tripe bonds, which are also referred to herein as carbon-atom wires. Through systematic modulations on both the electron density and nuclear mass of polyynes by conjugation elongation, end-capping variations and isotope editing, polyynes have been developed that are an extraordinary optical material for both super-multiplexed imaging and spectral barcoding by Raman scattering.

The polyynes include anywhere from 2 to 20, preferably 3 to 20, more typically, 3 to 10, triple bonds in alternation with single bonds, preferably from 2 to 6 triple bonds. The polyynes include one or more end caps, which can be present at one or both ends of the polyynes.

The polyynes can include an end cap at either or both ends of the molecules. In an exemplary embodiment, one or both end cap(s) are, independently, aryl or heteroaryl rings, and in other embodiments, one or both end caps are alkyl, alkylaryl, arylalkyl, heterocyclic, heterarylalkyl, silyl groups, metal atoms (i.e., metal acetylides, such as silver or mercury acetylides, whether covalently bound to the terminal carbon atom or complexed to the triple bond in the terminal acetylene) or metal complex groups In some exemplary embodiments, where alkyl groups are used as one or both end caps, the alkyl groups are branched or cyclic alkyl groups rather than linear alkyl groups, and on information and belief, the branching, or steric hindrance provided by the cycloalkyl groups, can stabilize the polyyne molecules.

In some exemplary embodiments, the aryl and/or heteroaryl rings are functionalized with one or more functional groups, which can be electron donating or electron withdrawing groups.

In one aspect of such exemplary embodiment, the polyynes have the structure:

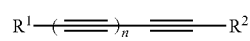

wherein n is an integer from 1 to 19, typically from 2 to 19, and still more typically, from 3 to 5, $R^1$ and $R^2$ are, independently, aryl, $C_{1-20}$ alkyl, a silyl group, a metal atom and complex, aryl-$C_{1-20}$ alkyl, $C_{1-20}$ alkyl-aryl, heteroaryl, heteroaryl-$C_{1-20}$alkyl, or $C_{1-20}$ alkyl-heteroaryl, wherein each of these groups can optionally be substituted with one or more substituents, one or more of the hydrogens in these groups can be deuterated, and one or more of the carbons in the alkyne moieties can be $^{13}C$ labeled, and wherein the substituents on one or more of the aryl, $C_{1-20}$ alkyl, aryl-$C_{1-20}$ alkyl, $C_{1-20}$ alkyl-aryl, heteroaryl, heteroaryl-$C_{1-20}$alkyl, or $C_{1-20}$ alkyl-heteroaryl groups include functional groups which can be conjugated to metal nanostructures, antibodies, peptides, nucleic acids, lipids, carbohydrates; electron withdrawing or electron donating groups which can shift the Raman spectrum of the polyynes relative to unsubstituted groups; groups which target specific organelles, cellular compartments, fluorescent labels (which can allow the polyynes to be detected using both fluorescence and Raman spectroscopy), biotin or streptavidin.

Representative substituents on one or more of the aryl, $C_{1-20}$ alkyl, aryl-$C_{1-20}$ alkyl, $C_{1-20}$ alkyl-aryl, heteroaryl, heteroaryl-$C_{1-20}$ alkyl, or $C_{1-20}$ alkyl-heteroaryl groups include, but are not limited to, one or more of halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, carbonate, urea, phosphonic acid, and phosphonate.

Representative polyynes include, but are not limited to, Carbow2172, Carbow2141, Carbow 2128, Carbow2100, Carbow2086, Carbow2066, Carbow2049, and Carbow2017, as described in the working examples.

In another aspect of such exemplary embodiment, the polyynes have well-resolved Raman peaks with less than 10% cross-talk.

Conjugation to Antibodies and Other Binding Members

Various binding members are suitable for binding to the polyynes described herein, which can allow the polyynes to be used in various detections methods described herein.

In some exemplary embodiments, the binding members are selected for their ability to specifically bind to a target of interest, and also to be capable of being attached to a polyyne. Suitable binding members include, for example, an antigen, an antibody, biotin, avidin, streptavidin, anti-biotin, folate, folate-binding protein, IgG, Protein A, Protein G, Protein L, a carbohydrate, lectin, lipid, and a nucleic acid. The binding members also include nucleic acids, including DNA, including genomic DNA and cDNA, RNA, such as siRNA, mRNA, tRNA, tmRNA, ncRNA, rRNA, shRNA ribozymes, and the like, riboswitches, aptamers, primers, probes, and artificial nucleic acid analogues, such as peptide nucleic acids, morpholino- and locked nucleic acids, glycol nucleic acids, and threose nucleic acids.

The polyynes can be bonded to the binding members either directly, as an end cap, or by attachment to a functional group on one or both end caps. Those of skill in the art can readily appreciate how to attach a binding member to an alkyne, or to an end cap.

For example, carbamate moieties on an aryl end cap can be used to conjugate antibodies or peptides. Terminal alkyne groups in the polyynes can be bonded to aryl/heteroaryl halides, for example, using palladium coupling reactions. Where a halogen is present on a base which is part of a primer or probe, this type of coupling reaction can be used to attach primers or probes directly to a polyyne as an end cap. Similarly, this type of chemistry can be used to attach other nucleic acids to the polyynes. For example, amine, carboxyl, and thiol based crosslinking chemistry, such as using NHS ester and maleimide groups, or click chemistry can be used to conjugate peptides, proteins and nucleic acids to polyynes.

Conjugation to Moieties Which Target Organelles

The polyynes have a neutral scaffold and high membrane permeability, and, as such, can be functionalized into live-cell, organelle-specific imaging probes. An appropriate linker or functional group can be used to attach different targeting groups to the polyynes. In an exemplary embodiment, the linker or functional group is present on an aryl or alkyl end cap.

The following are non-limiting examples of moieties which target organelles. Triphenylphosphonium (TPP+) is a motif with high affinity to mitochondrial matrix due to the positive charge. Other positively charged motifs can be used, which can also target the mitochondrial matrix.

The lysosome lumen is acidic, and basic motifs can be protonated and trapped inside lysosomes. Mono and dialkylamines are representative motifs which can be used. Examples include, but are not limited to, dimethylamine, diethylamine, dipropylamine, di-isopropylamine, dibutylamine, and morpholine groups.

The plasma membrane includes anionic phosphate headgroups. Cationic diammonium groups can be used to stain the plasma membrane through interaction with these anionic phosphate headgroups.

An ethylene glycol chain with different terminal groups, such as a pentafluorobenzamide group, or a glibenclamide group can be used to target the endoplasmic reticulum.

Lipid droplets are known to interact with fatty acids, so carboxylic acid and/or carboxylate-terminated fatty acid chains (typically between 8 and 21 carbons in length) can be attached either directly to the end of the polyynes, or to an aryl end cap. These fatty acid chains mimic fatty acids, allowing polyynes with this functionality to function as probes which can be efficiently incorporated into lipid droplets.

Polymers/Dendrimers Grafted with Polyynes

To further enhance the signal intensity, next-generation polyyne probes for super-multiplexed detection can be developed through multiple nanoscale signal amplification approaches.

Dendrimers and polymeric nanostructures such as bottle-brush and star-shaped nanomaterials can be grafted with multiple polyynes for topological signal amplification. For example, dendrimers are prepared in step-wise fashion, using divergent methods, convergent methods, and click methods. In divergent synthesis, the dendrimer is assembled from a multifunctional core, which is extended outward by a series of reactions, commonly a Michael reaction. In convergent synthesis, dendrimers are built from small molecules that end up at the surface of a sphere, and reactions proceed inward, building inward, and are eventually attached to a core. This method tends to provide dendrimers which are more monodisperse than when divergent synthesis is used, but the dendrimers also tend to be smaller. Click chemistry uses, for example, Diels-Alder reactions, thiolene and thiol-yne reactions, and azide-alkyne reactions. Since the polyynes (before an end cap is attached) include terminal acetylenic groups, these groups can be used in thiol-yne reactions, azide-alkyne reactions, and Diels-Alder reactions to attach the polyynes to a dendrimer.

Polyyne Coatings

Noble metal nanostructures, such as, e.g., nanospheres, nanorods and nanostars can be coated with polyyne molecules using physical adsorption or chemical modification for signal amplification through surface-enhanced Raman scattering. Traditional coating methods for coating nanostructures can be employed. For example, one method of coating nanoparticles comprises subjecting a) nanoparticles, b) a coating precursor and c) one or more polyynes which include one or more reactive groups which can react with the coating precursor, to shear, wherein the coating precursor and the one or more polyynes react to provide a coating on the nanostructures.

Attachment to Microparticles/Nanoparticles

In some exemplary embodiments, polyynes are conjugated to nanoparticles and/or microparticles (such as nanoparticles, polystyrene beads, gold particles, and the like).

Where the nano or microparticles include reactive functional groups, polyynes can be prepared which include functional groups which react with the functional groups on the nano or microparticles, and a covalent attachment between the nano or microparticles and the polyynes can be formed. However, one limitation of this approach is that the amount of polyynes attached to the particles can vary depending on the number of groups on each particle, which itself can vary, for example, depending on the particle size, and the percentage of such groups which is successfully coupled with the polyynes.

In some exemplary embodiments, it is desired to provide particles with a relatively consistent amount of the polyyne labels. One way to produce particles with a relatively constant particle size, and with a relatively consistent amount of polyynes conjugated to the particles, is to use dendrimers. The dendrimers can include a known quantity of the polyynes, by virtue of the active functional groups at the terminus on the dendrimers.

The polyynes can be conjugated to nanoparticles/microparticles by chemical means. A range of functionalized groups can be present on the polyynes, and used to attach them to the nanoparticles/microparticles, including low molecular weight ligands (Chen et al., Ligand conjugated low-density lipoprotein nanoparticles for enhanced optical cancer imaging in vivo, J. Am. Chem. Soc., 129 (18) (2007), pp. 5798-5799), peptides (Mu, et al., Anti-HER2/neu peptide-conjugated iron oxide nanoparticles for targeted delivery of paclitaxel to breast cancer cells, Nanoscale (2015), proteins (Meziani, and Sun, Protein-conjugated nanoparticles from rapid expansion of supercritical fluid solution into aqueous solution, J. Am. Chem. Soc., 125 (26) (2003), pp. 8015-8018, polysaccharides (Lemarchand, et al., Polysaccharide-decorated nanoparticles, Eur. J. Pharm. Biopharm., 58 (2) (2004), pp. 327-341), polyunsaturated and saturated fatty acids (Fahmy, et al., Surface modification of biodegradable polyesters with fatty acid conjugates for improved drug targeting, Biomaterials, 26 (28) (2005), pp. 5727-5736) DNA (Csaki, et al., The optical detection of individual DNA-conjugated gold nanoparticle labels after metal enhancement, Nanotechnology, 14 (12) (2003), p. 1262), antibodies (Arruebo, ET AL., Antibody-conjugated nanoparticles for biomedical applications, J. Nanomater., 2009 (2009), p. 37), plasmids, and siRNA.

The two main strategies for conjugating proteins/peptides/antibodies to gold nanoparticles are classic passive adsorption, and covalent conjugation.

II. Polyyne Libraries

In an exemplary embodiment, the polyynes described herein are present in libraries, for example, libraries with between 2 and 50,000 members, more typically, between 2 and about 200 members, still more typically, between 2 and about 100 members, and even more typically, between about 4 and about 50 members.

In some aspects of such exemplary embodiment, the polyyne libraries comprise a plurality of polyynes linked to antibodies, which antibodies are specific for different types of cells, including stem cells, cancer cells, bacteria, viruses, or fungi.

In other aspects of such exemplary embodiment, the polyyne libraries comprise a plurality of polyynes linked to nucleic acids, which are specific for different types of cells, including stem cells, cancer cells, bacteria, viruses, or fungi.

In still other aspects of such exemplary embodiment, the polyyne libraries comprise a plurality of polyynes linked to primers, which primers can be used in genetic screening applications to identify the presence of single nucleotide polymorphisms, such as cytochrome P450 mutations, to identify types of mutations present in viruses, such as HIV, which can be indicative of drug resistance, or in cancer cells, such as HER2 and other mutations, which can be useful in determining an appropriate course of treatment for a patient. In this aspect, the use of polyyne labels replaces the use of fluorescent labels in PCR techniques, and the use of Raman spectroscopy replaces the detection of fluorescence. Because multiple "barcoded" primers can be screened for at once, all with distinguishable signals, this allows for the simultaneous detection of multiple mutations in a single scan.

In all aspects of such exemplary embodiment, the individual polyynes can include structural differences, such as isotopic labeling, difference in the numbers of alkyne moieties, and end cap functionalization, so as to provide a plurality of polyynes, which provide signals in Raman spectroscopy with minimal "crosstalk" with respect to each other.

The libraries can include polyynes with up to 50 distinct frequencies, ranging from about 1850 to about 2600 $cm^{-1}$, with single strong peak and minimal crosstalk. Up to 50-channel parallel optical detections can be achieved in tandem with fluorescence within this frequency range. With super-multiplexed polyynes, up to 50 color live cell imaging, typically up to 30 color live cell imaging, and, more typically, up to 15-color live-cell imaging can be achieved, without the need of complicated un-mixing, within this frequency range.

In addition, libraries useful for optical data storage and identification applications can include sufficient polyynes to generate a significant number of distinct barcodes, for example, up to around $10^{13}$ barcodes, and, in some exemplary embodiments, at least around 50,000 or more distinct barcodes. These distinct barcodes can be achieved, for example, even with libraries including only up to around 200 individual polyynes. For example, a barcode can include one or more polyynes, each of which has its own signal, preferably a signal which does not "cross-talk" more than about 10% with a signal associated with an adjacent polyyne (i.e., a polyyne which has a Raman spectral peak adjacent to a Raman spectral peak of another polyyne).

With just three polyynes in a library, one can create numerous barcodes. For example, if all of the polyynes are present at the same concentration, one can have polyyne 1, polyyne 2, polyyne 3, polyynes 1 and 2, polyynes 1 and 3, polyynes 2 and 3, and polyynes 1, 2, and 3, a total of seven combinations. However, the polyynes can be present in different concentrations, which will provide Raman spectral peaks with different heights (signal intensities). Typically, one can distinguish up to about 5 different concentrations. So, with just three polyynes, at five different possible concentrations, one has $6^3$ possible combinations (i.e., more than 200 possible combinations). Thus, with up to 200 polyynes, it is possible to have a very significant number of possible combinations of polyynes, at multiple possible concentrations of the polyynes.

In order to have multiple polyynes, whether or not they are present at multiple concentrations, it can be advantageous to have an intimate mixture of the polyynes in a solid structure, such as an ID badge, passport, driver's license, credit card, merchandise tag, currency, bonds, such as bearer bonds or other financial instruments, and articles of manufacture, such as medicines, containers, clothing, shoes, handbags, DVDs and the like. The unique Raman signature of thus-labeled articles can help prevent identity theft, property theft, counterfeiting, document forgery, and the sale and/or consumption of adulterated drugs.

In some exemplary embodiments, the libraries include polyynes complexed with nano- and/or microparticles, and in other embodiments, the libraries include polyynes which are not complexed with nano- and/or microparticles. In still other embodiments, the libraries include combinations of polyynes, complexed and not complexed with nano- and/or microparticles.

III. Polyyne Synthesis

One aspect of the polyyne synthesis involves coupling two or more acetylene moieties together to form a polyyne. Representative coupling chemistry includes Glaser coupling, the Eglinton Reaction, Hay coupling, and Cadiot-Chodkiewicz Coupling.

The Eglinton Reaction is an oxidative coupling of terminal alkynes, and allows the synthesis of symmetric or cyclic bisacetylenes via reaction of the terminal alkyne with a stoichiometric amount of a copper(II) salt in pyridine.

Glaser Coupling is a synthesis of symmetric or cyclic bisacetylenes via a coupling reaction of terminal alkynes. Mechanistically, the reaction is similar to the Eglinton Reaction; the difference being the use of catalytic copper(I), which is reoxidized in the catalytic cycle by oxygen in the reaction medium.

The related Hay Coupling, which involves using a copper-TMEDA (N,N,N',N-Tetramethylethylenediamine) complex to perform the coupling step, has several advantages as compared with the Glaser Coupling. The copper-TMEDA complex used is soluble in a wider range of solvents, so that the reaction is more versatile.

Cadiot-Chodkiewicz Coupling allows for the formation of asymmetric acetylenes, and involves the copper(I)-catalyzed coupling of a terminal alkyne and an alkynyl halide.

All of these coupling chemistries are compatible with a variety of substitution on an end-cap, such as an aryl end cap, on one or both of the alkynes being coupled. To the extent a substituent on an end cap is not compatible with one of these coupling chemistries, the substituent can in some cases be protected. The use of protecting groups is well known to those of skill in the art (see, for example, T. W. Green, P. G. M. Wuts, Protective Groups in Organic Synthesis, Wiley-Interscience, New York, 1999, 27-33, 708-711).

Although the Cadiot-Chodkiewicz Coupling chemistry can be used to form asymmetric acetylenes, and the other reactions tend to form symmetric acetylenes, they can also be used to form asymmetric acetylenes when mixtures of acetylenic monomers are used. For example, a mixture of acetylene A and acetylene B will form dimers AA, AB, and BB, which can be separated into individual dimers.

When the polyyne has three or more alkynyl moieties, a halo-alkynyl moiety on one side can be linked to an alkyne with a protecting group, such as a trialkylsilyl protecting group, on the other side. Following the coupling step, the protecting group can be removed, and a terminal alkyne is formed. This terminal alkyne can be coupled with other halo-alkynes.

The haloalkynes themselves can be prepared, for example, by reacting N-bromosuccinimide (NBS) with an acetylene in the presence of silver nitrate.

The polyynes described herein include isotopically-labeled compounds, which are identical to those recited in the various formulae and structures presented herein, but for the fact that one or more atoms are replaced by an atom having an atomic mass or mass number different from the atomic mass or mass number usually found in nature.

In other embodiments are examples of isotopes that are incorporated into the present compounds including isotopes of hydrogen, carbon, nitrogen, oxygen, fluorine and chlorine, such as, for example, $^{2}H$, $^{3}H$, $^{11}C$, $^{13}C$, $^{14}C$, $^{15}N$, $^{18}O$, $^{17}O$, $^{35}S$, $^{18}F$, $^{36}Cl$, respectively.

Isotopically-labeled compounds, for example those into which isotopes such as $^{13}C$ or $^{2}H$ are incorporated, are useful in drug and/or substrate tissue distribution assays.

When such is desired, a $^{13}C$ label can be present on one or more individual alkynes when the alkynes are coupled together to form the polyynes. Further, a deuterium or tritium label can be present on one or both end caps.

Further, in some exemplary embodiments, substitution with isotopes such as deuterium, i.e., $^{2}H$, can afford certain advantages, resulting from greater metabolic stability, such as, for example, increased in vivo half-life.

It is expected that single or multiple replacement of hydrogen with deuterium (carbon-hydrogen bonds to carbon-deuterium bond) at site(s) of metabolism will slow down the rate of metabolism. This can provide the compounds a relatively longer half-life, and slower clearance from the body. Methods for incorporating deuterium into organic derivatives are well known to those of skill in the art. Representative methods are disclosed in *Angew. Chem. Int. Ed. Engl.* 2007, 46, 7744-7765. Accordingly, using these techniques, one can provide one or more deuterium atoms in the polyynes.

End caps can either be present on the alkynes when they are coupled, or can be applied after the coupling chemistry is complete. For example, a phenyl group with a halo substituent, such as a bromo or iodo substituent, can be attached to a terminal alkyne via palladium coupling chemistry. Representative conditions are disclosed, for example, in Swenton et al., ChemInform 56(21) (1991). An alkyl group can be attached, for example, using nucleophilic substitution, by first deprotonating a terminal alkyne, for example, by reaction with a strong base such as butyl lithium, and then displacing a leaving group, such as a halogen, tosylate, and the like, on a methyl, primary or secondary alkane (Id.).

With respect to functionalizing the aromatic (aryl, heteroaryl) end caps, those of skill in the art can readily introduce a wide variety of functional groups onto aryl or heteroaryl moieties.

Where it is desirable to provide substitution on the aryl rings, electrophilic aromatic substitution can be used to provide certain desired functionality. For example, alkyl, aryl, heteroaryl, alkaryl, arylalkyl, alkenyl, alkynyl, and acyl groups can be added using Friedel-Crafts alkylation/arylation/acylation reactions. Other electrophilic aromatic substitution reactions can be used, for example, to provide halogens, such as by forming chloronium or bromonium ions in situ and reacting them with the aromatic ring, or by forming sulfonium or nitronium ions to provide sulfonyl or nitro groups.

Friedel Crafts alkylation is conducted using an appropriate halo-alkyl moiety, and a Lewis acid. The alkyl moiety forms a carbocation, and electrons from the aryl ring form a bond with the carbocation, placing a positive charge on the aryl ring. The aryl ring then loses a proton. Alkyl and alkaryl moieties (such as benzyl moieties) can be added in this fashion.

Friedel Crafts acylation is similar, but uses an acid halide, such as an acid chloride, to place a ketone moiety on the ring. The acid halide can be an alkyl acid, such as acetic acid, propionic acid, butyric acid, and the like, or can be an aromatic acid, such as benzoic acid, p-toluic acid, and the like.

Friedel Crafts arylation (also known as the Scholl reaction) is a coupling reaction with two aryl rings, catalyzed by a Lewis acid. The proton lost during the coupling reaction serves as an additional catalyst. Typical Reagents are iron (III) chloride in dichloromethane, copper(II) chloride, PIFA and boron trifluoride etherate in dichloromethane, Molybdenum(V) chloride and lead tetraacetate with BF3 in acetonitrile.

Electrophilic aromatic substitution can also be carried out on certain 5-membered heteroaryl rings. Unsubstituted pyrrole, furan, and thiophene can be converted into substituted aromatic heterocycles through electrophilic substitution. In this respect, furan, thiophene, pyrrole and their derivatives are all highly activated compared to benzene. These compounds all contain an atom with an unshared pair of electrons (oxygen, sulphur, or nitrogen) as a member of the aromatic ring, which substantially increases the stability of the cationic intermediate. As with benzene rings, these substitutions take place by an initial electrophile addition, followed by a proton loss from the "onium" intermediate to regenerate the aromatic ring. The aromatic five-membered heterocycles all undergo electrophilic substitution, with a general reactivity order: pyrrole>>furan>thiophene>benzene. Substitution is typically at the 2-position. Examples of electrophilic substitutions to pyrrole are the Pictet-Spengler reaction and the Bischler-Napieralski reaction.

Additionally, substituted five-membered-ring heteroaryls can also be synthesized through the cyclization of 1,4-diketones in combination with ammonia, amines, phosphorus pentoxide, or phosphorus pentasulfide. The ring-closure is preceded by dehydration (condensation), which then yields the two double bonds and, thus, the aromatic pi system. The formation of the energetically favored aromatic system is one of the driving forces of the reaction. Functional groups present on the 1,4-diketones or amines is then incorporated into the heteroaryl rings.

The scattering wavelength (i.e., Raman frequencies) of the polyynes can vary depending on a number of factors, including the presence or absence of deuterium or 13C labeling, the number of alkyne groups in the polyynes, the presence of, type of, and substitution present on the end caps, and the like. For example, electron donating and electron withdrawing groups on aryl/heteroaryl rings can alter the Raman frequencies of the polyynes relative to unsubstituted aryl/heteroaryl rings.

Those of skill in the art understand what functional groups are electron donating and electron withdrawing. Representative electron donating groups include, but are not limited to, phenol/phenoxide, tertiary amines, secondary amines, primary amine, ethers, alkyl groups, aryl groups, and vinyl groups. Representative electron withdrawing groups include, but are not limited to, triflates, nosylates, brosylates, tosylates, trihalides, such as —CF3 and —CCl3, nitriles, sulfonates, nitro groups, ammonium salts, quaternary ammonium salts, aldehydes, ketones, carboxylic acids, acyl halides, such as acyl chlorides, esters, amides, and halides.

In another exemplary embodiment one or both end caps are alkyl groups, preferably branched alkyl groups, as the branching can lend stability to the molecules. As discussed above, for methyl, primary or secondary alkyl moieties, an acetylenic ion can be used in a nucleophilic displacement reaction to provide an alkyl end cap. Sonogashira coupling of alkynes with alkyl halides can also be performed, and the coupling is tolerant to a wide range of functional groups, including ether, ester, amide, nitrile, keto, heterocycle, acetal, and aryl halide, in both coupling partners. The coupling can be selective for a specific C—X bond (X=I, Br, Cl) and allows for orthogonal functionalization of alkyl halides with multiple reactive sites (Vechorkin et al., J. Am. Chem. Soc. 131, 34, 12078-12079).

Representative syntheses are provided in the working examples.

IV. Methods of Identifying Biological Particles of Interest

In some exemplary embodiments, antibodies, peptides, nucleic acids, and other materials which bind to biological particles of interest (i.e., binding members) can be labeled with one or more polyynes as described herein, and used to determine the presence or absence of a biological particle of interest.

In some aspects of such exemplary embodiment, the methods are used to determine whether or not a biological particle of interest, such as a cancer cell, stem cell, immune cell, neuron, glia, bacteria, virus, or fungi is present or absent in a biological sample taken from a patient.

Representative biological samples include, but are not limited to, whole blood, blood products, such as plasma or serum, cerebral spinal fluid, urine, seminal fluid, saliva, nipple aspirate, lymph, fine needle aspirate, water, cerebrospinal fluid, ascites, pleural fluid, and synovial fluid.

Representative biological particles include, but are not limited to, stem cells, cancer cells, red blood cells, white blood cells, granulocytes, platelets, monocytes, neutrophils, lymphocytes, bacteria, viruses, and fungi.

In an exemplary embodiment, antibodies, nucleic acids or other materials which bind to biological particles of interest (i.e., binding particles) are conjugated to one or more polyynes as described herein to form polyyne-labeled antibodies, nucleic acids and the like.

A biological sample from a patient can then be incubated with the polyyne-labeled antibodies, nucleic acids, and the like. If the biological sample includes a biological particle of interest, it will form a conjugate with the polyyne-labeled antibody, nucleic acid, and the like.

Conjugate formation (and, thus, the presence of the biological particle of interest) can be confirmed by identifying the presence of a polyyne-labeled antibody, nucleic acid, and the like, on the biological particle.

This detection can be accomplished using techniques known to those of skill in the art. For example, polyyne-conjugated antibodies, oligonucleotides, and the like can be subjected to super-multiplexed imaging of antigen proteins and nucleic acids in fixed cells and tissues through immunohistochemistry, immunocytometry in situ hybridization, and the like. These techniques can optionally be further combined with sequential immunolabeling and imaging for a higher level of multiplexing, as well as specimen expansion and clearing techniques for super-resolution and deep-tissue super-multiplexed imaging and detection.

Similarly, if labeled with different antibodies, nucleic acids and the like, polyynes can be used in cell sorting applications, particularly when combined with flow cytometry or other related techniques. For example, normal cells and cancer cells can be easily separated due to the presence of distinct protein types on their respective surfaces. One of ordinary skill will understand how to conjugate antibodies, nucleic acids and the like with the polyynes described herein (also referred to as "carbon atom wires"), as well as how to label live cells extracted from a patient with antibody-carbon atom wire conjugates, and how to conduct flow cytometry of the labelled sample.

In such exemplary embodiment, the cell sorting technique is similar to fluorescence-activated cell sorting (FACS), which is a specialized type of flow cytometry, but rather than using fluorescence, the technique uses Raman spectroscopy to identify cells with polyyne labels.

Similarly, bacteria, viruses, and fungi are known to have various targets, such as receptors, on their respective surfaces. These targets can be conjugated with various antibodies, nucleic acids, and like binding members.

In an exemplary embodiment, a biological sample is incubated with one or more polyyne-labeled antibodies, nucleic acids, and the like, which specifically bind to cancer cells, stem cells, bacteria, fungi, or viruses, and if the biological sample includes a cancer cell, stem cell, bacteria, fungi, or virus which binds to the labeled antibodies, nucleic acids and the like, a conjugate will form. This conjugate will have an identifiable polyyne label, which can be detected, for example, using stimulated Raman spectroscopy, spontaneous Raman spectroscopy, infrared spectroscopy or other coherent Raman techniques.

Using flow cytometry, or similar techniques where biological particles flow past a light source, one can determine the presence of absence of conjugates between the biological particles of interest and the polyyne-labeled antibodies, nucleic acids, and the like, by detecting the presence of a specific polyyne.

That is, if a biological sample is subjected to flow cytometry, the particles will flow through a tube and can pass by a source of radiation. Where the particles are conjugated with a particular antibody/nucleic acid, which in turn is conjugated to a particular polyyne, the presence of the polyyne (as detected using the source of radiation) in the conjugate means that the biological particle associated with this antibody/nucleic acid is present in the biological sample. When a particular polyyne is not detected, this means that the biological particle associated with this antibody/nucleic acid is not present in the biological sample.

Libraries of polyyne-labeled antibodies, nucleic acids and the like can be prepared, for example, containing a plurality of different antibodies, nucleic acids, and the like, which can bind specifically to a number of biological particles if such are present in the biological sample. By using a variety of polyynes, each of which is bound to a different antibody/nucleic acid, one can identify the presence or absence of specific types of biological particles in a biological sample.

This technique can allow for rapid detection not only of a bacterial, viral, or fungal infection, but can also allow for the rapid determination of the specific type of bacteria, virus, or fungi.

This technique can also be used to rapidly detect the presence or absence of cancer cells. In an exemplary embodiment, following surgical removal of a tumor, samples of tissues, for example, tissues taken from near the surgical site, can be evaluated for the presence or absence of cancer, to ensure that wide enough margins were taken to ensure the entire tumor was removed.

In some exemplary embodiments, the polyynes are used to image cultured live cells. The methods involve culturing live cells, which can be derived from an in vitro tissue cell culture of interest, extracted from an in vivo subject of interest, seeding the cultured live cells in wells, and labelling each well with a single color of polyynes in culture media, wherein the polyynes comprise one or more colors. The labelled cultured live cells are then added to an imaging chamber for stimulated Raman microscopy, and the cells are imaged using stimulated Raman microscopy, wherein each cell is maintained with a single color during the imaging period.

In other embodiments, the polyynes are used to image organelles in cultured live cells. The methods involve culturing live cells, which can be derived from an in vitro tissue cell culture of interest or extracted from an in vivo subject of interest, incubating the cultured live cells with polyynes in culture media, wherein the polyynes each comprise a specific organelle-targeted probe, labelling the cultured live cells with the polyynes, and imaging the cells using stimulated Raman microscopy. In one aspect of such exemplary embodiment, the cultured live cells are seeded in a well before they are incubated and labelled with the polyynes, and then the cells are labelled with the polyynes, wherein the polyynes each comprise a specific organelle-targeted probe, which probes specifically target different organelles. Representative organelle-targeted probes include probes which target the plasma membrane, endoplasmic reticulum (ER), Golgi, mitochondria, lipid droplets, lysosome, nucleus, and tubulin in the cultured live cells.

In still other embodiment, the polyynes are used in methods of live-cell tagging using spectral barcoded beads. The methods involve mixing polymeric microbeads, such as polystyrene beads, with spectral barcoded polyynes, binding the beads with the spectral barcoded polyynes to form barcoded beads, and culturing live cells, which can be derived from in vitro tissue cell culture of interest, or extracted from an in vivo subject of interest. The barcoded beads are incubated with the cultured live cells in culture media, which labels the cultured live cells with the barcoded beads. The cultured live cells can then be imaged using stimulated Raman microscopy, and the spectral barcodes of the barcoded beads in the whole field of view can be decoded based on hyperspectral SRS (Stimulated Raman scattering) images.

In another exemplary embodiment, the polyynes are used to identify a population of cancer cells using flow cytometry, or other methods for sorting/counting cells. The methods involve associating one or more polyynes (also referred to herein as "carbon atom wires") with live cells of a subject of interest, wherein the carbon atom wires are conjugated with antibodies that detect, and bind to, specific cell surface markers of the live cells, and further wherein the antibodies bind to cell surface markers of the live cells. The live cells are positioned in a focused flow stream of a flow cytometer; and illuminated within the focused flow stream of the flow cytometer with a predetermined wavelength of light. The cells are exposed to the illumination, and light is deflected as it comes into contact with the cells. The resulting scattered light from the live cells is detected, and the Raman scattering spectrum is analyzed to identify individual groups of live cells. Cells that are not cancer cells are not linked to the carbon atom wire-conjugated antibodies, whereas cancer cells are linked to the carbon atom wire-conjugated antibodies. The cancer cells are detected based on the Raman spectra of scattered light produced by the carbon atom wires conjugated with antibodies. In another exemplary embodiment, the polyynes are used in methods of flow cytometry-based high throughput medical diagnosis. The methods involve associating one or more carbon atom wires, in some aspects, conjugated to a solid support, such as a nano- or microparticle, and which may be conjugated to one or more antibodies, nucleic acids or other binding molecules which form a complex with specific biological markers on specific subpopulations of cells which are indicative of a particular disease state, with live cells of a subject of interest, wherein specific subpopulations of the live cells are specifically associated with distinct sets of carbon atom wires. The live cells are positioned in a flow cytometer, and the live cells are illuminated within the focused flow stream of the flow cytometer, wherein the carbon atom wires are exposed to the illumination. Scattered light from the live cells is detected, and analyzed to identify individual groups of live cells. An analysis of the scattered light can provide a diagnosis of a specific disease, based on the binding of the carbon atom wires to specific subpopulations of cells, if present in the cell population. When bound to the carbon atom wires, the members of the specific subpopulations of cells will scatter light at specific wavelengths that unbound cells will not scatter. Thus, the presence of cells within one or more sub-populations can be detected, and correlated with a particular disease state. For example, where it is unclear whether a patient has a bacterial or viral infection, carbon atom wires can be selected which bind to bacteria, preferably to one or more specific bacteria, and if a bacteria, ideally a specific type of bacteria, is detected, appropriate antibiotics can be administered, and if a bacteria is not detected, antibiotic administration can be avoided. This can be particularly advantageous where a patient has sepsis or bacterial meningitis, and real-time assays can be particularly preferred over typical cell culture-based approaches, which often cause delays in patients receiving appropriate care. Another exemplary embodiment involves methods of cell sorting. The methods involve associating carbon atom wires with live cells of a subject of interest, wherein specific subpopulations of the live cells are specifically associated with distinct sets of carbon atom wires. The specific subpopulations of live cells are sorted using spectroscopy, based on the specific association of the subpopulation of cells with a distinct set of carbon atom wires. Rather than using fluorescence to identify the cells, stimulated Raman spectroscopy can be used. When libraries of carbon atom wires are used, each of which binds to a different subpopulation of cells, and each of which has a different "spectral barcode," a single biological sample can be screened for multiple subpopulations of cell types.

In another exemplary embodiment, the polyynes are used to produce a cell atlas in vivo. The methods involve associating carbon atom wires with live cells of a subject of interest, wherein specific subpopulations of the live cells are specifically associated with distinct sets of carbon atom wires; mapping relationships between the specific subpopulations of live cells, wherein the specific subpopulations of live cells are distinguishable by their specific association with a distinct set of carbon atom wires.

One example of how this technique can be used is in the screening for meningitis, primarily to determine whether the meningitis is bacterial or viral, and where it is bacterial, which bacteria is present. A sample of cerebrospinal fluid (CSF) can be obtained from a patient, and incubated with polyyne-labeled antibodies/nucleic acids which bind to those bacteria or viruses responsible for meningitis. The sample can then be subjected to flow cytometry or other techniques where biological particles flow past a source of radiation. Where light scattering, such as that measured using stimulated Raman spectroscopy, indicates that a biological particle is present or absent (by virtue of the biological particle being bound to a polyyne-labeled antibody/nucleic acid), appropriate therapy can be prescribed. Where the meningitis is viral, administration of antibiotics can be avoided. Where the meningitis is bacterial, an appropriate antibiotic can be administered. This technique can also be used to rapidly diagnose sepsis. The large library of polyynes can be used for parallel detection of different targets, such as different types of meningitis, allowing fast screening with reduced wait time over typical ELISA assays requiring secondary enzymatic reactions.

In some exemplary embodiments, the polyynes are conjugated not only to binding materials such as antibodies, nucleic acids and the like, but also to nanoparticle or microparticles, such as gold particles, polystyrene beads, and the like. In other embodiments, the polyynes are conjugated to metal nanowires. In still other embodiments, the polyynes are not conjugated to any nanoparticles or microparticles. By conjugating to micro/nanoparticles, higher detection sensitivity and more spectral barcodes can be achieved with enriched polyynes and combinatory labeling in micro/nanoparticles.

In some aspects of these exemplary embodiments, polymers which bind to a binding agent, including proteins and peptides, such as antibodies and antibody fragments, nucleic acids, including primers and probes, and other binding agents as described herein, are also linked, whether through binding or physical entrapment, to a plurality of polyynes as described herein. In addition to binding to the binding agent, the polymers can also be covalently linked to a plurality of polyynes as described herein, or the polymers can be formed into nanoparticles or microparticles, and polyynes are physically entrapped into the nanoparticles or microparticles during their formation.

Representative ways to covalently attach a plurality of polyynes to a polymer, which can be a graft, comb, or other suitable polymer, include providing a polymer with a plurality of reactive groups, and a plurality of polyynes with a plurality of functional groups capable of participating in coupling reactions with the reactive groups on the polymer, and performing a coupling reaction to couple the polymer to the plurality of polyynes. It can be difficult to control the amount of polyynes which are added to a particular polymer, particularly if the polymer is a polydisperse polymer. In those embodiments where control of the amount of polyyne attached to a polymer, it can be preferred to use a dendrimer, or a monomer with a low degree of polydispersity.

Representative ways to physically entrap the polyynes into nano- and/or microparticles include, but are not limited to, having the polyyne(s) present during a polymerization reaction which convert monomers to polymer particles; spray drying conditions which convert polymer solutions to polymer nano- or microparticles; and precipitation-based approaches, where a polymer and one or more polyynes as described herein are dissolved in a solution. The polymer and polyyne(s) are precipitated from solution, ideally while the solution is rapidly stirred, and the precipitation can be accomplished, for example, by removing a solvent or co-solvent, adding a non-solvent, adjusting the pH, adjusting the ionic strength of the solution, and the like. This causes the polymer and the one or more polyynes to precipitate out of solution and form nano- or microparticles. These techniques for forming nano- and microparticles are well known to those of skill in the art.

In still other exemplary embodiments, the polyynes are not conjugated to nanoparticles or microparticles, but the signal is amplified using various biological techniques, such as polymerase amplification when a target being screened is genetic material, and Hybridization Chain Reaction (HCR) when the target is a peptide or protein. In some aspects of these exemplary embodiments, the screens can be conducted in a high-throughput manner by using chip-based screening methods and/or multiplexed polymerase amplification or HCR techniques. These exemplary embodiments are discussed in more detail below.

Hybridization/Amplification Techniques

In some cases, a target, such as a target nucleic acid, a protein, or a peptide, is present in a sample at a low enough concentration that there may be insufficient binding of the polyynes to enable facile detection. Representative target nucleic acids include nucleic acid sequences, epigenetic modifications, single nucleotide polymorphisms, deletions, and additions, and representative proteins and/or peptides include antigens, proteins with post-translational modifications, as well as primary antibodies which bind to antigens.

In such cases, it may be useful to amplify the signal. There are a variety of biological techniques useful for signal amplification. Some biological techniques, such as polymerase amplification, are specific for amplification related to nucleic acid targets. Other biological techniques, such as hybridization chain reaction, are specific for amplification related to protein and peptide targets.

In molecular biology, hybridization, where single-stranded deoxyribonucleic acid (DNA) or ribonucleic acid (RNA) molecules anneal to complementary DNA or RNA, can be used to amplify signals obtained from genetic screening assays. Though a double-stranded DNA sequence is generally stable under physiological conditions, changing these conditions in the laboratory (generally by raising the surrounding temperature) will cause the molecules to separate into single strands. These strands are complementary to each other but may also be complementary to other sequences present in their surroundings. Lowering the surrounding temperature allows the single-stranded molecules to anneal or "hybridize" to each other.

Hybridization, as used herein, can include molecular biology techniques such as Southern blots, Northern blots, the polymerase chain reaction (PCR), and other conventional approaches to DNA sequencing.

A real-time polymerase chain reaction (Real-Time PCR), also known as quantitative polymerase chain reaction (qPCR), monitors the amplification of a targeted DNA molecule during a polymerase chain reaction (PCR) in real-time, and not at its end, as in conventional PCR. In some aspects of this exemplary embodiment, real-time PCR can be used quantitatively (quantitative real-time PCR), and in others, semi-quantitatively, i.e. above/below a certain amount of DNA molecules (semi quantitative real-time PCR).

Representative common methods for detecting PCR products in real-time PCR include, but are not limited to: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In exemplary embodiments which are variations of both of these methods, the fluorescent dyes/reporters can be replaced with one or more of the polyyne labels described herein.

Conventional multiplex polymerase chain reaction (Multiplex PCR) involves using the polymerase chain reaction to amplify several different DNA sequences simultaneously (as if performing many separate PCR reactions all together in one reaction). This process amplifies DNA in samples using multiple primers, and a temperature-mediated DNA polymerase, in a thermal cycler. In some aspects of this exemplary embodiment, the sequencing is performed in a multiplexed manner.

Multiplex-PCR can use multiple primer sets within a single PCR mixture to produce amplicons of varying sizes, which are specific to different DNA sequences. By targeting multiple sequences at once, additional information may be gained from a single test run that otherwise would require several runs. Annealing temperatures for each of the primer sets must be optimized to work correctly within a single reaction. In some exemplary embodiments, particularly those where amplicon sizes overlap, different amplicons can be differentiated and visualized using labeled primers, each of which is labeled with a different polyyne described herein. One difference between this approach and conventional multiplex-PCR is that conventional multiplex-PCR uses fluorescent dyes, but in this exemplary embodiment, one or more primers in a primer set is labeled with a polyyne label. In contrast to fluorescent labels, where "cross-talk" between fluorescent labels minimizes the number of primers which can be used, there can be significantly less cross-talk using the polyyne labels described herein, allowing a greater number of labeled primers to be used multiplex-PCR screens.

In another exemplary embodiment, kits for performing multiplex PCR using one or more primers labeled a polyyne as described herein are provided. The kits include between two and about fifty primers, such as between two and about twenty primers, one or more of which is labeled with a polyyne as described herein, as well as a DNA polymerase, such as a Taq polymerase. The kits may also include appropriate buffers, which can optionally also include optimized salt concentrations for PCR amplification. Representative salts which can be used include magnesium salts, such as magnesium chloride, and potassium salts, such as potassium chloride, and/or ammonium salts, such as ammonium sulfate. PCR additives that facilitate amplification of difficult templates by modifying the melting behavior of DNA can also be present. Dimethylsulfoxide (DMSO) is another commonly used additive in PCR kits. Such additives are well known to those of skill in the art.

Representative applications for performing multiplex PCR using the polyyne-labeled primers, and multiplex PCR kits described herein, include detection of cancer, typing and analysis of transgenic organisms, amplification and analysis of microsatellites, typing and detection of bacteria and viruses, and amplification of multiple DNA regions for analyzing single nucleotide polymorphisms (SNPs), deletions, such as single feature polymorphisms (SFP-InDel (deletions), repeats, and epigenetic modifications. Multiplex PCR using the reagents described herein can be used to discover novel SNPs, and detect known SNPs.

In use, where a primer binds to a target nucleic acid of interest, for example, indicating that a SNP is present in a biological sample, the presence of the primer binding can be determined by the presence of a Raman spectral peak associated with a specific polyyne label, The absence of the primer binding can be determined by the absence of this Raman spectral peak. Thus, one can determine whether or not a target nucleic acid of interest is present by incubating the primer with the target nucleic acid, forming an amplicon if the primer binds to the target nucleic acid, and detecting the label on the amplicon, if present, using Raman spectroscopy. Where multiple primers are used, this technique can be used to simultaneously determine the presence or absence of multiple target nucleic acids. In some aspects of this exemplary embodiment, the number of primers coupled to a polyyne of Formula I is between 2 and 100.

Fluorescence in situ hybridization (FISH) is a laboratory method used to detect and locate a DNA sequence, often on a particular chromosome. In one exemplary embodiment, one or more of the fluorescent labels used in this technique are replaced with the polyyne labels described herein.

Where the target is a protein or peptide, one can use techniques such as Hybridization Chain Reaction (HCR) amplification to amplify the signal.

Hybridization chain reaction amplifications can use metastable nucleic acid monomers which self-assemble upon exposure to an initiator, such as a target analyte, as a way to amplify a signal so as to detect an analyte in a sample. The sample can be contacted with a first metastable monomer comprising an initiator complement region and a second metastable monomer comprising a region that is complementary to a portion of the first monomer. Representative monomers include, for example, hairpin nucleic acid structures comprising a loop region and a duplex region.

The first and second monomers polymerize in the presence of an initiator. Preferably, hybridization of the initiator to the initiator complement region of the first monomer initiates polymerization. Polymerization continues until the supply of one of the monomers is exhausted. The identification of polymers comprising the first and second monomers is indicative of the presence of the analyte in the sample. While polymers may be identified, for example, by gel electrophoresis, the presence of the polyyne dye enables one to detect the polymers using spectroscopic techniques, such as Raman spectroscopy, including SRS.

The initiator can be a nucleic acid. In some exemplary embodiments, the analyte comprises the initiator. In other embodiments the sample can additionally be contacted with an initiation trigger. The initiation trigger can include the initiator and a binding molecule, such as an aptamer, that is able to specifically recognize the analyte of interest. The initiator can hybridize to the first monomer and trigger polymerization when the binding molecule is bound by the analyte. In one embodiment the analyte is a nucleic acid that is associated with a pathogen, such as a bacteria, fungi, or a virus, such as HIV. The sample may be a biological sample from a patient.

In some aspects of this exemplary embodiment, as shown in FIG. 16a, an antigen of interest binds to a primary antibody, and the primary antibody binds to a DNA initiator-conjugated secondary antibody. The DNA initiator-conjugated secondary antibody only forms a complex with the primary antibody if the primary antibody has formed a complex with an antigen of interest. It does not form a complex with the primary antibody if it has not formed a complex with the antigen of interest.

Thus, in one exemplary embodiment, if one obtains a biological sample from a mammal, such as a human, and incubates this sample with a primary antibody which specifically binds to an antigen of interest if the antigen of interest is present in the biological sample, one can form a complex of the primary antibody and the antigen if the antigen is present in the biological sample, but will not form a complex if the antigen is not present in the biological sample. In this exemplary embodiment, the mammal has not developed a primary antibody to the antigen of interest. In other exemplary embodiments, the mammal has already developed a primary antibody to the antigen of interest, so there is no need to incubate the biological sample with a primary antibody.

Whether or not the biological sample included an antigen of interest, but no primary antibody, and the sample was incubated with a primary antibody to form a complex, or the biological sample already included a complex between a primary antibody and an antigen of interest, one can then add a DNA initiator-conjugated secondary antibody. The DNA initiator-conjugated secondary antibody forms a complex with the primary antibody if the primary antibody has formed a complex with the antigen of interest.

When the secondary antibody forms a complex with a primary antibody, which is indicative of the presence of an antigen of interest in the biological sample, the DNA initiator in the DNA initiator-conjugated secondary antibody can cause polymerization of nucleic acid monomers. Representative nucleic acid monomers include hairpin structures, typically two hairpin structures, at least of which is labeled with a polyyne as described herein, which has a known Raman scattering peak. By adding these two hairpin nucleic acid structures, if the DNA initiator-conjugated secondary antibody has formed a complex with the primary antibody, the initiator then starts a chain reaction in which the two hairpins assemble sequentially into a double-stranded amplification polymer, which double-stranded amplification polymer comprises at least one polyyne of Formula I.

The presence or absence of the double-stranded amplification polymer can then using Raman spectroscopy, by determining the presence or absence of the at least one polyyne of Formula I based on the known Raman scattering peak(s). One can then determine the presence or absence of the antigen of interest based on the presence or absence of the known vibrational peak(s) associated with the at least one polyyne. That is, the polyyne will only be present in the Raman spectrum if polymerization was initiated; polymerization will only be initiated if the secondary antibody has bound to the primary antibody, and the secondary antibody will only bind to the primary antibody if the primary antibody is also bound to the antigen of interest. In some aspects of this exemplary embodiment, the HCR amplification reaction is carried out in a multiplex fashion. In some aspects of this exemplary embodiment, the number of nucleic acid monomers coupled to a polyyne, and the number of secondary antibodies, is between 2 and 100.

As described elsewhere herein, suitable initiators can start a chain reaction in which two polyyne-labeled hairpins assemble sequentially into a long double-stranded amplification polymer. Using the polyyne-labeled monomers, such as polyyne-labeled hairpin nucleic acid structures, one can achieve significantly higher signal amplification with the absence of self-quenching relative to where the monomers are labeled with a fluorescent label.

In still other exemplary embodiments, the presence or absence of an antigen of interest in a biological sample can be determined without the need for amplification. For example, a primary antibody can be used to bind to an antigen in a biological sample, if the antigen is present. By conjugating one or more polyynes to the primary antibody, either directly, or by binding the antibody and one or more polyynes to a solid support, one can detect the presence of an antigen of interest by its binding to the (directly or indirectly) labeled primary antibody.

Similarly, a primary antibody which binds to an antigen, if present in a biological sample, can either be added to the biological sample, or can already be present, in the event the subject from which the biological sample has been derived had been exposed to the antigen, and already developed an antibody response. A secondary antibody, which binds to the primary antibody if the primary antibody has bound to an antigen of interest, can be added. This second antibody can be labeled with one or more polyynes, either directly, or by binding the antibody and the one or more polyynes to a solid support. The presence of the antigen can be determined by screening for the presence of the polyynes, which are present on the secondary antibody, which binds to the first antibody, which binds to the antigen. If the antigen is not present, the primary antibody will not be bound to an antigen, so the secondary antibody will not bind to the primary antibody, so there will be no signal to detect that shows the presence of the antigen of interest.

Exemplary Applications Beyond Imaging

The ability to multiplex is beyond imaging. Polyynes can be applied to informatics by super-multiplexed spectral barcoding, demonstrating optical data storage and identification. In the current era of personalized medicine, bead-based suspension assays hold great promise to achieve high-throughput multiplexed analysis, the core of which is the capacity of distinguishable barcodes for accurate detection. Polyynes not only have a high number of well-resolved peaks for straightforward spectral encoding and decoding, but also Raman scattering is intrinsically free from photobleaching or the complication of resonance energy transfer in fluorescence, due to the ultrashort lifetime of virtue state. Thus, with polyynes, frequency-domain barcoding can reach very high number through combinatory encoding.

Figure 12:
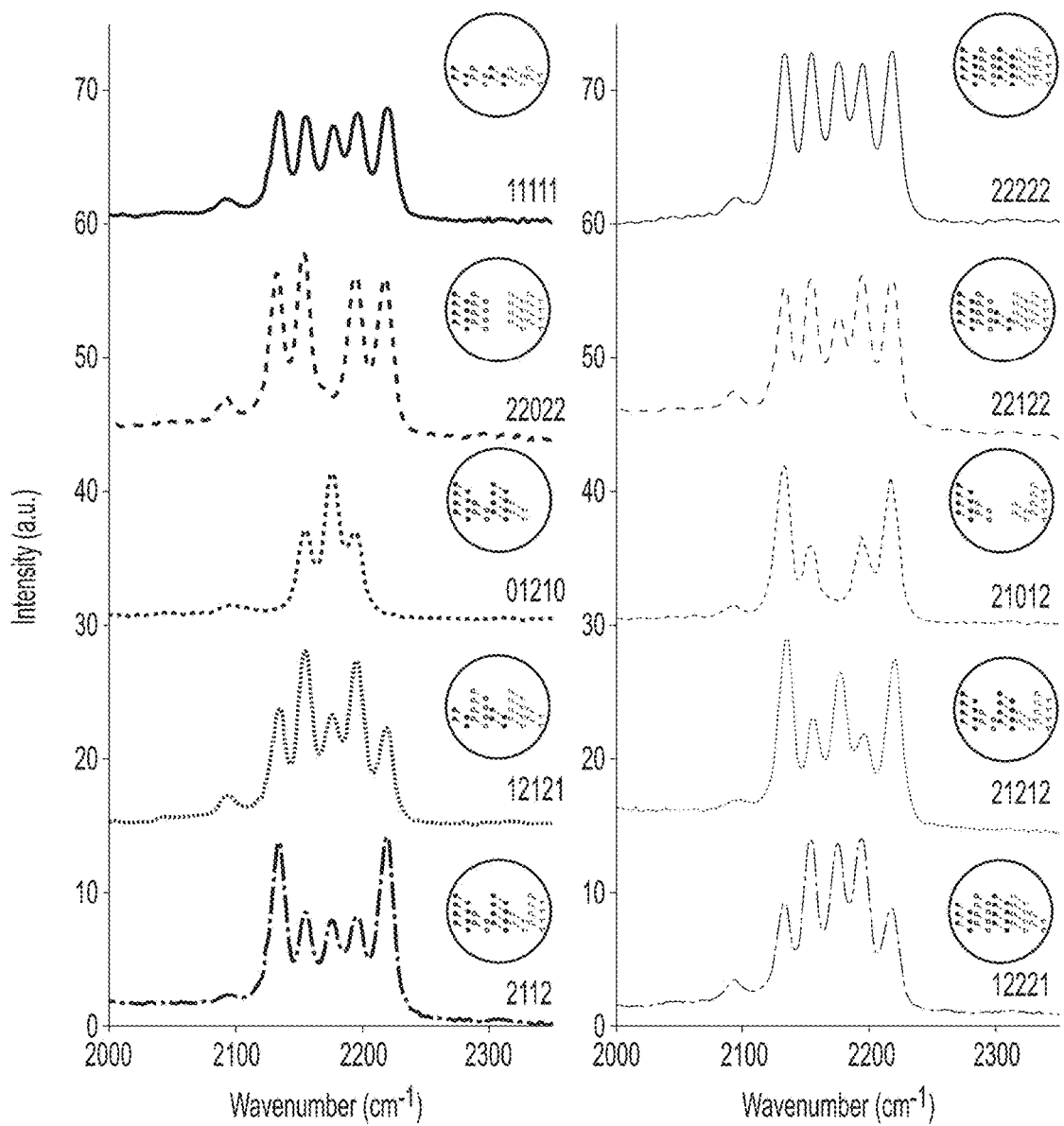
FIG. 12 is 10 representative spectral barcodes in polystyrene beads by confocal Raman microscope. 5 polyynes (Carbow2141, Carbow2160, Carbow2183, Carbow2202 and Carbow2226) that are compatible with 532 nm excitation are used in spectral encoding for spontaneous Raman measurement (Table 2)

Multiplexing can be useful in applications beyond imaging. Systems biology and personalized medicine benefit from high-throughput analysis of cells and biomolecules such as antigens and drugs, and the technology often requires distinguishable barcoding on micro-objects such as beads. Carbow has been applied to optical data storage (i.e., encoding) and identification (i.e., decoding). Harnessing polymer beads as the information carrier, spectral barcoding with ten resolvable frequencies at three distinct intensity levels (i.e., ternary digit) is achievable using Carbow (FIG. 5). 3-μm-sized polystyrene beads with specified polyyne mixtures were loaded via a swelling-diffusion technique, and each bead was encoded with the desired spectral information in a single preparation step (FIG. 5a). As illustrated by four representative codes decoded by SRS readout, the intensity at each of the ten specified frequencies can be unambiguously digitalized as either 0, 1 or 2 (FIG. 5b and Table 1). Spectral barcodes can also be read out by conventional spontaneous Raman spectroscopy, and ten spectral patterns are decoded at the single-particle level (FIG. 12 and Table 2). All nine combinations from two adjacent frequencies are well identified, demonstrating robustness against cross-talk. Thus, $3^{10}-1=59048$ distinct spectral barcodes can be generated, whereas the previous record is around 1,000. Compared with previous optical barcoding materials, Carbow not only affords more resolvable frequencies, which benefit combinatorial coding exponentially, but is also free from photobleaching or complication of energy transfer as in fluorescence.

Recently, multichannel SRS flow cytometry has been reported to detect polymer beads with a throughput of 11,000 particles per second. Coupled with SRS flow cytometry, micron-sized beads encoded with polyynes can be applied in high-throughput suspension assays to simultaneously detect tens of thousands of targets for diagnostic analysis.

beads to tag each cell generates $^{59048}C_3=3\times10^{13}$ IDs sufficient to barcode all cells in the human body (~$10^{13}$ cells). This is orders of magnitudes greater than the limit of current state-of-the-art techniques based on organic dyes, quantum dots and up-conversion nanocrystals or whispering-gallery mode detection of bead diameters.

Hence, polyynes have been engineered into imaging and barcoding probes for optical supermultiplexing, surpassing the existing 'multiplexing ceiling'. The strong signals of polyynes arise from superlinear second hyperpolarizability enhancement of the linearly conjugated triple bonds under electronic nonresonant conditions, whereas MARS dyes derive their signals from electronic preresonant enhancement of planarly conjugated chromophores. In the exemplary demonstrated applications, stringent laser preresonance conditions are not required, and these applications further expand and better separate frequencies with less cross-talk and no need of unmixing. Carbow probes are also more suitable for live-cell application and spectral barcoding because of their neutral scaffolds of polyynes. The current technology can be further improved. From a material perspective, more colors can be accessible with longer polyynes. The frequencies of polyynes can red shift toward 1,850 cm$^{-1}$ with increasing length, providing an expanded window of 150 cm$^{-1}$. From a microscopy perspective, SRS imaging of single organelles in live cells can be achieved in as short as 2 s per frame (FIG. 13), and high-speed hyper-

TABLE 1

Recipe of 10-digit barcoding for SRS measurement

| Barcode | Carbow 2017 (μM) | Carbow 2036 (μM) | Carbow 2066 (μM) | Carbow 2100 (μM) | Carbow 2119 (μM) | Carbow 2141 (μM) | Carbow 2160 (μM) | Carbow 2183 (μM) | Carbow 2202 (μM) | Carbow 2226 (μM) |
|---|---|---|---|---|---|---|---|---|---|---|
| 1111111111 | 7.3 | 7.2 | 3.4 | 3.0 | 12.8 | 4.0 | 23.6 | 9.2 | 25.5 | 42.5 |
| 1212121212 | 7.9 | 15.0 | 3.6 | 8.1 | 14.4 | 11.0 | 22.7 | 20.9 | 13.2 | 85.7 |
| 2101221012 | 14.3 | 7.0 | 0.0 | 2.8 | 25.3 | 7.8 | 22.3 | 0.0 | 34.4 | 83.6 |
| 0121001210 | 0.0 | 7.2 | 7.0 | 2.9 | 0.0 | 0.0 | 23.1 | 18.6 | 15.4 | 0.0 |

TABLE 2

Recipe of 5-digit barcoding for confocal Raman measurement

| Barcode | Carbow2141 (μM) | Carbow2160 (μM) | Carbow2183 (μM) | Carbow2202 (μM) | Carbow2226 (μM) |
|---|---|---|---|---|---|
| 11111 | 15.3 | 57.7 | 31.2 | 51.9 | 93.2 |
| 22222 | 29.4 | 111.1 | 60.2 | 100.0 | 179.5 |
| 01210 | 0.0 | 59.1 | 64.0 | 26.6 | 0.0 |
| 12121 | 16.6 | 113.6 | 30.8 | 127.8 | 91.9 |
| 21112 | 32.7 | 56.1 | 30.4 | 50.5 | 181.5 |
| 12221 | 16.6 | 113.6 | 61.5 | 102.2 | 91.8 |
| 21012 | 32.7 | 56.1 | 0.0 | 84.2 | 181.4 |
| 21212 | 29.8 | 56.3 | 61.0 | 25.3 | 181.9 |
| 22022 | 23.6 | 111.6 | 0.0 | 167.5 | 180.5 |
| 22122 | 29.4 | 111.1 | 30.1 | 125.0 | 179.6 |

Figure 13:
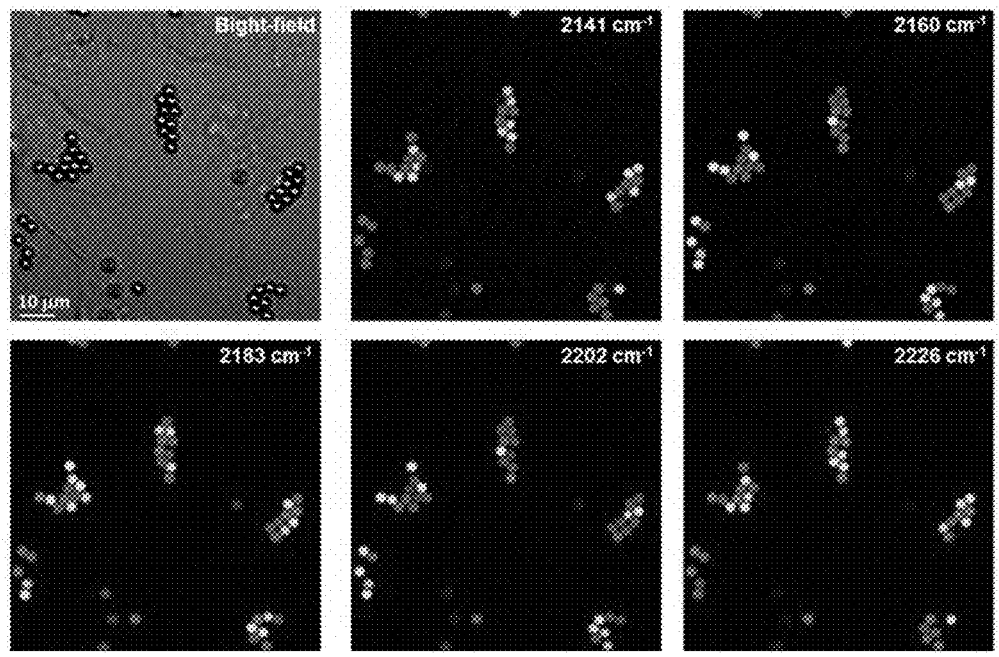
FIG. 13 is hyperspectral SRS imaging of encoded beads in live cells. Bright-field image shows the spatial distribution of unidentified beads in cells. Consecutive SRS imaging at characteristic frequencies of polyynes allows rapid decoding and visualization of bead identity in space. Color indicates signal intensity, yellow color indicates stronger signal, while red color indicates weaker signal.
Figure 14:
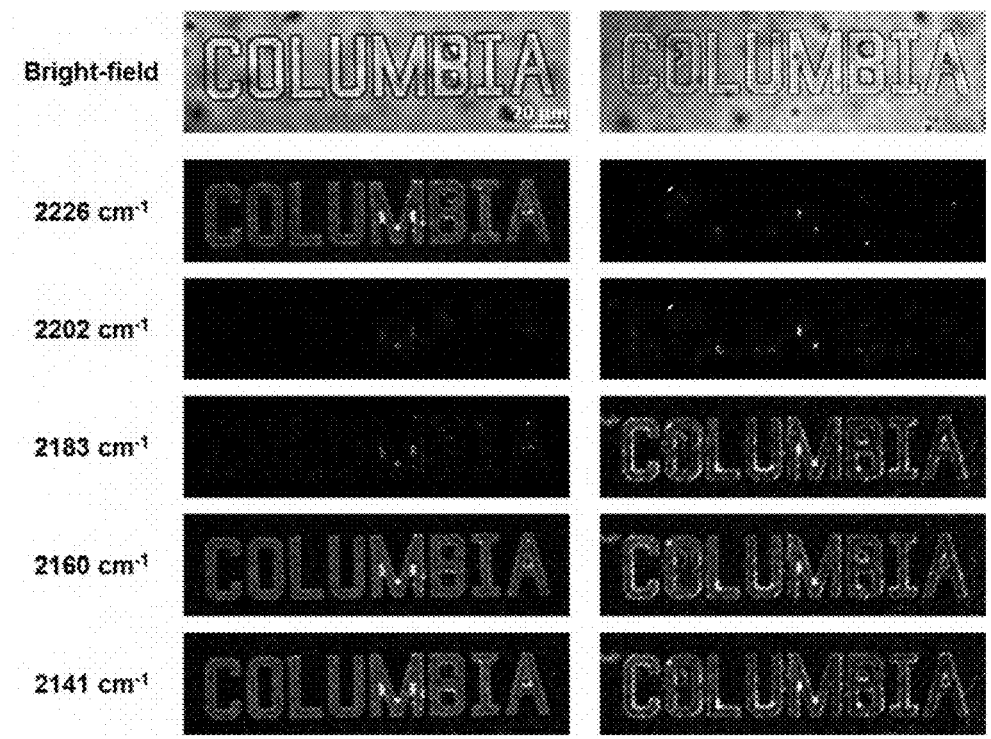
FIG. 14 is frequency encryption with polyynes for identity security and anti-counterfeiting. Microscopic Columbia logos on PDMS look similar in the bright-field images and hyperspectral SRS images reveal the true identity of both logos in the frequency domain. For example, Columbia in red is counterfeit and Columbia in blue is authentic.

Besides in vitro detection, barcoded beads can potentially be used as a unique ID to tag individual cells. Owing to their small size, multiple beads can be combined in tagging a single cell. HeLa cells can take up several beads containing different barcodes. The encoded information is retained inside live cells after 24 h and can be read out by spontaneous Raman spectroscopy (FIG. 5c). Furthermore, besides measuring the spectrum of one bead at a time, hyperspectral SRS imaging at discretized frequencies can decode all beads in the field of view (FIG. 5d and FIG. 13), allowing rapid visualization of cellular identity. Hence, if using 3 encoded spectral SRS imaging can be applied to capture fast dynamics of live cells. From a barcoding perspective, beads functionalized with antibodies or enzymes can be applied for medical diagnostics and drug discovery. SRS flow cytometry can also be employed to detect tens of thousands of beads per second. In addition, using barcoded beads, the interactions of cells can potentially be mapped, for example, for the human cell atlas project. Lastly, as a proof of principle for identity security and anticounterfeiting applications, we demonstrate frequency encryption in a microscopic pattern (FIG. 14). With continuing probe development and the implementation of high-speed hyperspectral detection, polyynes represent a new class of 1-D optical material that can have wide application in super-multiplexed imaging and analysis, providing exciting opportunities in life science, medicine, and information storage. The exemplary embodiments of the present disclosure can also be used in blockchain applications; polyynes can be conjugated to metal nanostructures to greatly enhance the Raman scattering signal by orders of magnitude. This new structure of polyynes-attached metal nanostructures can be used for immunohistochemistry of human tissues and offers multiplex imaging of a large number of markers.

Exemplary embodiments of the present disclosure can provide a new set of material for optical super-multiplexing applications, such as imaging probes, diagnostic assays, personalized medicine and data security. Multiple organelle-targeted probes are developed for multicolor microscopy in live cells and bead-based spectral encoding demonstrated in the exemplary embodiments of the present disclosure can be widely applied in multiplexed suspension assays for medical diagnostics and drug discovery. Additionally, the exemplary embodiments of the present disclosure can be used in optical information storage and document security for anti-counterfeiting application. Further, with nanoscale signal amplification, the exemplary embodiments of the present disclosure can be used in multiplexed immuno-imaging and detection of antigens and nucleic acids for disease diagnostics and personalized medicine.

Molecular probes based on polyynes target different species in live cells for multiplexed microscopy. Polyyne encoded bead surfaces are functionalized with different bioactive molecules such as antibody and enzyme for in vitro assays. Surface-functionalized beads are combined with SRS flow cytometry in bead-based suspension assays for high-throughput multiplexed detection in clinical diagnostics and drug discovery. Information encryption techniques are based on super-multiplexed polyynes for data security. Nanoscale signal amplification techniques are used to enhance the signal of polyynes. Signal enhanced polyyne probes are conjugated to antibodies and oligonucleotides for super-multiplexed immuno-imaging of antigens and nucleic acids in fixed cells and tissues.

In addition, through combinatory encoding of polyynes in polymer beads, super-multiplexed spectral barcoding to achieve nearly 60,000 distinct barcodes for optical readout was demonstrated. This could be combined with recently reported SRS flow cytometry in bead-based suspension assays for high-throughput medical diagnostics and drug discovery. In addition, polyynes can be used to generate tens of trillion optical IDs for individual cell labeling in human cell atlas, which are many orders of magnitudes greater than the upper limit of current state-of-the-art techniques based on fluorescent dyes, quantum dots and up-conversion nanocrystals. Moreover, super-multiplexed polyynes can be applied to optical data storage and information encryption for potential document security and anti-counterfeiting applications.

Exemplary embodiments of the present disclosure will be better understood with reference to the following non-limiting examples. Herein are described methods, materials, and procedures for the practice of an embodiment of the present disclosure. One of ordinary skill will understand that the present disclosure is not limited to the below disclosed methods, materials and procedures. One of ordinary skill will understand that the present disclosure may be used in conjunction with therapeutic and diagnostic approaches relevant to specific cell types in both plants and mammals. Further aspects and advantages of the present disclosure will appear from the following description taken together with the accompanying drawings.

EXAMPLES

Specific compounds which are representative of this exemplary embodiment of the present disclosure were prepared as per the following examples and reaction sequences; the examples and the diagrams depicting the reaction sequences are offered by way of illustration, to aid in the understanding of the exemplary embodiments of the present disclosure, and should not be construed to limit in any way the exemplary embodiments of the present disclosure set forth in the claims which follow thereafter. The present compounds can also be used as intermediates in subsequent examples to produce additional compounds of the exemplary embodiments of the present disclosure. No attempt has necessarily been made to optimize the yields obtained in any of the reactions. One skilled in the art would know how to increase such yields through routine variations in reaction times, temperatures, solvents and/or reagents.

As shown in the following synthetic examples, 20 well-resolved Raman frequencies were obtained on representative polyynes, which in tandem with fluorescence can achieve 30-color optical detection. This set of polyynes is referred to herein as "carbon rainbow" or "Carbow." With the super-multiplexed polyynes, simultaneous 15-channel optical imaging was demonstrated in live cells, which is among the highest reported in all fluorescence- and Raman-based methods. The polyynes exhibited excellent live-cell compatibility with minimal cytotoxicity and outstanding photostability, and are particularly suitable for intracellular imaging with high cell permeability and little non-specific background. 5 organelle-targeted polyynes were successfully developed to achieve 10-color organelle imaging in live cells with high specificity and negligible cross-talk.

Figure 6:
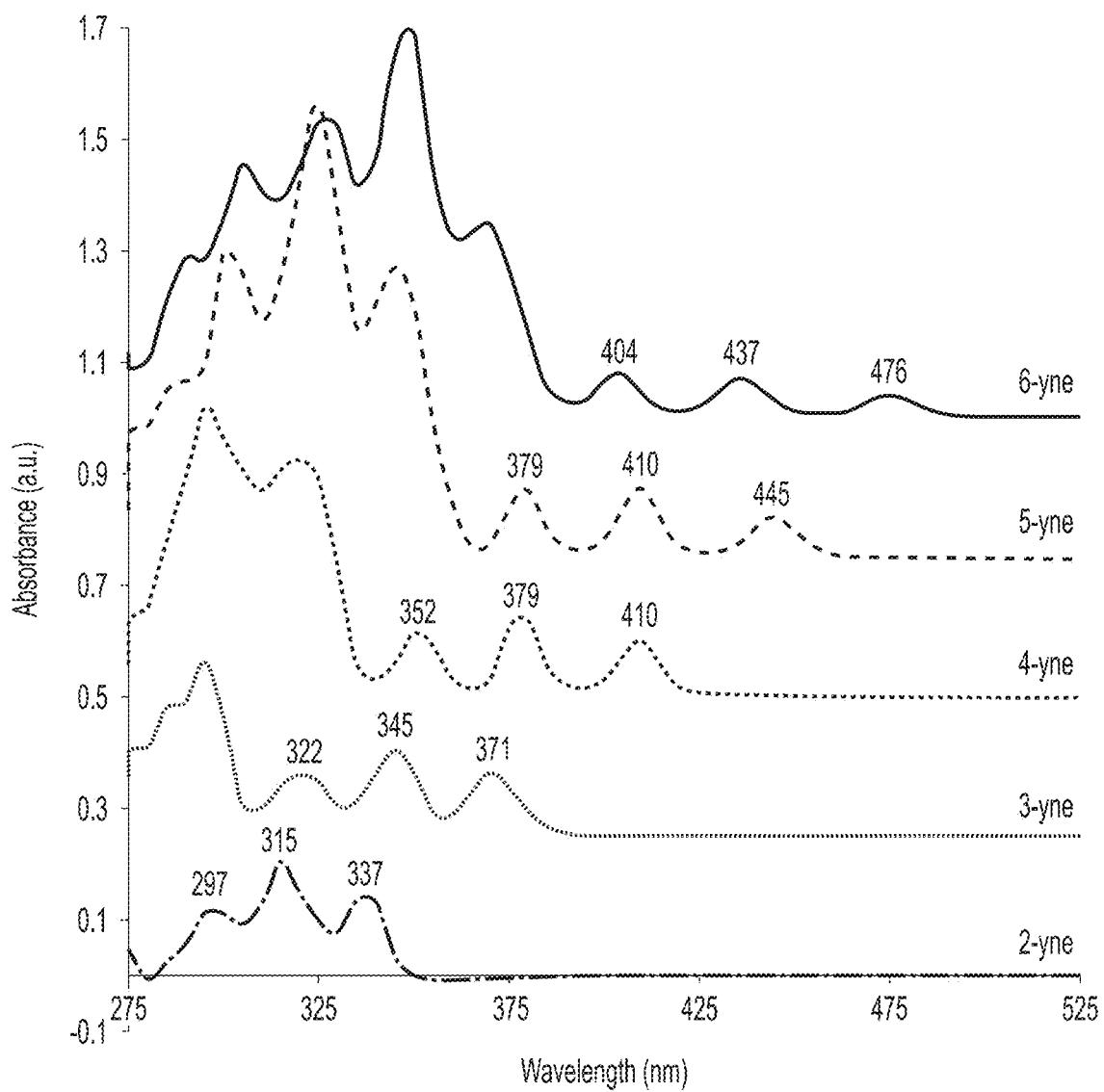
FIG. 6 is UV-Vis absorption spectra of polyynes from 2-yne to 6-yne. The spectra are vertically offset for clarity. The absorption maxima redshift ~35 nm with every additional triple bond. Three sets of peaks are clearly observed at the highest wavelengths as vibrational fine structures, indicating strong vibronic coupling.

A series of polyynes with phenyl end-capping groups was synthesized and characterized. Using Glaser-Hay and Cadiot-Chodkiewicz coupling, an efficient and robust route was used to prepare both odd- and even-numbered polyynes with two to six triple bonds (C≡C) (FIG. 1). A polar hydroxymethyl group is introduced on the phenyl ring for facile purification and serves as an active site for subsequent functionalization. UV-Vis spectra show the longest wavelengths of absorption in polyynes shift from UV (337 nm) to visible (476 nm) region with clear vibronic progression (FIG. 6), as the length increases from 2-yne to 6-yne with lowering HOMO-LUMO bandgap. All polyyne compounds disclosed herein show good chemical stability under ambient conditions, as characterized by NMR and mass spectrometry.

These phenyl-capped polyynes exhibit unique vibrational spectroscopic properties. They all display an intense Raman peak with narrow linewidth (13 cm$^{-1}$) (FIG. 1a), originated from a collective out-of-phase bond-length alternation oscillation of both single and triple bonds. Such a single sharp peak in the Raman-silent spectral region promises sensitive and specific detection. In addition, as the number of triple bonds increases from two to six, the Raman intensity grows superlinearly with a power-law exponent of 2.77±0.06 (FIG. 1b). This trend is similar to the dependence observed in the second hyperpolarizability of other conjugated oligomers, which suggests much higher detection sensitivity than a single alkyne. More importantly, going from 2-yne to 6-yne, the peak frequencies of polyynes shift almost linearly from 2,226 cm$^{-1}$ to 2,066 cm$^{-1}$ (FIG. 1c), naturally separating these polyynes in the frequency domain. Therefore, the unique spectral features of a single intense peak, narrow linewidth and the natural frequency spacing of different lengths render these polyynes an ideal scaffold for optical multiplexing.

With the single strong peak, narrow linewidth and the natural frequency spacing in polyynes of different lengths, the carbon-atom wire scaffold was further engineered to expand the Raman frequency for super-multiplexed optical detection (FIG. 2a). Vibrational frequency is known to be determined by two independent factors, one is the force constant of the vibrational mode, related to the electron density between nucleus, and the other is the reduced mass of the mode, linked to the weight of individual nucleus. By modulating both the reduced mass and the force constant of the vibrational mode, coarse- and fine-tuning of polyyne frequency ranging from 80 cm$^{-1}$ to 2 cm$^{-1}$ can be achieved. Isotope doping is an effective approach to modify the reduced mass, which can strongly influence the Raman frequency. With multiple triple bonds in polyyne, the $^{13}$C isotope labeling pattern can be optimized and one or more triple bond at selective positions can be modularly doped, which can precisely tune the frequency of polyynes in a large range of 20-80 cm$^{-1}$; the frequency-shifting effect of doping multiple triple bonds appears to be additive, as illustrated by singly, doubly and triply 13C-labeled 4-yne series (FIG. 2b). The appearance of minor peaks in isotope edited polyynes is attributed to the IR-active modes resulted from violation of mutual exclusion, likely due to the breakdown of polyyne centrosymmetry with non-uniform $^{13}$C labeling.

Substituting the end-capping phenyl ring with electron-donating or electron-withdrawing groups allows for tuning the vibrational frequency by influencing π-electron delocalization on the polyyne chain (FIG. 2c). Indeed, with electron-donating dimethylamine —N(CH$_3$)$_2$, doubly substituted 4-yne shows a significant redshift of 23 cm$^{-1}$, whereas the electron-withdrawing trifluoromethyl —CF$_3$ blue shifts by 3 cm$^{-1}$, compared to 4-yne at 2,141 cm$^{-1}$. The exact substitution position also matters. With the same —NH$_2$, para-position shows the largest redshift (2,128 cm$^{-1}$) due to the strong mesomeric effect. Ortho-position (2,133 cm$^{-1}$) is next, and meta-position (2,139 cm$^{-1}$) is the weakest. Thus, end-capping substitution provides the frequency fine-tuning (2-20 cm$^{-1}$), which is complementary to the coarse-tuning (20-80 cm$^{-1}$) from 13C doping.

Figure 7:
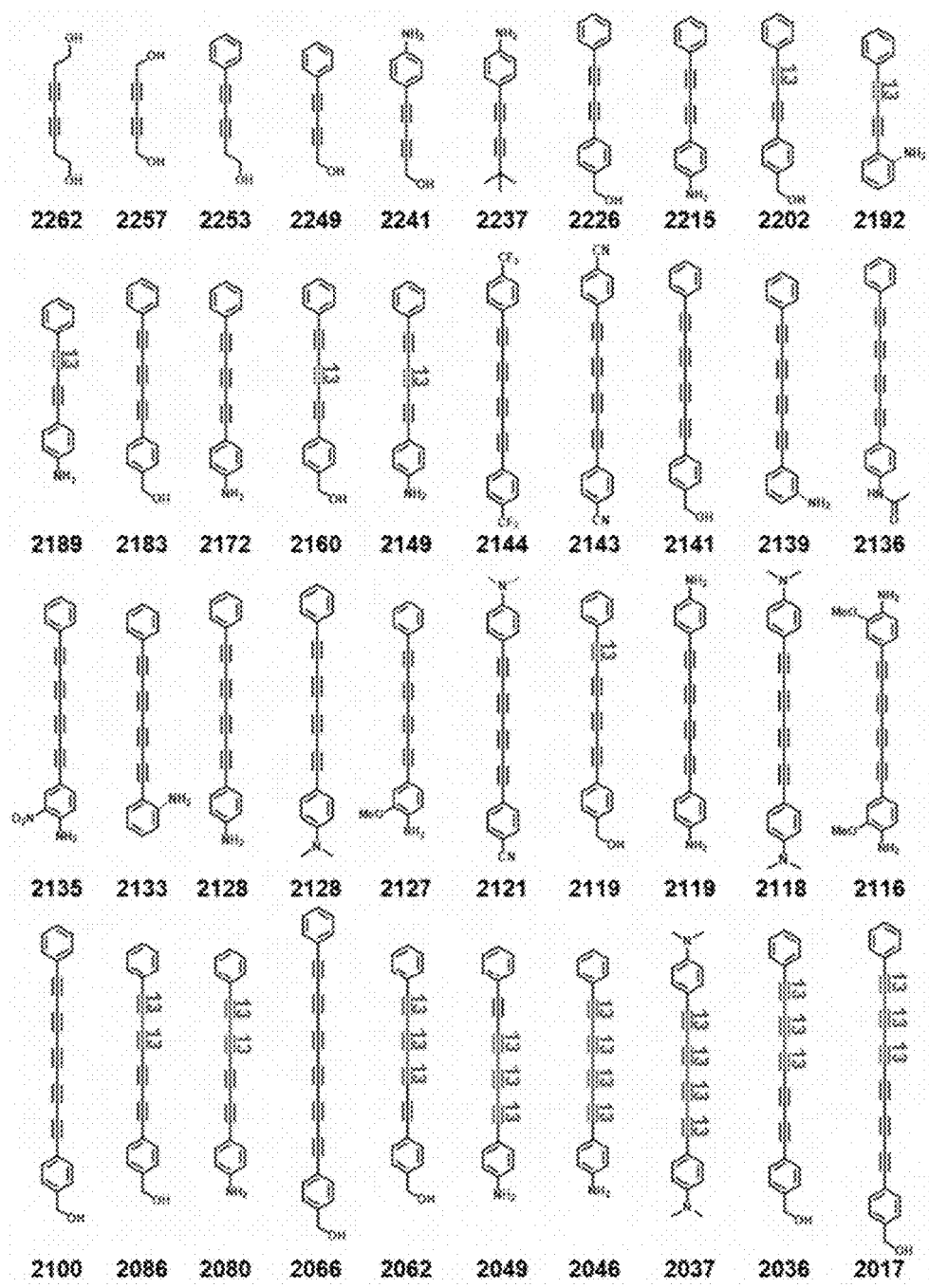
FIG. 7 is frequency exploration of polyynes through conjugation elongation, end-capping variations, and isotope doping. 40 structures are synthesized and shown with Raman frequencies (in cm-1) measured in DMSO.

Out of over 40 molecules explored for frequency super-multiplexing (FIG. 7), 20 structures with distinct Raman frequencies (termed "Carbon RainbO" or "Carbow") are obtained based on the unified carbon-atom wire scaffold (FIG. 3a), representing the largest number of resolvable frequency in the Raman-silent window. For example, using alkyl instead of phenyl as additional end-capping group can blue shift further to 2,262 cm$^{-1}$. Combined with six reported Raman frequencies in the fingerprint region from commercial dyes and four commonly available fluorescent channels, 30 colors are resolvable, which, to our knowledge, is the highest reported for parallel optical detection. Compared to 14 MARS dyes recently reported in this range, Carbow peaks are more evenly spaced and well resolved with substantially less cross-talk. For instance, the spectral separation of the closest Carbow peaks nearly doubles that in the MARS dyes.

The multiplexing capability of Carbow is useful in biological imaging for the simultaneous visualization of multiple species. We first characterized the detection sensitivity of Carbow using stimulated Raman scattering (SRS) microscopy with ultrahigh sensitivity and specificity. As low as 630 nM of a 4-yne at a signal-to-noise ratio of 1 with a 1-ms time constant (<5 µM for most polyynes) under can be detected under an SRS microscope (FIG. 4a). This is nearly 500 times more sensitive than previous SRS detection of a single alkyne tag.

Given the sub-µM sensitivity, immunostaining of specific proteins by conjugating polyynes to secondary antibodies for SRS imaging was demonstrated (see, e.g., FIG. 4b). The pattern of α-tubulin filament structures was visualized with good contrast. Tuning the wavelength away by 3 nm shows negligible background signal in the off-resonance channel. Such a sharp spectral feature is difficult to achieve for fluorescence approaches. Thus, Carbow is fully compatible with standard immunostaining procedures for protein-specific imaging. Similarly, if labeled with different antibodies, polyynes will have great potential in cell sorting with combined use of flow cytometry. For example, normal cells and cancer cells can be easily separated due to their distinct protein types on the surfaces. One of ordinary skill will understand how to conjugate antibodies and carbon atom wires, how to conduct labelling of live cells extracted from a patient with antibody-carbon atom wire conjugates, and how to conduct flow cytometry of the labelled sample.

Figure 8:
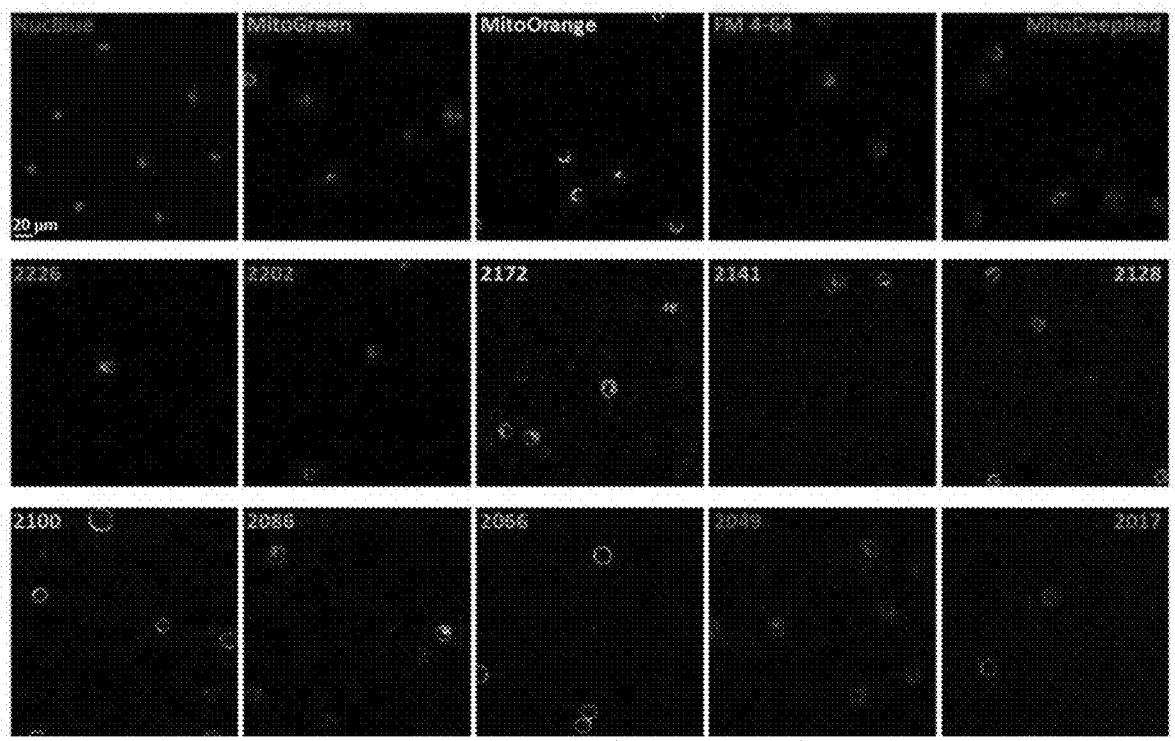
FIG. 8 is 15-color imaging of live cells with super-multiplexed polyynes. Individual channel of 5 fluorescent dyes and 10 polyynes with well-resolved frequencies are shown with little crosstalk. Simple unmixing is performed by subtracting the adjacent channel, without the need of complicated matrix unmixing.

Exemplary 15-color imaging of spatially-resolved living cells was demonstrated (FIG. 4c) each of which is singularly stained with 1 of 15 colors (five fluorescent and ten Carbow molecules). All cells can be identified individually and unequivocally from the mixture in one 15-channel image without the need of complicated unmixing (FIG. 8). Such resolvability would be challenging for fluorescence imaging with broad and overlapping spectra and for MARS dyes, which require a predetermined matrix for spectral unmixing owing to substantial cross-talk between channels. Therefore, Carbow molecules facilitate optical imaging at a degree of multiplexing that is rarely reported for live cells with straightforward detection and analysis.

Figure 10:
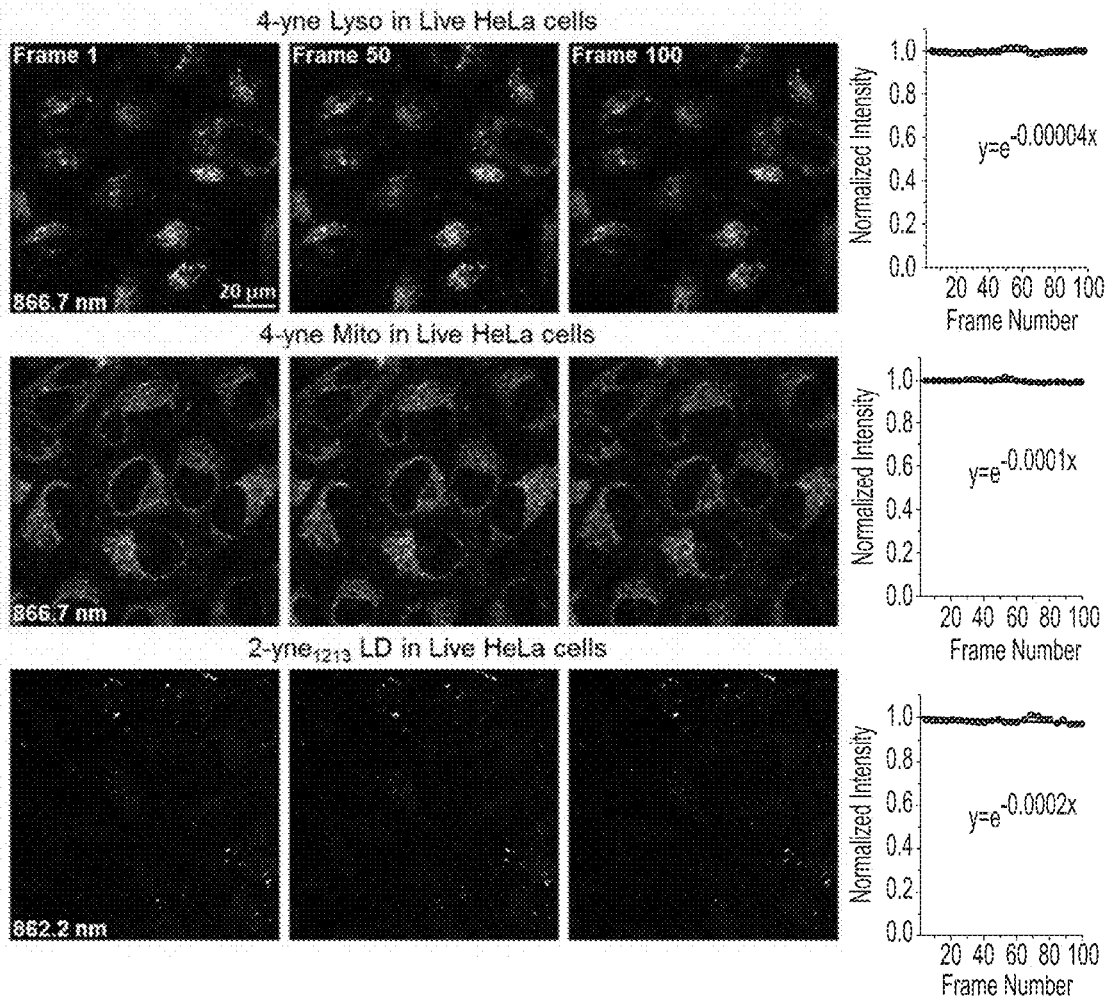
FIG. 10 is excellent photostability of polyynes in live cell imaging. HeLa cells are incubated with 2 μM 4-yne Lyso for 1 h, 4 μM 4-yne Mito for 1 h or 10 μM 2-yne1213 LD for overnight. Cells are continuously imaged for 100 frames with nearly identical intensity, and the intensity trace shows minimal decay (<2%)

Further, owing to their neutral scaffold and high membrane permeability, Carbow molecules can be functionalized into live-cell, organelle-specific imaging probes. Through a carbamate linker on the phenyl ring, different targeting groups were introduced (FIGS. 4d-h). Triphenylphosphonium (TPP+) is a motif with high affinity to mitochondrial matrix due to the positive charge. TPP+ attached 4-yne (Carbow2141 Mito) shows specific localization to mitochondria (FIG. 4d). Lysosome lumen is acidic, where basic units are protonated and trapped inside, and thus we used a dimethylamine group to target Carbow2141 into lysosomes (Carbow2141 Lyso, FIG. 4e). Similarly, a cationic diammonium group in Carbow2141 PM is used to stain the plasma membrane through interaction with anionic phosphate headgroups. Furthermore, a pentafluorobenzamide group is used with ethylene glycol chain in Carbow2226 ER to target the endoplasmic reticulum (FIG. 4f, g). Lastly, a carboxylate-terminated C12 alkyl chain is attached to Carbow2202 (Carbow2202 LD) to mimic fatty acids, and this probe is incorporated efficiently into lipid droplets (FIG. 4h). All five imaging probes show colocalized patterns with the corresponding fluorescent markers in live cells (FIG. 9). Carbow probes also exhibit high photostability (>98%) after 100 continuous frames (FIG. 10) and little cytotoxicity (FIG. 11).

Five organelle-targeted Carbow probes and five fluorescent reporters were combined to achieve tandem ten-color optical imaging of subcellular structures in live cells (FIG. 4i), which including plasma membrane, endoplasmic reticulum, Golgi, mitochondria, lysosome, lipid droplets, nucleus, tubulin and actin). Recognizing the essential roles of the organelle interactome in cellular activities, up to six-color organelle imaging has recently been achieved by fluorescence microscopy with spectral unmixing and color compensation. Ten-color organelle imaging in live cells is achieved without any unmixing or color compensation in image processing, which is difficult to achieve by other means. This is the highest degree of multiplexing demonstrated for multitarget imaging inside living cells and relies critically on Carbow's well-resolved frequencies and live-cell compatibility.

SYNTHETIC EXAMPLES

Materials and Methods

Example 1

All reagents and solvents were purchased from Sigma-Aldrich and Fisher Scientific and were used without further purification, unless otherwise stated. Flash chromatography was performed on silica gel (Silicycle, 40-63 μm). TLC was performed on 5 mm E. Merck silica plates (60F-254) and visualized by UV light or potassium permanganate (KMnO$_4$) or ceric ammonium molybdate (CAM) stain.

Nuclear magnetic resonance (NMR) spectra were recorded on a Bruker 500 (500 MHz) Bruker 400 (400 MHz) Fourier Transform (FT) NMR spectrometers at Columbia University, Chemistry Department. NMR spectra were calibrated using residual undeuterated solvent ($^1$H: δ 7.26 for CDCl$_3$, δ 3.31 for MeOH-d$_4$, δ 2.50 for DMSO-d$_6$; $^{13}$C: δ 77.16 for CDCl$_3$, δ 49.0 for MeOH-d$_4$, δ 39.50 for DMSO-d$_6$). The following abbreviations were used to explain multiplicities: s=singlet, d=doublet, t=triplet, q=quartet, m=multiplet, br=broad. High resolution mass spectra (HRMS) were recorded on a XEVO G2-XS Waters mass spectrometer equipped with a QTOF detector with multiple inlet and ionization capabilities. UV-Vis absorption spectra were measured on a Tecan infinite 200 using 96-well plates.

Synthesis of Carbow Diynes

Carbow2226

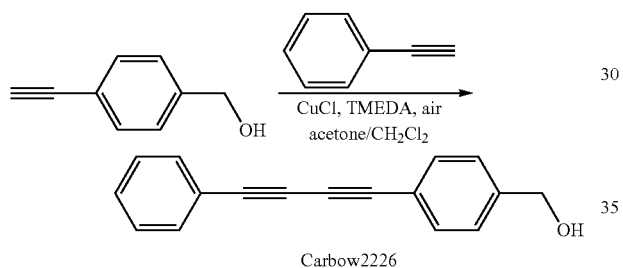

Carbow2226

A solution of CuCl (100 mg, 1.0 mmol) and TMEDA (300 μL, 2.0 mmol) in acetone (5 ml) was bubbled with air for 10 mins at rt, then a mixture of 4-ethynylbenzyl alcohol (264 mg, 2.0 mmol) and phenylacetylene (0.66 ml, 6.0 mmol) in CH2Cl2 (3 ml) were added and continued to stirred with air at rt for 2 h. The solvent was evaporated at reduced pressure and the residue was subjected to chromatography to obtain Carbow2226 (312 mg, 67%) as a white solid. $^1$H NMR (400 MHz; CDCl$_3$): δ 7.55-7.50 (m, 4H), 7.40-7.30 (m, 5H), 4.69 (s, 2H), 1.92 (br, 1H); $^{13}$C NMR (100 MHz, CDCl3): δ 142.2, 132.8, 132.6, 129.3, 128.6, 126.9, 121.9, 121.0, 81.7, 81.5, 74.1, 74.0, 64.9; HRMS (ASAP): calcd for C$_{17}$H$_{12}$O+ [M]$^+$ 232.0888, found 232.0889.

The other Carbow diynes were prepared using the same procedures as Carbow2226.

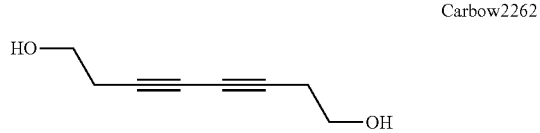

Carbow2262

$^1$H NMR (400 MHz; CDCl$_3$): δ 3.78-3.68 (m, 4H), 2.52 (t, J=6.2 Hz, 4H), 2.17 (br, 2H); $^{13}$C NMR (100 MHz, CDCl$_3$): δ 74.8, 66.9, 60.9, 23.7; HRMS (ASAP): calcd for C$_8$H$_{11}$O$_2$$^+$ [M+H]$^+$ 139.0759, found 139.0760.

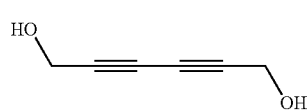

Carbow2257

$^1$H NMR (400 MHz; MeOH-d$_4$): δ 4.19 (s, 4H); $^{13}$C NMR (100 MHz, MeOH-d$_4$): δ 78.8, 69.4, 50.9; HRMS (ASAP): calcd for C$_{12}$H$_{12}$O$_4$$^+$ [2M]$^+$ 220.0736, found 220.0726.

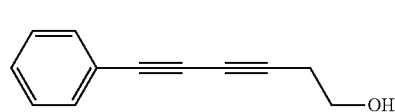

Carbow2253

$^1$H NMR (400 MHz; CDCl$_3$): δ 7.50-7.45 (m, 2H), 7.37-7.27 (m, 3H), 3.84-3.75 (m, 2H), 2.64 (t, J=6.2 Hz, 2H), 1.96 (br, 1H); $^{13}$C NMR (100 MHz, CDCl$_3$): δ 132.7, 129.2, 128.5, 121.8, 81.1, 75.5, 74.1, 66.9, 60.9, 24.1; HRMS (ASAP): calcd for C$_{12}$H$_{11}$O$^+$ [M+H]$^+$ 171.0810, found 171.0805.

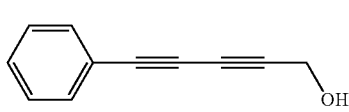

Carbow2249

$^1$H NMR (400 MHz; CDCl$_3$): δ 7.52-7.46 (m, 2H), 7.39-7.28 (m, 3H), 4.43 (s, 2H), 2.28 (br, 1H); $^{13}$C NMR (100 MHz, CDCl$_3$): δ 132.7, 129.4, 128.5, 121.5, 80.6, 78.7, 73.3, 70.5, 51.7; HRMS (ASAP): calcd for C$_{11}$H$_7$$^+$ [M-OH]$^+$ 139.0548, found 139.0565.

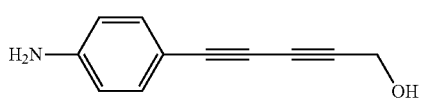

Carbow2241

$^1$H NMR (400 MHz, DMSO-d$_6$): δ 7.18 (d, J=8.4 Hz, 2H), 6.53 (d, J=8.4 Hz, 2H), 5.65 (br, 2H), 4.21 (d, J=6.0 Hz, 2H); HRMS (ASAP): calcd for C$_{11}$H$_8$N$^+$ [M-OH]$^+$ 154.0657, found 154.0664.

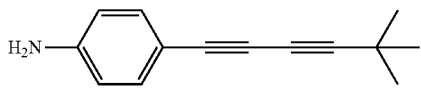

Carbow2237

$^1$H NMR (400 MHz; CDCl$_3$): δ 7.29 (d, J=8.4 Hz, 2H), 6.59 (d, J=8.4 Hz, 2H), 3.86 (br, 2H), 1.30 (s, 9H); $^{13}$C NMR (100 MHz, CDCl$_3$): δ 147.2, 134.1, 114.7, 111.3, 91.4, 72.2, 64.2, 53.5, 30.7, 28.4; HRMS (ASAP): calcd for C$_{14}$H$_{16}$N$^+$ [M+H]$^+$ 198.1283, found 198.1277.

Carbow2215

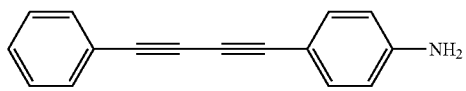

¹H NMR (400 MHz; CDCl₃): δ 7.56-7.48 (m, 2H), 7.38-7.30 (m, 5H), 6.59 (d, J=8.4 Hz, 2H), 3.89 (br, 2H); ¹³C NMR (100 MHz, CDCl₃): δ 147.7, 134.2, 132.5, 128.9, 128.5, 122.3, 114.7, 110.7, 82.9, 80.9, 74.6, 72.2; HRMS (ASAP): calcd for $C_{16}H_{12}N^+$ [M+H]⁺ 218.0970, found 218.0976.

4.32 (br, 2H); ¹³C NMR (100 MHz, CDCl₃): δ 82.9 (d, J=784.8 Hz), 73.9 (d, J=784.8 Hz); HRMS (ASAP): calcd for $^{12}C_{14}{}^{13}C_2H_{12}N^+$ [M+H]⁺ 220.1037, found 220.1035.

Carbow2189

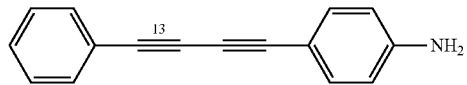

¹H NMR (400 MHz; CDCl₃): δ 7.56-7.46 (m, 2H), 7.41-7.28 (m, 5H), 6.60 (d, J=8.4 Hz, 2H), 3.89 (br, 2H); ¹³C NMR (100 MHz, CDCl₃): δ 81.0 (d, J=782.8 Hz), 74.4 (d, J=782.8 Hz); HRMS (ASAP): calcd for $^{12}C_{14}{}^{13}C_2H_{12}N^+$ [M+H]⁺ 220.1037, found 220.1038.

Synthesis of Carbow Trivynes
Carbow2183

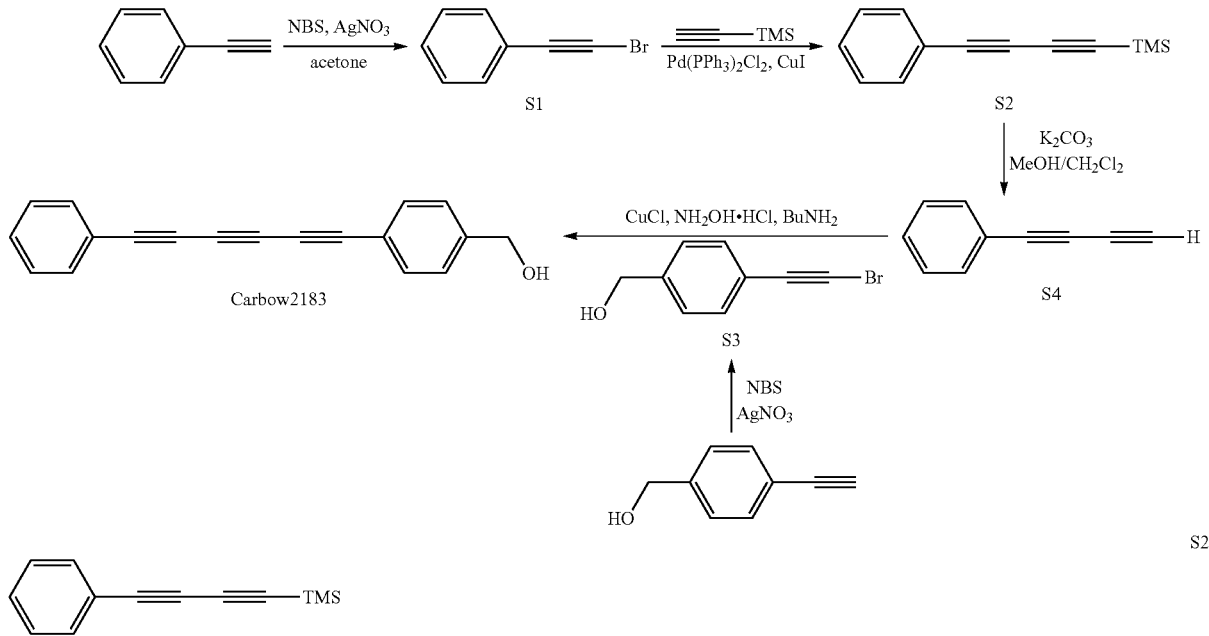

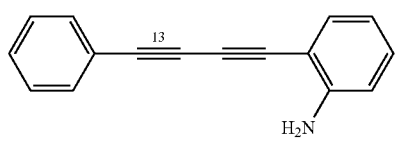

Carbow2202

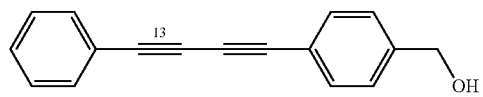

¹H NMR (500 MHz, CDCl₃): δ 7.60-7.45 (m, 4H), 7.43-7.27 (m, 5H), 4.72 (s, 2H); HRMS (ASAP): calcd for $^{12}C_{15}{}^{13}C_2H_{12}O$ [M]⁺ 234.0955, found 234.0952.

Carbow2192

¹H NMR (400 MHz; CDCl₃): δ 7.58-7.49 (m, 2H), 7.40-7.31 (m, 4H), 7.19-7.13 (m, 1H), 6.72-6.66 (m, 2H),

To a solution of phenylacetylene (1.32 mL, 12.0 mmol) in acetone (40 ml) was added N-bromosuccinimide (2.24 g, 12.6 mmol) and AgNO₃ (204 mg, 1.2 mmol). The reaction mixture was stirred 2 h at rt. Then, the mixture was filtered under reduced pressure, and the filtrate was poured into H₂O (50 mL). The product mixture was extracted with petroleum ether (3×30 mL). The combined organic layer was washed with brine and dried over MgSO₄, The solvent was concentrated under reduced pressure, and the residue was purified by column chromatography to afford the phenylacetylene bromide product S1 as a colorless liquid.

A mixture of the above phenylacetylene bromide S1 (2.09 g, 11.6 mmol), CuI (66.4 mg, 0.35 mmol), and Pd(PPh₃)₂Cl₂ (0.24 g, 0.35 mmol) in a 100 mL three-neck flask was degassed and refilled with N₂. After this procedure was repeated three times, triethylamine (55 mL) and (trimethylsilyl)acetylene (2.45 mL, 17.4 mmol) were added with syringe. The reaction solution was stirred at 50° C. for 2 h, then the solvent was evaporated under reduced pressure, and the residue was further purified by column chromatography with petrol ether as the eluent to afford S2 (1.47 g, 64%) as a yellow liquid.

$^1$H NMR (400 MHz, CDCl$_3$): δ 7.52-7.48 (m, 2H), 7.40-7.30 (m, 3H), 0.25 (s, 9H); $^{13}$C NMR (100 MHz, CDCl$_3$): δ 132.8, 129.4, 128.5, 121.6, 90.8, 88.0, 76.9, 74.3, −0.2; HRMS (ASAP): calcd for C$_{13}$H$_{14}$Si$^+$ [M]$^+$ 198.0865, found 198.0873.

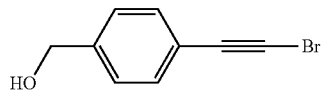

S3

To a solution of 4-ethynylbenzyl alcohol (132 mg, 1.0 mmol) in acetone (8 ml) was added N-bromosuccinimide (187 mg, 1.05 mmol) and AgNO$_3$ (17.2 mg, 0.10 mmol). The reaction mixture was stirred 3 h at rt. Then, the mixture was filtered under reduced pressure, and the filtrate was poured into H$_2$O (10 mL). The product mixture was extracted with ethyl ether (3×10 mL). The combined organic layer was washed with brine, dried over MgSO$_4$, and concentrated under reduced pressure. The resulting residue was purified by flash chromatography to obtain compound S3 (177 mg, 84%) as a white solid.

$^1$H NMR (400 MHz, CDCl$_3$): δ 7.43 (d, J=8.0 Hz, 2H), 7.29 (d, J=8.0 Hz, 2H), 4.67 (s, 2H), 1.92 (br, 1H); $^{13}$C NMR (100 MHz, CDCl$_3$): δ 141.6, 132.3, 126.9, 122.0, 80.0, 64.9, 49.9; HRMS (ASAP): calcd for C$_9$H$_6$Br$^+$ [M-OH]$^+$ 192.9653, found 192.9658.

Carbow2183

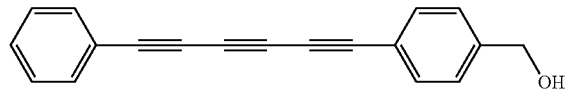

To a solution of S2 (30 mg, 0.15 mmol) in CH$_2$Cl$_2$-MeOH (1:1, 2 mL) was added K$_2$CO$_3$ (83 mg, 0.60 mmol). After the mixture was stirred at room temperature for 1 h, H$_2$O was added and the mixture was extracted with ether. The organic phase was dried over Na$_2$SO$_4$ and the solvent was evaporated under reduced pressure. The residue S4 was diluted with toluene (2 mL) and cooled to 0° C. CuCl (5.2 mg, 0.05 mmol), NH$_2$OH·HCl (7.0 mg, 0.10 mmol) and BuNH$_2$ (60 μL, 0.6 mmol) were added in order. Alkynyl bromide S3 (32 mg, 0.15 mmol) was diluted with 1 mL toluene and was added dropwise to the mixture. The reaction mixture was allowed to warm to room temperature and stirred for 10 h. The reaction was quenched with H$_2$O and extracted with ether. The organic layer was washed with H$_2$O and dried with MgSO$_4$. After the solvent was removed by rotovap, the product was purified by column chromatograph on silica to obtain Carbow2183 (21 mg, 54%) as a yellow solid.

$^1$H NMR (400 MHz, CDCl$_3$): δ 7.58-7.48 (m, 4H), 7.43-7.37 (m, 1H), 7.37-7.30 (m, 4H), 4.72 (s, 2H); $^{13}$C NMR (100 MHz, CDCl$_3$): δ 142.6, 133.2, 133.0, 129.7, 128.5, 126.8, 121.0, 120.1, 78.6, 78.5, 74.5, 74.4, 66.5, 66.5, 64.8; HRMS (ASAP): calcd for C$_{19}$H$_{12}$O$^+$ [M]$^+$ 256.0888, found 256.0895.

The other Carbow triynes were prepared using the same procedures as Carbow2183.

Carbow2172

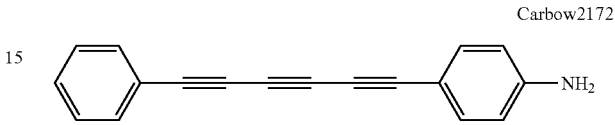

$^1$H NMR (400 MHz; CDCl$_3$): δ 7.55-7.50 (m, 2H), 7.40-7.30 (m, 5H), 6.58 (d, J=8.4 Hz, 2H), 3.95 (br, 2H); $^{13}$C NMR (100 MHz, CDCl$_3$): δ 148.1, 134.8, 133.0, 129.6, 128.6, 121.4, 114.7, 109.7, 80.1, 78.4, 74.9, 72.9, 67.4, 65.9; HRMS (ASAP): calcd for C$_{18}$H$_{11}$N$^+$ [M]$^+$ 241.0891, found 241.0876.

Carbow2160

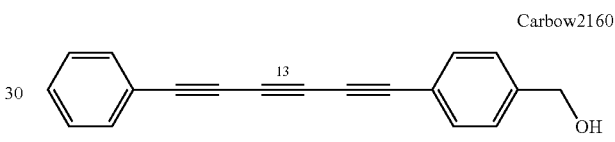

$^1$H NMR (500 MHz, CDCl$_3$): δ 7.56-7.50 (m, 4H), 7.42-7.30 (m, 5H), 4.72 (s, 2H); $^{13}$C NMR (125 MHz, CDCl$_3$): δ 66.6; HRMS (ASAP): calcd for $^{12}$C$_{17}$$^{13}$C$_2$H$_{12}$O [M]$^+$ 258.0955, found 258.0946.

Carbow2149

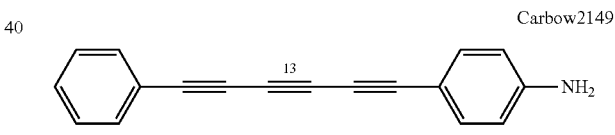

$^1$H NMR (400 MHz; CDCl$_3$): δ 7.56-7.50 (m, 2H), 7.41-7.29 (m, 5H), 6.58 (d, J=8.4 Hz, 2H), 3.95 (br, 2H); $^{13}$C NMR (100 MHz, CDCl$_3$): δ 66.8, 66.4; HRMS (ASAP): calcd for $^{12}$C$_{16}$$^{13}$C$_2$H$_{11}$N$^+$ [M]$^+$ 243.0959, found 243.0952.

Synthesis of Carbow Tetraynes

Carbow2141

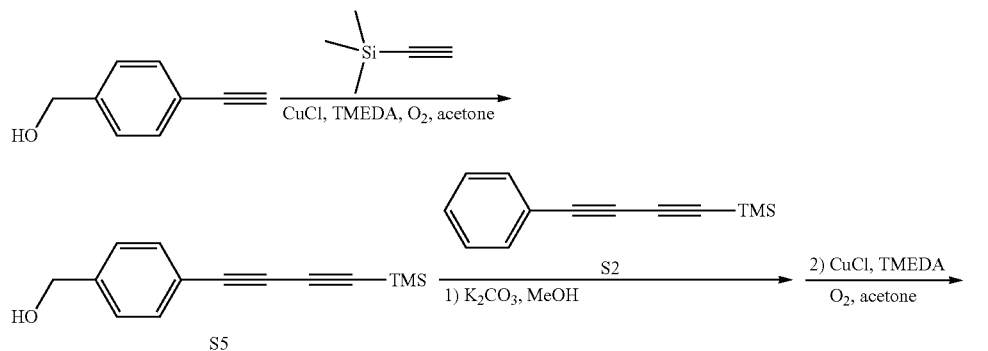

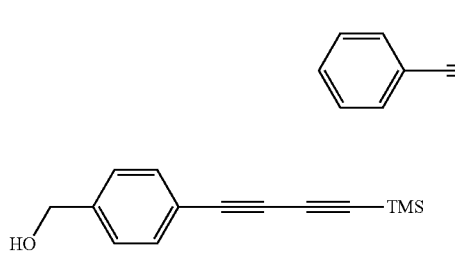

Carbow2141

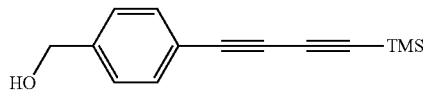

S5

A solution of CuCl (120 mg, 1.2 mmol) and TMEDA (360 μL, 2.4 mmol) in acetone (7 ml) was bubbled with air for 10 mins at rt, then the mixture of (trimethylsilyl)acetylene (1.01 mL, 7.2 mmol) and 4-ethynylbenzyl alcohol (317 mg, 2.4 mmol) in $CH_2Cl_2$ were added and continued to stirred with air at rt for 2 h, then concentrated at reduced pressure. The residue was subjected to chromatography to give compound S5 (339 mg, 62%) as a yellow solid.

$^1$H NMR (400 MHz; $CDCl_3$): δ 7.47 (d, J=8.0 Hz, 2H), 7.30 (d, J=8.0 Hz, 2H), 4.67 (s, 2H), 1.95 (br, 1H), 0.23 (s, 9H); $^{13}$C NMR (100 MHz, $CDCl_3$): δ 142.3, 132.9, 126.9, 120.6, 90.8, 87.9, 76.7, 74.3, 64.8, −0.3; HRMS (ASAP): calcd for $C_{14}H_{15}Si^+$ [M−OH]$^+$ 211.0943, found 211.1019.

Carbow2141

To a solution of S5 (100 mg, 0.44 mmol) and S2 (130 mg, 0.66 mmol) in $CH_2Cl_2$-MeOH (1:1, 6 mL) was added $K_2CO_3$ (243 mg, 1.76 mmol). After the mixture was stirred at room temperature for 1 h, $H_2O$ was added and the mixture was extracted with ether. The organic phase was dried over $Na_2SO_4$ and the solvent was evaporated under reduced pressure. The residue was used directly for next step.

A solution of CuCl (44 mg, 0.44 mmol) and TMEDA (132 μL, 0.88 mmol) in acetone (5 ml) was bubbled with air for 10 mins at rt, then the above mixture in $CH_2Cl_2$ were added and continued to stirred with air at rt for 1 h, then concentrated at reduced pressure and purified by flash chromatography to obtain Carbow2141 (64 mg, 52%) as a yellow solid.

$^1$H NMR (400 MHz, $CDCl_3$): δ 7.56-7.51 (m, 4H), 7.44-7.38 (m, 1H), 7.37-7.31 (m, 4H), 4.72 (s, 2H), 1.78 (br, 1H); $^{13}$C NMR (100 MHz, $CDCl_3$): δ 143.1, 133.5, 133.3, 130.1, 128.7, 126.9, 120.7, 119.8, 77.9, 77.7, 74.6, 74.5, 67.4, 67.3, 64.9, 63.9, 63.8; HRMS (ASAP): calcd for $C_{21}H_{12}O^+$ [M]$^+$ 280.0888, found 280.0876.

The other Carbow tetraynes were prepared using the same procedures as Carbow2141.

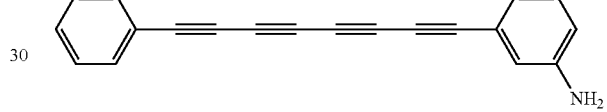

Carbow2144

$^1$H NMR (400 MHz, $CDCl_3$): δ 7.74-7.53 (m, 8H); $^{13}$C NMR (100 MHz, $CDCl_3$): δ 133.4, 131.6 (d, J=32.8 Hz), 125.5 (q, J=3.8 Hz), 124.3, 123.6 (d, J=272.3 Hz), 76.3, 76.2, 68.0, 63.6; HRMS (ASAP): calcd for $C_{22}H_8F_6^+$ [M]$^+$ 386.0532, found 386.0542.

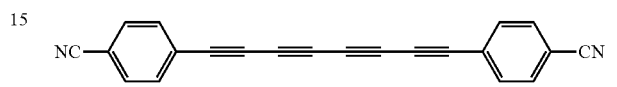

Carbow2143

$^1$H NMR (400 MHz, $CDCl_3$): δ 7.72 (d, J=8.0 Hz, 4H), 7.69 (d, J=8.0 Hz, 4H); $^{13}$C NMR (100 MHz, $CDCl_3$): δ 133.8, 132.5, 127.0, 118.1, 111.2, 78.3, 75.3, 68.7, 63.57; HRMS (ASAP): calcd for $C_{22}H_9N_2^+$ [M+H]$^+$ 301.0766, found 301.0757.

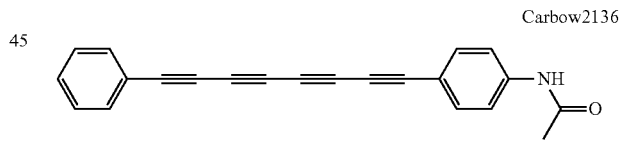

Carbow2139

$^1$H NMR (400 MHz, $CDCl_3$): δ 7.58-7.50 (m, 2H), 7.45-7.38 (m, 1H), 7.38-7.31 (m, 2H), 7.12 (t, J=7.9 Hz, 1H), 6.95 (d, J=7.6 Hz, 1H), 6.83 (t, J=1.9 Hz, 1H), 6.72 (dd, J=8.0, 2.4 Hz, 1H), 3.74 (s, 2H); $^{13}$C NMR (100 MHz, $CDCl_3$): δ 146.4, 133.2, 130.0, 129.5, 128.6, 123.7, 121.1, 120.5, 118.8, 117.1, 78.1, 77.6, 74.5, 73.8, 67.3, 66.9, 63.8, 63.5; HRMS (ASAP): calcd for $C_{20}H_{12}N^+$ [M+H]$^+$ 266.0970, found 266.0974.

Carbow2136

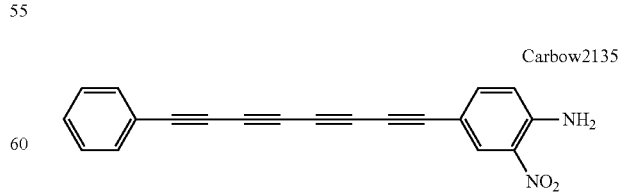

$^1$H NMR (400 MHz, $CDCl_3$): δ 7.57-7.52 (m, 2H), 7.51 (s, 3H), 7.43-7.38 (m, 1H), 7.38-7.32 (m, 2H), 7.21 (s, 1H), 2.20 (s, 3H); HRMS (ASAP): calcd for $C_{22}H_{14}NO^+$ [M+H]$^+$ 308.1075, found 308.1073.

Carbow2135

$^1$H NMR (400 MHz, $CDCl_3$): δ 8.36 (s, 1H), 7.54 (d, J=7.5 Hz, 2H), 7.50-7.30 (m, 4H), 6.77 (d, J=8.6 Hz, 1H), 6.35 (s, 2H); $^{13}$C NMR (100 MHz, $CDCl_3$): δ 145.2, 139.0, 133.2, 132.0, 130.0, 128.6, 120.5, 119.1, 108.9, 77.9, 76.1,

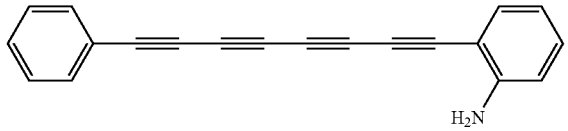

Carbow2133

$^1$H NMR (400 MHz, CDCl$_3$): δ 7.55 (d, J=7.5 Hz, 2H), 7.47-7.29 (m, 4H), 7.19 (t, J=7.7 Hz, 1H), 6.68 (t, J=7.7 Hz, 2H), 4.36 (s, 2H); $^{13}$C NMR (100 MHz, CDCl$_3$): δ 150.9, 133.8, 133.2, 131.5, 130.0, 128.6, 120.6, 118.1, 114.5, 104.5, 79.7, 78.1, 75.2, 74.5, 68.8, 67.2, 64.6, 63.6; HRMS (ASAP): calcd for C$_{20}$H$_{12}$N$^+$ [M+H]$^+$ 266.0970, found 266.0972.

74.4, 74.1, 67.4, 67.2, 63.9, 63.6; HRMS (ASAP): calcd for C$_{20}$H$_{11}$N$_2$O$_2^+$ [M+H]$^+$ 311.0821, found 311.0815.

$^1$H NMR (400 MHz, CDCl$_3$): δ 7.65-7.59 (m, 4H), 7.44 (d, J=8.4 Hz, 2H), 6.61 (d, J=8.4 Hz, 2H), 3.04 (s, 6H); HRMS (ASAP): calcd for C$_{23}$H$_{15}$N$_2^+$ [M+H]$^+$ 319.1235, found 319.1239.

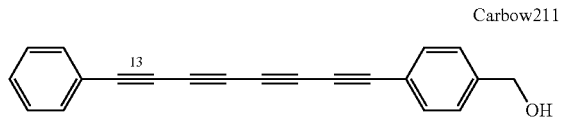

Carbow2119

$^1$H NMR (400 MHz, CDCl$_3$): δ 7.57-7.50 (m, 4H), 7.44-7.38 (m, 1H), 7.37-7.31 (m, 4H), 4.72 (s, 2H), 1.73 (br, 1H); $^{13}$C NMR (100 MHz, CDCl$_3$): δ 78.1 (d, J=786.0 Hz), 74.3 (d, J=786.0 Hz); HRMS (ASAP): calcd for $^{12}$C$_{19}$$^{13}$C$_2$H$_{12}$O [M]$^+$ 282.0955, found 282.0951.

Carbow2128

$^1$H NMR (400 MHz, CDCl$_3$): δ 7.60-7.47 (m, 2H), 7.45-7.28 (m, 5H), 6.58 (d, J=8.4 Hz, 2H), 3.99 (br, 2H); $^{13}$C NMR (100 MHz, CDCl$_3$): δ 148.3, 135.0, 133.1, 129.8, 128.5, 120.8, 114.6, 108.9, 79.3, 77.5, 74.6, 73.0, 67.6, 66.8, 64.5, 63.5; HRMS (ASAP): calcd for C$_{20}$H$_{12}$N$^+$ [M+H]$^+$ 266.0970, found 266.0974.

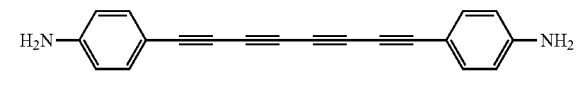

Carbow2119'

$^1$H NMR (500 MHz, MeOH-d$_4$): δ 7.20 (d, J=8.5 Hz, 4H), 6.61 (d, J=8.5 Hz, 4H); HRMS (ASAP): calcd for C$_{20}$H$_{13}$N$_2^+$ [M+H]$^+$ 281.1079, found 281.1080.

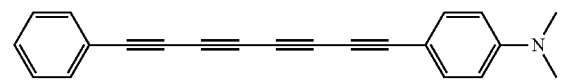

Carbow2128'

$^1$H NMR (400 MHz, CDCl$_3$): δ 7.58-7.48 (m, 2H), 7.47-7.29 (m, 5H), 6.64-6.53 (m, 2H), 3.02 (s, 6H); HRMS (ASAP): calcd for C$_{22}$H$_{16}$N$^+$ [M+H]$^+$ 294.1283, found 294.1276.

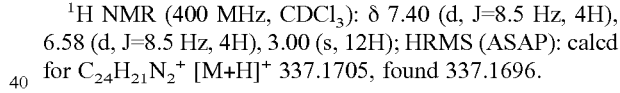

Carbow2118

$^1$H NMR (400 MHz, CDCl$_3$): δ 7.40 (d, J=8.5 Hz, 4H), 6.58 (d, J=8.5 Hz, 4H), 3.00 (s, 12H); HRMS (ASAP): calcd for C$_{24}$H$_{21}$N$_2^+$ [M+H]$^+$ 337.1705, found 337.1696.

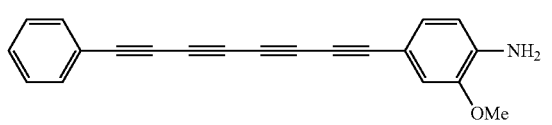

Carbow2127

$^1$H NMR (400 MHz, CDCl$_3$): δ 7.53 (d, J=7.4 Hz, 2H), 7.46-7.30 (m, 3H), 7.05 (d, J=8.0 Hz, 1H), 6.92 (s, 1H), 6.59 (d, J=8.1 Hz, 1H), 4.16 (s, 2H), 3.85 (s, 3H); HRMS (ASAP): calcd for C$_{21}$H$_{14}$NO$^+$ [M+H]$^+$ 296.1075, found 296.1071.

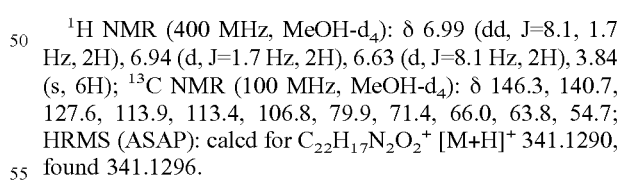

Carbow2116

$^1$H NMR (400 MHz, MeOH-d$_4$): δ 6.99 (dd, J=8.1, 1.7 Hz, 2H), 6.94 (d, J=1.7 Hz, 2H), 6.63 (d, J=8.1 Hz, 2H), 3.84 (s, 6H); $^{13}$C NMR (100 MHz, MeOH-d$_4$): δ 146.3, 140.7, 127.6, 113.9, 113.4, 106.8, 79.9, 71.4, 66.0, 63.8, 54.7; HRMS (ASAP): calcd for C$_{22}$H$_{17}$N$_2$O$_2^+$ [M+H]$^+$ 341.1290, found 341.1296.

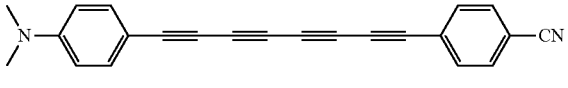

Carbow2121

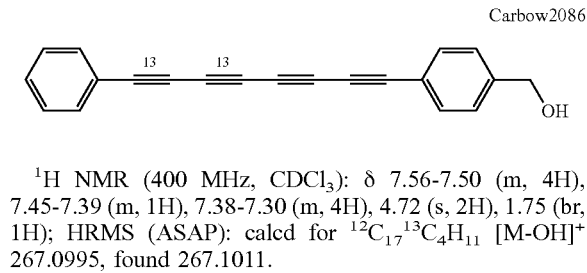

Carbow2086

$^1$H NMR (400 MHz, CDCl$_3$): δ 7.56-7.50 (m, 4H), 7.45-7.39 (m, 1H), 7.38-7.30 (m, 4H), 4.72 (s, 2H), 1.75 (br, 1H); HRMS (ASAP): calcd for $^{12}$C$_{17}$$^{13}$C$_4$H$_{11}$ [M-OH]$^+$ 267.0995, found 267.1011.

Carbow2080

¹H NMR (400 MHz, CDCl₃): δ 7.61-7.47 (m, 2H), 7.45-7.29 (m, 5H), 6.65-6.51 (m, 2H), 3.98 (br, 2H); HRMS (ASAP): calcd for $^{12}C_{14}{}^{13}C_6H_{11}N^+$ [M]⁺ 271.1093, found 271.1093.

Carbow2062

¹H NMR (400 MHz, CDCl₃): δ 7.56-7.50 (m, 4H), 7.44-7.39 (m, 1H), 7.38-7.31 (m, 4H), 4.72 (s, 2H), 1.73 (br, 1H); HRMS (ASAP): calcd for $^{12}C_{15}{}^{13}C_6H_{11}$ [M-OH]⁺ 269.1062, found 269.1116.

Carbow2049

¹H NMR (400 MHz, CDCl₃): δ 7.53 (d, J=8.0 Hz, 2H), 7.42-7.30 (m, 5H), 6.58 (d, J=8.0 Hz, 2H), 3.97 (br, 2H); HRMS (ASAP): calcd for $^{12}C_{14}{}^{13}C_6H_{11}N^+$ [M]⁺ 271.1093, found 271.1093.

Carbow2046

¹H NMR (400 MHz, CDCl₃): δ 7.53 (d, J=8.0 Hz, 2H), 7.42-7.32 (m, 5H), 6.58 (d, J=8.0 Hz, 2H), 3.97 (br, 2H); HRMS (ASAP): calcd for $^{12}C_{12}{}^{13}C_8H_{12}N^+$ [M+H]⁺ 274.1238, found 274.1222.

Carbow2037

¹H NMR (400 MHz, CDCl₃): δ 7.40 (dd, J=8.8, 4.9 Hz, 4H), 6.59 (d, J=8.8 Hz, 4H), 3.01 (s, 12H); HRMS (ASAP): calcd for $^{12}C_{16}{}^{13}C_8H_{21}N_2^+$ [M+H]⁺ 345.1968, found 345.1971.

Synthesis of Carbow Pentaynes

Carbow2100

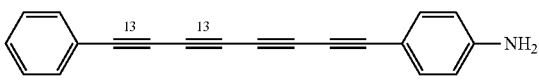

To a solution of S2 (48 mg, 0.24 mmol) in acetonitrile with an addition of H$_2$O (18 μL, 1.0 mmol) was added AgF (30 mg, 0.24 mmol), and the mixture was stirred for 20 min. Next N-bromosuccinimide (51 mg, 0.28 mmol) was introduced, and the mixture was stirred for 3 h. Acetonitrile was removed under reduced pressure and the residue was diluted with ethyl ether. The organic layer was washed with H$_2$O and dried with MgSO$_4$. The solvent was removed and the residue was further purified by column chromatography to give the pure product S6.

A mixture of S6, CuI (4.4 mg, 0.024 mmol), and Pd(PPh$_3$)$_2$Cl$_2$ (16.8 mg, 0.024 mmol) in a three-neck flask was degassed and refilled with N$_2$. After this procedure was repeated three times, triethylamine (5 mL) and (trimethylsilyl)acetylene (47 mg, 0.48 mmol) were added with syringe. The reaction solution was stirred at 50° C. for 2 h, then the solvent was evaporated under reduced pressure, and the residue was further purified by column chromatography with petrol ether as the eluent to afford S7 (36 mg, 67%) as a yellow liquid.

$^1$H NMR (400 MHz, CDCl$_3$): δ 7.54-7.49 (m, 2H), 7.42-7.36 (m, 1H), 7.36-7.29 (m, 2H), 0.23 (s, 9H); $^{13}$C NMR (100 MHz, CDCl$_3$): δ 133.1, 129.8, 128.5, 120.8, 89.0, 88.1, 76.9, 74.3, 66.8, 61.6, −0.5; HRMS (ASAP): calcd for C$_{15}$H$_{14}$Si$^+$ [M]$^+$ 222.0865, found 222.0843.

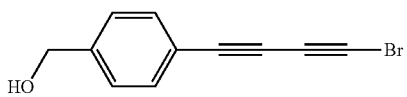

S9

To a solution of S5 (32 mg, 0.14 mmol) in acetonitrile with an addition of H$_2$O (18 μL, 1.0 mmol) was added AgF (18 mg, 0.14 mmol), and the mixture was stirred for 20 min. Next N-bromosuccinimide (29 mg, 0.16 mmol) was added, and the mixture was stirred for 5 h. Acetonitrile was removed under reduced pressure and the residue was diluted with ethyl ether. The organic layer was washed with H$_2$O, brine and dried with MgSO$_4$. The solvent was removed and the residue was further purified by column chromatography to give S9 (24 mg, 73%).

$^1$H NMR (400 MHz, CDCl$_3$): δ 7.49 (d, J=8.3 Hz, 2H), 7.31 (d, J=8.0 Hz, 2H), 4.69 (s, 2H); $^{13}$C NMR (100 MHz, CDCl$_3$): δ 142.4, 133.0, 126.8, 120.2, 74.3, 73.9, 65.4, 64.8, 44.5; HRMS (ASAP): calcd for C$_{11}$H$_6$Br$^+$ [M-OH]$^+$: 216.9653, found: 216.9661.

Carbow2100

To a solution of S7 (11 mg, 0.05 mmol) in CH$_2$Cl$_2$-MeOH (1:1, 1 mL) was added K$_2$CO$_3$ (28 mg, 0.20 mmol). After the mixture was stirred at room temperature for 1 h, H$_2$O was added and the mixture was extracted with ether. The organic phase was dried over Na$_2$SO$_4$ and the solvent was evaporated under reduced pressure. The residue S8 was diluted with toluene (1 mL) and cooled to 0° C. CuCl (5.2 mg, 0.05 mmol), NH$_2$OH·HCl (7.0 mg, 0.10 mmol) and BuNH$_2$ (60 μL, 0.6 mmol) were added in order. Alkynyl bromide 19 (12 mg, 0.05 mmol) in toluene (1 mL) was added dropwise to the mixture. The reaction mixture was allowed to warm to rt and stirred for 10 h. The reaction was quenched with H$_2$O and extracted with ether. The organic layer was washed with H$_2$O, brine and dried with MgSO$_4$. After the solvent was removed by rotovapor, the product was purified by column chromatograph on silica to obtain Carbow2100 (7.1 mg, 47%) as a yellow solid.

$^1$H NMR (400 MHz, CDCl$_3$): δ 7.60-7.46 (m, 4H), 7.45-7.38 (m, 1H), 7.38-7.28 (m, 4H), 4.73 (s, 2H); $^{13}$C NMR (100 MHz, CDCl$_3$) δ 143.2, 133.6, 133.4, 130.2, 128.6, 126.8, 120.3, 119.3, 77.5, 74.4, 74.4, 67.3, 67.3, 64.7, 64.5, 64.5, 62.8, 62.8; HRMS (ASAP): calcd for C$_{23}$H$_{12}$O$^+$ [M]$^+$: 304.0888, found: 304.0864.

Carbow2036 was prepared using the same procedures as Carbow2100.

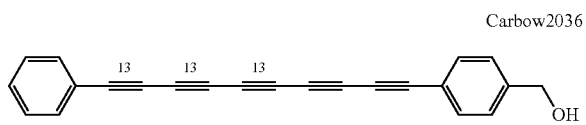 [SMILES: OCc1ccc(C#CC#CC#CC#CC#Cc2ccccc2)cc1]

Carbow2036

$^1$H NMR (400 MHz, CDCl$_3$): δ 7.58-7.47 (m, 4H), 7.45-7.37 (m, 1H), 7.36-7.29 (m, 4H), 4.72 (s, 2H); HRMS (ASAP): calcd for $^{12}$C$_{17}$$^{13}$C$_6$H$_{12}$O [M]$^+$ 310.1089, found 310.1090.

Synthesis of Hexaynes

Carbow2066

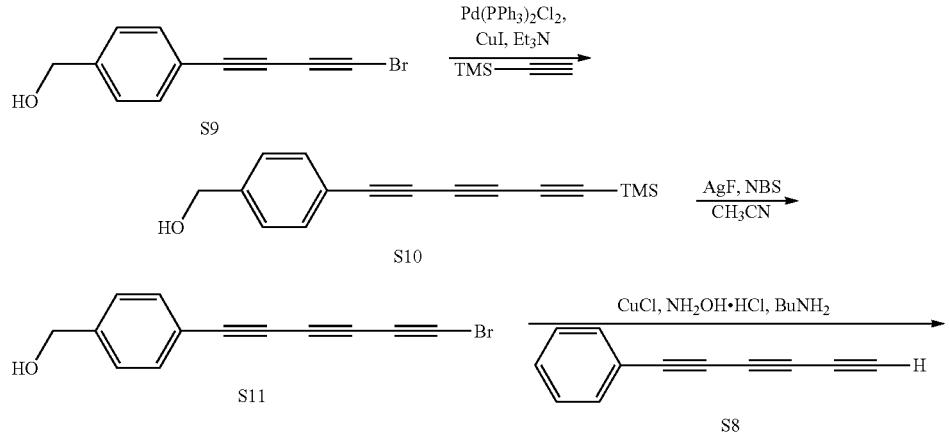

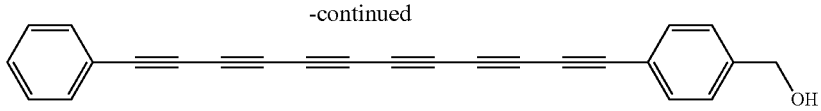

Carbow2066

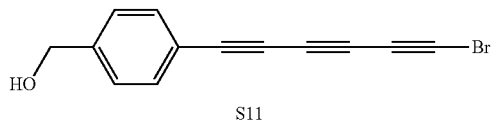

S11

A mixture of the diacetylene bromide S9 (29 mg, 0.12 mmol), CuI (2.2 mg, 0.012 mmol), and Pd(PPh$_3$)$_2$Cl$_2$ (8.4 mg, 0.012 mmol) in a three-neck flask was degassed and refilled with N$_2$. After this procedure was repeated three times, triethylamine (2 mL) and (trimethylsilyl)acetylene (24 mg, 0.24 mmol) were added with syringe. The reaction solution was stirred at 50° C. for 2 h, then the solvent was evaporated under reduced pressure, and the residue was further purified by column chromatography and the product S10 was dissolved in acetonitrile (1 mL). H$_2$O (11 μL, 0.6 mmol) and AgF (15 mg, 0.12 mmol) were added and the mixture was stirred for 20 min. Next N-bromosuccinimide (27 mg, 0.15 mmol) was added, and the mixture was stirred for 5 h. Acetonitrile was removed under reduced pressure and the residue was diluted with ethyl ether. The organic layer was washed with H$_2$O, brine and dried with MgSO$_4$. The solvent was removed and the residue was further purified by column chromatography to give S11 (16 mg, 52%).

$^1$H NMR (400 MHz, CDCl$_3$): δ 7.51 (d, J=7.9 Hz, 2H), 7.33 (d, J=7.9 Hz, 2H), 4.71 (s, 2H); $^{13}$C NMR (100 MHz, CDCl$_3$) δ 142.9, 133.3, 126.8, 119.7, 75.6, 74.2, 67.2, 66.1, 64.7, 59.0, 42.9; HRMS (ASAP): calcd for C$_{13}$H$_6$Br$^+$ [M-OH]$^+$: 240.9653, found: 240.9647.

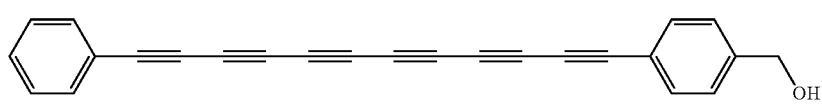

Carbow2066

Compound S8 was diluted with toluene (1 mL) and cooled to 0° C. CuCl (5.2 mg, 0.05 mmol), NH$_2$OH·HCl (7.0 mg, 0.10 mmol) and BuNH$_2$ (60 μL, 0.6 mmol) were added in order. Alkynyl bromide S11 (13 mg, 0.05 mmol) in toluene (1 mL) was added dropwise to the mixture. The reaction mixture was allowed to warm to rt and stirred for 10 h. The reaction was quenched with H$_2$O and extracted with ether. The organic layer was washed with H$_2$O, brine and dried with MgSO$_4$. After the solvent was removed by rotovapor, the product was purified by column chromatograph on silica to obtain Carbow2066 (6.8 mg, 42%) as a yellow solid.

$^1$H NMR (400 MHz, DMSO-d$_6$): δ 7.67 (dd, J=16.9, 7.6 Hz, 4H), 7.55 (t, J=7.5 Hz, 1H), 7.45 (t, J=7.6 Hz, 2H), 7.38 (d, J=8.0 Hz, 2H), 4.52 (s, 2H); $^{13}$C NMR (100 MHz, DMSO-d$_6$) δ 147.1, 134.1, 134.0, 131.9, 129.6, 127.2, 118.8, 116.7, 79.6, 79.2, 73.8, 73.5, 67.0, 66.9, 64.7, 64.6, 64.0, 63.9, 63.5, 63.3, 62.8; HRMS (ASAP): calcd for C$_{25}$H$_{13}$O$^+$ [M+H]$^+$: 329.0966, found: 329.0944.

Carbow2017 was prepared using the same procedures as Carbow2066.

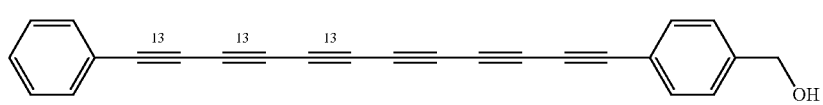

Carbow2017

$^1$H NMR (400 MHz, DMSO-d$_6$): δ7.68-7.59 (m, 4H), 7.57-7.50 (m, 1H), 7.48-7.35 (m, 4H), 4.50 (s, 2H); HRMS (ASAP): calcd for $^{12}$C$_{19}$$^{13}$C$_6$H$_{12}$O [M]$^+$ 334.1089, found 334.1080.

Synthesis of 4-yne Lyso

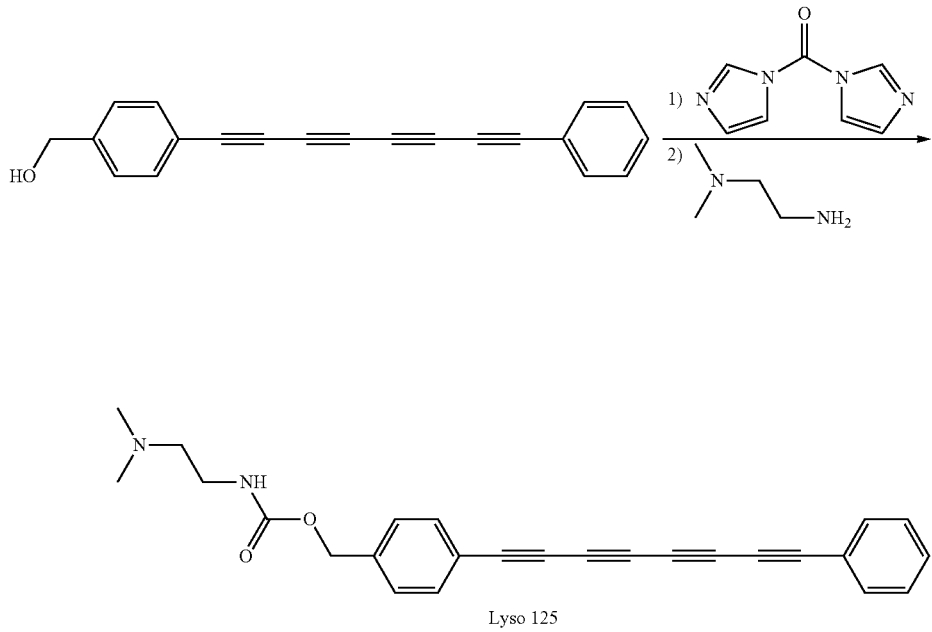

Lyso 125

To 1 (8.4 mg, 0.03 mmol) in CH$_2$Cl$_2$ (1 ml) was added 1,1'-carbonyldiimidazole (9.7 mg, 0.06 mmol) at rt. After the mixture was stirred at rt for 6 h, H$_2$O was added and the mixture was extracted with CH$_2$Cl$_2$. The organic phase was dried over Na$_2$SO$_4$ and the solvent was evaporated under reduced pressure. The residue was dissolved in CH$_2$Cl$_2$ (1 ml) and N,N-dimethylethylenediamine (6.6 μL, 0.06 mmol) was added and continued to stir at rt for 20 h, then concentrated at reduced pressure and purified by flash chromatography to obtain compound 2 as a yellow solid (9.8 mg, 82%).

$^1$H NMR (400 MHz, CDCl$_3$): δ 7.61-7.47 (m, 4H), 7.43-7.28 (m, 5H), 5.54 (br, 1H), 5.09 (s, 2H), 3.35-3.25 (m, 2H), 2.49 (t, J=5.6 Hz, 2H), 2.28 (s, 6H); $^{13}$C NMR (100 MHz, CDCl$_3$) δ 156.3, 139.0, 133.4, 133.3, 130.1, 128.7, 128.0, 120.6, 120.2, 77.8, 77.5, 74.8, 74.5, 67.4, 67.3, 65.9, 63.8, 63.7, 58.2, 45.1, 38.2; HRMS (ESI): calcd for C$_{26}$H$_{23}$N$_2$O$_2$$^+$ [M+H]$^+$: 399.1894, found: 399.1894.

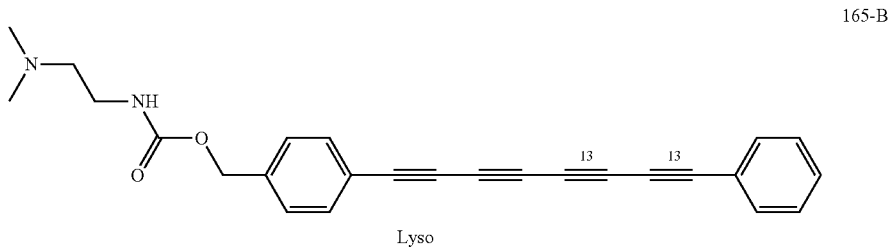 [SMILES: CN(C)CCNC(=O)OCc1ccc(C#CC#CC#CC#Cc2ccccc2)cc1]

165-B

Lyso $^1$H NMR (400 MHz, CDCl$_3$): δ 7.56-7.49 (m, 4H), 7.43-7.38 (m, 1H), 7.36-7.31 (m, 4H), 5.66 (br, 1H), 5.10 (s, 2H), 3.35-3.27 (m, 2H), 2.57 (t, J=5.6 Hz, 2H), 2.35 (s, 6H); HRMS (ESI): calcd for $^{12}$C$_{22}$$^{13}$C$_4$H$_{23}$N$_2$O$_2$$^+$ [M+H]$^+$: 395.1760, found: 395.1767.

Synthesis of 2-yne Mito

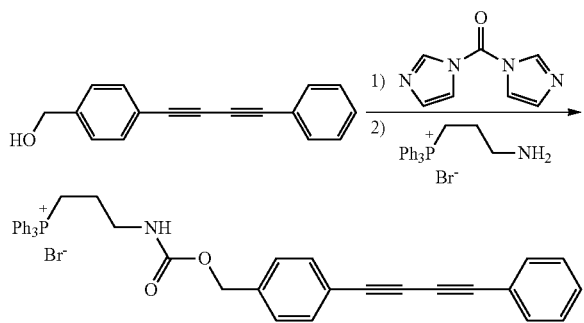

To 1 (10.5 mg, 0.045 mmol) in CH$_2$Cl$_2$ (1 ml) was added 1,1'-carbonyldiimidazole (11.2 mg, 0.068 mmol) at rt. After the mixture was stirred at room temperature for 3 h, H$_2$O was added and the mixture was extracted with CH$_2$Cl$_2$. The organic phase was dried over Na$_2$SO$_4$ and the solvent was evaporated under reduced pressure. The residue was dissolved in CH$_2$Cl$_2$ (1 ml) and (3-aminopropyl)triphenylphosphonium bromide (43 mg, 0.09 mmol) was added and continued to stir at rt for 15 h, then concentrated at reduced pressure and purified by flash chromatography to obtain compound 2 as a yellow solid (23 mg, 78%).

$^1$H NMR (400 MHz; CDCl$_3$): δ 7.79-7.69 (m, 8H), 7.67-7.60 (m, 6H), 7.53-7.46 (m, 3H), 7.43-7.38 (m, 2H), 7.37-7.28 (m, 5H), 5.05 (s, 2H), 3.81-3.69 (m, 2H), 3.50-3.40 (m, 2H), 1.88-1.76 (m, 2H); $^{13}$C NMR (100 MHz, CDCl$_3$) δ 156.9, 138.8, 135.2 (d, J=12.0 Hz), 133.6, 133.5, 132.6, 130.6, 129.3, 128.5, 127.7, 121.8, 120.9, 117.8, 81.7, 81.6, 74.1, 74.0, 65.5, 40.4 (d, J=68.8 Hz), 22.8 (d, J=15.2 Hz), 20.5; HRMS (ESI): calcd for C$_{39}$H$_{33}$NO$_2$P$^+$ [M-Br]$^+$: 578.2249, found: 578.2249.

Synthesis of 4-yne Mito

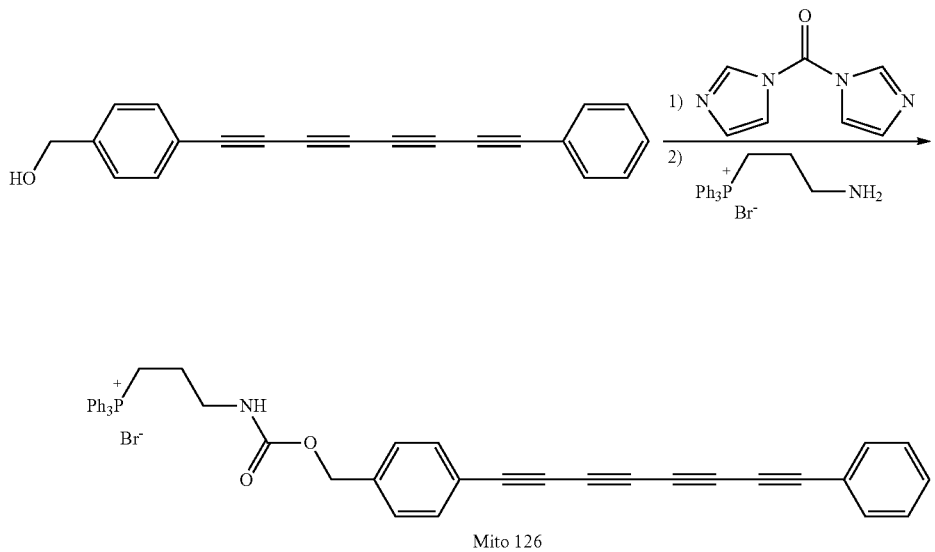

Mito 126

To 1 (8.4 mg, 0.03 mmol) in CH$_2$Cl$_2$ (1 ml) was added 1,1'-carbonyldiimidazole (9.7 mg, 0.06 mmol) at rt. After the mixture was stirred at room temperature for 6 h, H$_2$O was added and the mixture was extracted with CH$_2$Cl$_2$. The organic phase was dried over Na$_2$SO$_4$ and the solvent was evaporated under reduced pressure. The residue was dissolved in CH$_2$Cl$_2$ (1 ml) and (3-aminopropyl)triphenylphosphonium bromide (20 mg, 0.05 mmol) was added and continued to stir at rt for 20 h, then concentrated at reduced pressure and purified by flash chromatography to obtain compound 2 as a yellow solid (16 mg, 75%).

$^1$H NMR (400 MHz; CDCl$_3$): δ 7.80-7.60 (m, 14H), 7.57-7.49 (m, 3H), 7.44-7.28 (m, 7H), 5.05 (s, 2H), 3.78-3.65 (m, 2H), 3.50-3.40 (m, 2H), 1.90-1.75 (m, 2H); $^{13}$C NMR (100 MHz, CDCl$_3$) δ 156.9, 139.8, 135.2 (d, J=12.0 Hz), 133.6, 133.5, 133.3 (d, J=12.0 Hz), 130.6, 130.1, 128.6, 127.7, 120.6, 119.6, 117.8, 77.9, 77.8, 74.5, 67.4, 67.3, 65.5, 63.8, 40.5 (d, J=68.8 Hz), 22.8 (d, J=15.2 Hz), 20.3; HRMS (ESI): calcd for C$_{43}$H$_{33}$NO$_2$P$^+$ [M-Br]$^+$: 626.2249, found: 626.2252.

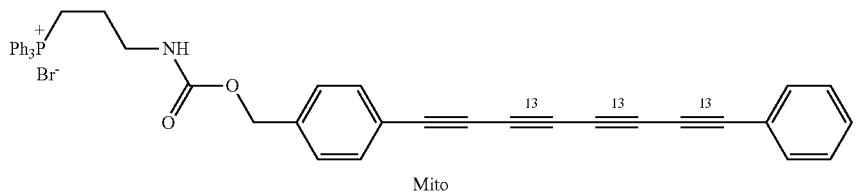

$^1$H NMR (400 MHz; CDCl$_3$): δ 7.80-7.75 (m, 3H), 7.73-7.62 (m, 11H), 7.57-7.50 (m, 3H), 7.46-7.30 (m, 7H), 5.06 (s, 2H), 3.70-3.60 (m, 2H), 3.49-3.40 (m, 2H), 1.88-1.78 (m, 2H); HRMS (ESI): calcd for $^{12}$C$_{37}$$^{13}$C$_6$H$_{33}$NO$_2$P$^+$ [M-Br]$^+$: 632.2450, found: 632.2452.

Synthesis of 4-yne PM

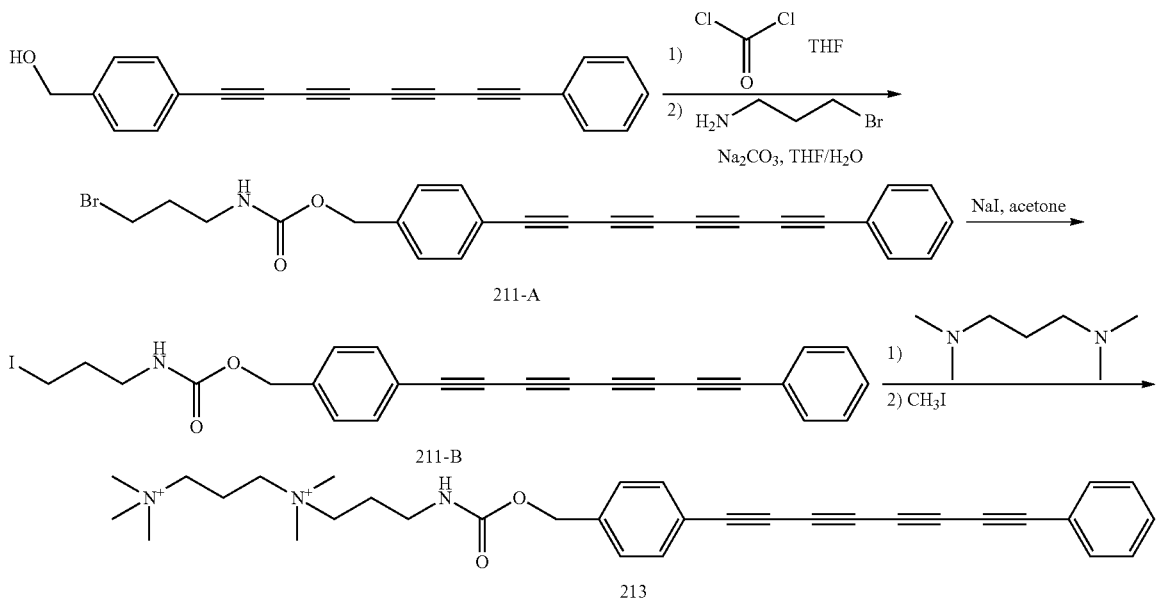

Compound 17 (168 mg, 0.6 mmol) was dissolved in THF (4 mL). The resulting solution was then added dropwise into a phosgene solution (0.90 mL, 1.2 mmol) at rt and was stirred for 24 h. The residual phosgene and solvent were then removed by high vacuum to produce a yellowish solid and it was dissolved in THF (2 mL) which was directly used for the subsequent reaction without further purification.

To a mixture of 3-bromopropan-1-amine hydrobromide (263 mg, 1.2 mmol) and sodium carbonate (254 mg, 2.4 mol) in THF (4 mL) and water (3 mL) was added dropwise the above chloroformate at rt and then the reaction mixture was allowed to stir at rt for 1 h. The reaction mixture was diluted with ethyl ether then the organic layer was washed with brine and dried with MgSO$_4$. After the solvent was removed by rotovapor, the product was purified by column chromatograph on silica to obtain compound 170 (178 mg, 67%) as a yellow solid.

$^1$H NMR (400 MHz, CDCl$_3$): δ 7.57-7.49 (m, 4H), 7.43-7.38 (m, 1H), 7.37-7.28 (m, 4H), 5.09 (s, 2H), 4.92 (br, 1H), 3.43 (t, J=6.4 Hz, 2H), 3.36 (q, J=6.4 Hz, 2H), 2.13-2.03 (m, 2H); $^{13}$C NMR (100 MHz, CDCl$_3$): δ 156.2, 138.7, 133.5, 133.3, 130.2, 128.7, 128.1, 120.6, 120.4, 77.9, 74.9, 74.5, 67.5, 67.3, 66.1, 63.9, 63.7, 39.6, 32.5, 30.6; HRMS (ASAP): calcd for C$_{25}$H$_{18}$BrNO$_2$$^+$ [M]$^+$ 443.0521, found 443.0533.

To a solution of 1 (22 mg, 0.05 mmol) in acetone (1 mL) was added NaI (75 mg, 0.50 mmol). After the mixture was stirred at 60° C. for 12 h, H$_2$O was added and the mixture was extracted with ether. The organic phase was dried over Na$_2$SO$_4$ and the solvent was removed under reduced pressure. The residue was dissolved in THF (1 mL) and N,N,N',N'-tetramethyl-1,3-propanediamine (42 µL, 0.25 mmol) was added. The mixture was stirred at 50° C. for 18 h. The solvent was removed by evaporation under reduced pressure and the crude product was washed several times with diethyl ether. This mono-charged intermediate was dissolved in CH$_3$CN (1 mL) and CH$_3$I (62 µL, 1 mmol) was added to the solution. After stirring the reaction mixture at 60° C. for 16 h, the solvent and CH$_3$I was evaporated under reduced pressure to give a yellow solid (16 mg, 43%).

$^1$H NMR (400 MHz, CD$_3$OD): δ 7.60-7.54 (m, 4H), 7.50-7.45 (m, 1H), 7.44-7.36 (m, 4H), 5.12 (s, 2H), 4.51 (s, 1H), 3.57-3.44 (m, 6H), 3.30-3.28 (m, 2H), 3.27 (s, 9H), 3.21 (s, 6H), 2.45-2.34 (m, 2H), 2.10-2.00 (m, 2H); $^{13}$C NMR (100 MHz, CD$_3$OD): δ 158.6, 141.1, 134.4, 134.2, 131.6, 129.9, 128.9, 121.3, 120.8, 79.0, 78.6, 74.6, 74.3, 67.5, 67.2, 66.8, 64.3, 64.1, 63.7, 61.4, 54.8, 54.3, 51.9, 38.8, 24.5, 19.0, 15.4; HRMS (ESI): calcd for C$_{33}$H$_{39}$N$_3$O$_2$$^{2+}$ [M-2I]$^{2+}$ 254.6515, found 254.6528.

Synthesis of 2-yneER

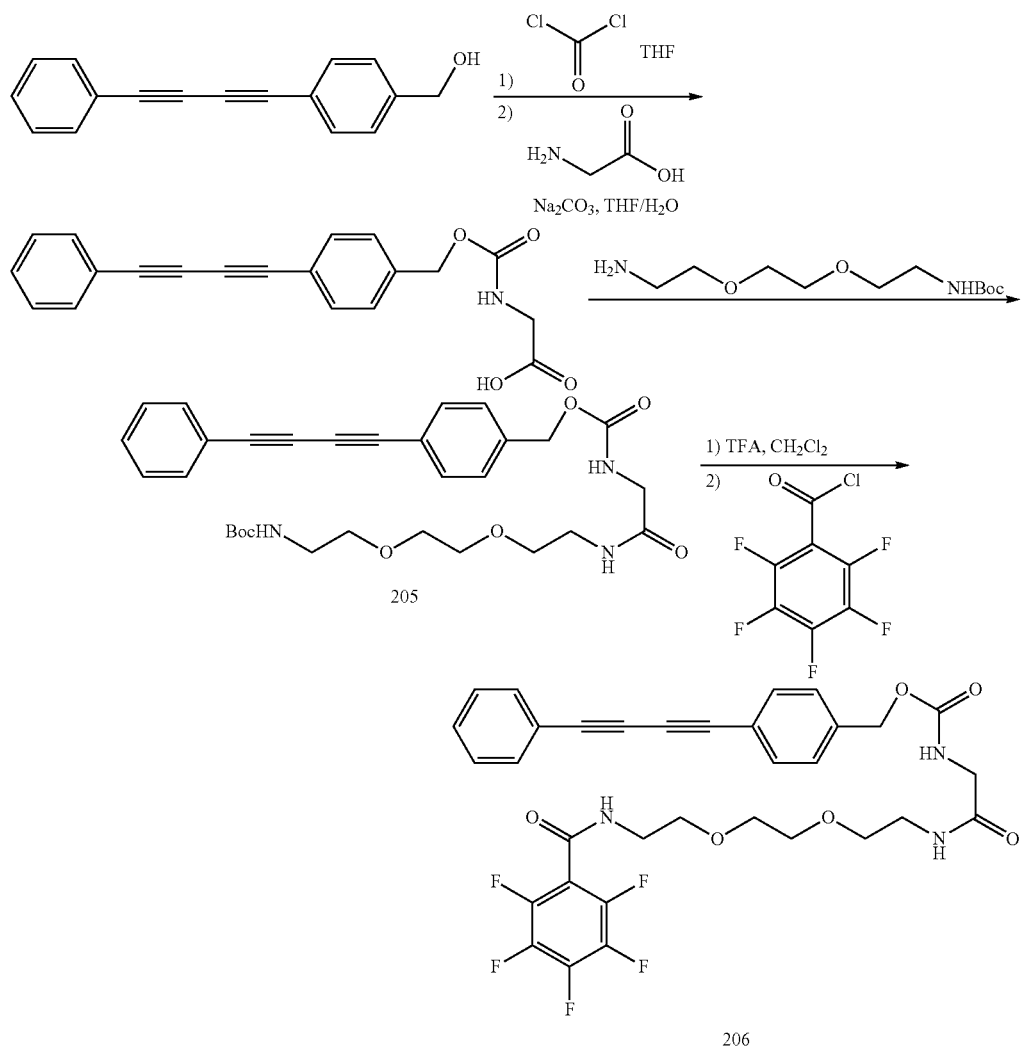

To a solution of 17 (70 mg, 0.3 mmol) in THF (3 mL) was added a phosgene solution (0.63 mL, 0.9 mmol) at rt and was stirred for 24 h. The residual phosgene and solvent were then removed by high vacuum to produce a solid and it was dissolved in THF (2 mL) which was directly used for the subsequent reaction without further purification.

To a mixture of glycine (68 mg, 0.9 mmol) and sodium carbonate (159 mg, 1.5 mol) in THF (2 mL) and water (1 mL) was added dropwise the above chloroformate at rt and then the reaction mixture was allowed to stir at rt for 2 h. The reaction mixture was quenched with 0.1 M HCl and diluted with ethyl ether. The organic layer was washed with brine and dried with MgSO$_4$. After the solvent was removed by rotovapor, the product was purified by column chromatograph on silica to obtain compound 170 (58 mg, 58%) as a white solid.

$^1$H NMR (400 MHz, CD$_3$OD): δ 7.55-7.50 (m, 4H), 7.43-7.35 (m, 5H), 5.13 (s, 2H), 3.84 (s, 2H); $^{13}$C NMR (100 MHz, CD$_3$OD): δ 173.5, 158.9, 139.9, 133.5, 133.4, 130.5, 129.7, 128.8, 122.9, 122.4, 82.3, 81.9, 74.5, 74.3, 67.0, 43.1; HRMS (ASAP): calcd for C$_{20}$H$_{14}$NO$_4$$^-$ [M−H]$^-$ 332.0923, found 332.0931.

15 (6.8 mg, 0.02 mmol) in DMF (1 mL) was treated with DIPEA (18 μL, 0.1 mmol) and HATU (7.6 mg, 0.02 mmol) at rt. After 5 min, N-Boc-2,2'-(ethylenedioxy)-diethylamine (7.4 mg, 0.03 mmol) was added. The mixture was stirred overnight at rt and the reaction was quenched by adding water. The product was extracted with DCM and dried with MgSO$_4$. The solvent was concentrated on a rotary evaporator and the residue was purified on a silica gel column to give the coupling product, which was dissolved in TFA-CH$_2$Cl$_2$ (1:4, 1 mL). The reaction mixture was stirred at rt for 1 h and was concentrated to yield the amine product without further purification. The amine was dissolved in CH$_2$Cl$_2$ (1 mL) and cooled to 0° C. Triethylamine (28 μL, 0.2 mmol) and pentafluorobenzoyl chloride (6 μL, 0.04 mmol) was added. After the mixture was stirred at 0° C. for 1 h, H$_2$O was added and the mixture was extracted with CH$_2$Cl$_2$. The organic phase was dried over Na$_2$SO$_4$ and the solvent was removed under reduced pressure. The residue was further purified by column chromatography to afford 6a (6.3 mg, 48%).

$^1$H NMR (400 MHz, CDCl$_3$): δ 7.54-7.48 (m, 4H), 7.40-7.27 (m, 5H), 6.97 (br, 1H), 6.48 (br, 1H), 5.61 (br, 1H), 5.08 (s, 2H), 3.81 (d, J=5.8 Hz, 2H), 3.68-3.58 (m, 8H), 3.56-3.50 (m, 2H), 3.45-3.40 (m, 2H); $^{13}$C NMR (100 MHz, CDCl$_3$): δ 169.0, 157.8, 156.6, 137.4, 132.8, 132.6, 129.4, 128.6, 128.0, 121.9, 121.8, 82.0, 81.1, 74.5, 73.9, 70.5, 70.4, 69.6, 69.5, 66.6, 44.6, 40.3, 39.3; HRMS (APCI): calcd for C$_{33}$H$_{28}$F$_5$N$_3$O$_6$Na$^+$ [M+Na]$^+$ 680.1796, found 680.1791.

Synthesis of 2-yne$_{1213}$LD

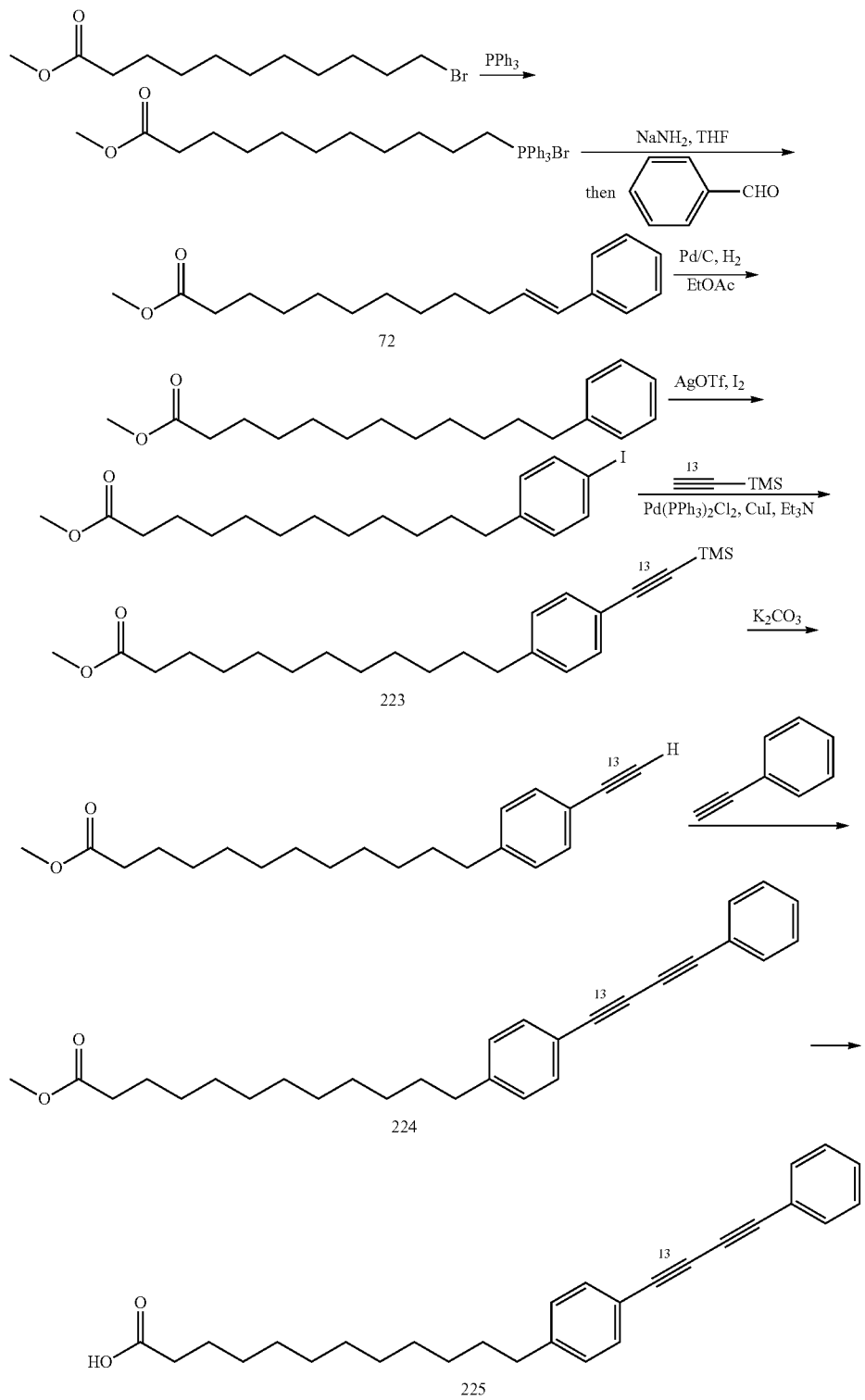

To a solution of methyl 11-bromoundecanoate 1 (852 mg, 2.9 mmol) in CH$_3$CN (10 mL) was added PPh$_3$ (836 mg, 3.2 mmol). After the mixture was stirred at 85° C. for 48 h, the solvent was removed by evaporation under reduced pressure and the residue was washed three times with diethyl ether.

The crude product was dissolved in THF (10 mL) and NaNH$_2$ (170 mg, 4.3 mmol) was added at 0° C. After stirring the reaction mixture at 0° C. for 30 min, benzaldehyde (0.35 mL, 3.5 mmol) was added and it was allowed to warm to rt and continue to stir at rt for 10 h. H$_2$O was added dropwise to quench the reaction and the mixture was extracted with Et$_2$O, then the combined organic layers were washed with brine, dried over Na$_2$SO$_4$, and concentrated under reduced pressure. The residue was purified by column chromatography to afford 1 (468 mg, 56%).

$^1$H NMR (400 MHz, CDCl$_3$): δ 7.38-7.20 (m, 5H), 6.45 (d, J=11.6 Hz, 1H), 5.70 (dt, J=11.8, 7.2 Hz, 1H), 3.70 (s, 3H), 2.41-2.30 (m, 4H), 1.75-1.60 (m, 2H), 1.52-1.43 (m, 2H), 1.34-1.20 (m, 10H); $^{13}$C NMR (100 MHz, CDCl$_3$): δ 174.4, 137.9, 133.3, 128.9, 128.2, 126.5, 125.8, 51.5, 34.2, 30.0, 29.6, 29.5, 29.4, 29.3, 29.2, 28.7, 25.0; HRMS (APCI): calcd for C$_{19}$H$_{29}$O$_2$$^+$ [M+H]$^+$ 289.2168, found 289.2167.

To a solution of 11 (173 mg, 0.6 mmol) in EtOAc (4 mL), 10% Pd/C catalyst (10 mg) was added. The reaction mixture was stirred under H$_2$ atmosphere overnight at rt. The catalyst was removed by filtration through a pad of Celite, and the organic solvent was evaporated under reduced pressure. The crude product was dissolved in CH$_2$Cl$_2$ (5 mL) then AgOTf (154 mg, 0.6 mmol) and iodine (152 mg, 0.6 mmol) were added at rt. After stirring the reaction mixture at rt for 2 h, saturated sodium bisulfite solution was added and stirred at rt for 10 min. The mixture was extracted with ether and the organic layer was washed with H$_2$O, brine and dried with MgSO$_4$. The solvent was removed under reduced pressure and the residue was further purified by column chromatography to afford 6a (187 mg, 75%).

$^1$H NMR (400 MHz, CDCl$_3$): δ 7.60 (d, J=8.0 Hz, 2H), 6.94 (d, J=8.0 Hz, 2H), 3.69 (s, 3H), 2.56 (t, J=7.2 Hz, 2H), 2.33 (t, J=7.2 Hz, 2H), 1.69-1.54 (m, 4H), 1.40-1.23 (m, 14H); $^{13}$C NMR (100 MHz, CDCl$_3$): δ 174.3, 142.5, 137.3, 130.6, 90.6, 51.5, 35.5, 34.2, 31.3, 29.6, 29.5, 29.4, 29.3, 29.2, 25.0; HRMS (ASAP): calcd for C$_{19}$H$_{30}$IO$_2$$^+$ [M+H]$^+$ 417.1290, found 417.1298.

$^1$H NMR (400 MHz, CDCl$_3$): δ 7.40 (dd, J=5.4, 7.8 Hz, 2H), 7.13 (d, J=7.8 Hz, 2H), 3.67 (s, 3H), 3.03 (dd, J=52.2, 248.4 Hz, 1H), 2.60 (t, J=7.6 Hz, 2H), 2.30 (t, J=7.6 Hz, 2H), 1.65-1.54 (m, 4H), 1.35-1.24 (m, 14H); $^{13}$C NMR (100 MHz, CDCl$_3$): δ 174.4, 144.1, 132.1 (t, J=8.4 Hz), 128.5 (d, J=21.4 Hz), 119.7 (d, J=55.2 Hz), 84.0 (d, J=698.2 Hz), 76.4 (d, J=698.2 Hz), 51.5, 36.0, 34.2, 31.3, 29.6, 29.5, 29.4, 29.3, 29.2, 25.1; HRMS (ASAP): calcd for $^{12}$C$_{19}$$^{13}$C$_2$H$_{31}$O$_2$$^+$ [M+H]$^+$ 317.2392, found 317.2401.

A solution of CuCl (5.0 mg, 0.05 mmol) and TMEDA (15 μL, 0.10 mmol) in acetone (1 ml) was bubbled with air for 10 mins at rt, then the mixture of 11 (16 mg, 0.05 mmol) and phenylacetylene (22 μL, 0.2 mmol) in CH$_2$Cl$_2$ (1 ml) were added and continued to stirred with air at rt for 1 h. The solvent was evaporated at reduced pressure and the residue was further purified by column chromatography to give the pure product, which was dissolved in THF-MeOH (2:1, 0.9 mL) and 3.0 M KOH (0.1 mL, 0.3 mmol) was added. After the mixture was stirred at room temperature for 1 h, 1.0 M HCl was added and the mixture was extracted with ether. The organic phase was dried over Na$_2$SO$_4$ and the solvent was evaporated under reduced pressure. The residue was purified by column chromatography to afford 1 (11.6 mg, 55%).

$^1$H NMR (400 MHz; CDCl$_3$): δ 7.56-7.49 (m, 2H), 7.47-7.41 (m, 2H), 7.39-7.30 (m, 3H), 7.15 (d, J=8.0 Hz, 2H), 2.60 (t, J=7.6 Hz, 2H), 2.35 (t, J=7.6 Hz, 2H), 1.69-1.53 (m, 4H), 1.37-1.23 (m, 14H); $^{13}$C NMR (100 MHz, CDCl$_3$) δ 179.6, 144.8, 132.6, 132.5, 129.2, 128.7 (d, J=22.6 Hz), 128.5, 122.1 (d, J=15.6 Hz), 119.0 (dd, J=60.0, 364.0 Hz), 82.1 (d, J=784.0 Hz), 73.3 (d, J=784.0 Hz), 36.1, 34.1, 31.3, 29.6, 29.5, 29.4, 29.3, 29.2, 24.8; HRMS (ASAP): calcd for $^{12}$C$_{26}$$^{13}$C$_2$H$_{31}$O$_2$$^-$ [M−H]$^-$ 401.2391, found 401.2402.

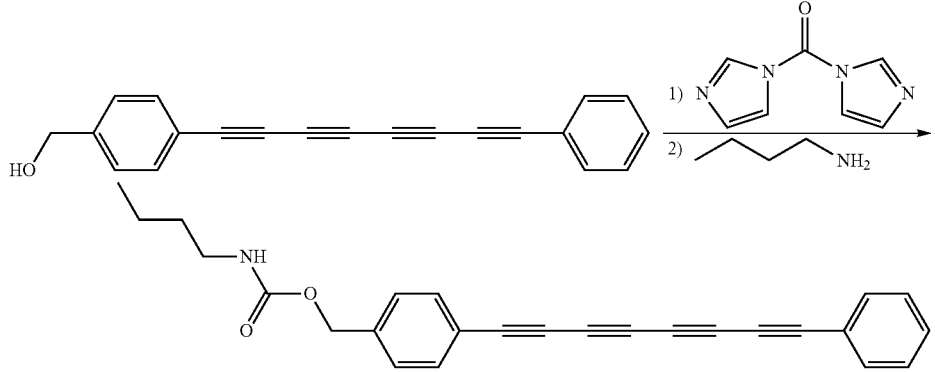

A mixture of aryl iodide 11 (166 mg, 0.4 mmol), CuI (7.6 mg, 0.04 mmol), and Pd(PPh$_3$)$_2$Cl$_2$ (28 mg, 0.04 mmol) in a 25 mL three-neck flask was degassed and refilled with N$_2$. After this procedure was repeated three times, triethylamine (5 mL) and (trimethylsilyl)acetylene-1,2-$^{13}$C$_2$ (60 mg, 0.6 mmol) were added with syringe. The reaction solution was stirred at 40° C. for 2 h, then the solvent was evaporated under reduced pressure. The residue was further purified by column chromatography to give the pure product which was dissolved in MeOH (4 mL) and K$_2$CO$_3$ (138 mg, 1.0 mmol) was added. After the mixture was stirred at room temperature for 3 h, H$_2$O was added and the mixture was extracted with ether. The organic phase was dried over Na$_2$SO$_4$ and the solvent was evaporated under reduced pressure. The residue was purified by column chromatography to afford 6a (91 mg, 72%).

To 1 (7.2 mg, 0.025 mmol) in CH$_2$Cl$_2$ (1 ml) was added 1,1'-carbonyldiimidazole (6.5 mg, 0.04 mmol) at rt. After the mixture was stirred at room temperature for 3 h, H$_2$O was added and the mixture was extracted with CH$_2$Cl$_2$. The organic phase was dried over Na$_2$SO$_4$ and the solvent was evaporated under reduced pressure. The residue was dissolved in CH$_2$Cl$_2$ (1 ml) and n-Butylamine (7.5 μL, 0.075 mmol) was added and continued to stir at rt for 12 h, then concentrated at reduced pressure and purified by flash chromatography to obtain compound 2 as a yellow solid (6.8 mg, 72%).

$^1$H NMR (400 MHz, CDCl$_3$): δ 7.59-7.52 (m, 4H), 7.46-7.40 (m, 1H), 7.39-7.31 (m, 4H), 5.11 (s, 2H), 4.75 (br, 1H), 3.22 (q, J=6.4 Hz, 2H), 1.56-1.46 (m, 2H), 1.42-1.32 (m, 2H), 0.94 (t, J=7.2 Hz, 3H); $^{13}$C NMR (100 MHz,

CDCl₃): δ 156.2, 139.1, 133.5, 133.3, 130.2, 128.7, 128.0, 120.6, 120.2, 77.9, 77.5, 74.8, 74.5, 67.5, 67.3, 65.9, 63.9, 63.7, 41.0, 32.1, 20.0, 13.8; HRMS (ASAP): calcd for $C_{26}H_{21}NO_2^+$ [M]⁺: 379.1578, found: 379.1572.

133.3, 130.2, 128.7, 128.0, 120.6, 120.3, 77.9, 77.5, 74.8, 74.5, 67.5, 67.3, 66.1, 63.9, 63.7, 40.0, 28.5, 25.7, 25.0; HRMS (ASAP): calcd for $C_{30}H_{23}N_2O_6^+$ [M+H]⁺: 507.1556, found: 507.1560.

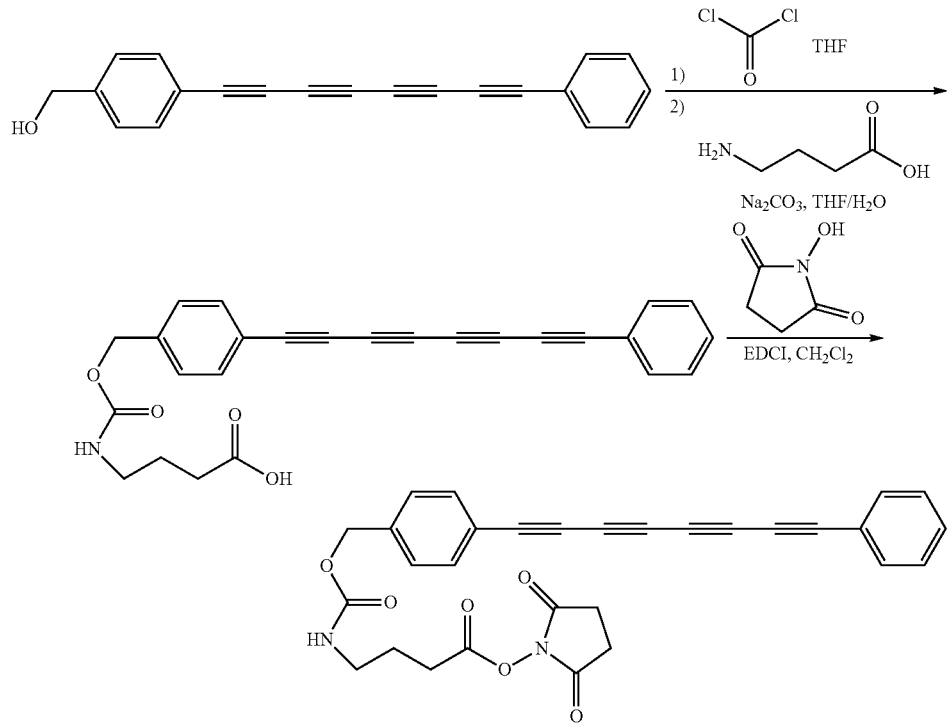

Compound 17 (8.4 mg, 0.03 mmol) was dissolved in THF (1 mL). The resulting solution was then added dropwise into a phosgene solution (0.045 mL, 0.06 mmol) at rt and was stirred for 24 h. The residual phosgene and solvent were then removed by high vacuum to produce a yellowish solid and it was dissolved in THF (1 mL) which was directly used for the subsequent reaction without further purification.

To a mixture of 4-Aminobutanoic acid (6.2 mg, 0.06 mmol) and sodium carbonate (10.5 mg, 0.1 mol) in THF (1 mL) and water (1 mL) was added dropwise the above chloroformate at rt and then the reaction mixture was allowed to stir at rt for 1 h. The reaction mixture was quenched with 0.1 M HCl and diluted with ethyl acetate. The organic layer was washed with brine and dried with MgSO₄. After the solvent was removed by rotovapor, the product was directly used for the next reaction without further purification.

To the above product in CH₂Cl₂ (1 mL) were added DMAP (3.6 mg, 0.03 mmol), N-hydroxylsuccinimide (11.2 mg, 0.10 mmol) and EDCI (11.5 mg, 0.06 mmol). After the mixture was stirred at rt for 24 h, H₂O was added and the mixture was extracted with ether. The organic phase was dried over Na₂SO₄ and the solvent was evaporated under reduced pressure. The residue was purified by column chromatography to afford 6a (8.6 mg, 57%).

¹H NMR (400 MHz, CDCl₃): δ 7.56-7.50 (m, 4H), 7.43-7.29 (m, 5H), 5.09 (s, 2H), 3.32 (q, J=6.4 Hz, 2H), 2.82 (s, 4H), 2.66 (t, J=7.2 Hz, 2H), 2.03-1.94 (m, 2H); ¹³C NMR (100 MHz, CDCl₃): δ 169.2, 168.3, 156.3, 138.9, 133.5,

Example 2: Stimulated Raman Scattering (SRS) Microscopy

An integrated laser system (picoEMERALD, Applied Physics & Electronics, Inc.) is used to produce two synchronized laser beams at 80 MHz repetition rate. A fundamental Stokes beam (1064 nm, 6 ps pulse width) is intensity modulated at 8 MHz by an electro-optic-modulator with >90% modulation depth, and a tunable pump beam (720-990 nm, 5-6 ps pulse width) is produced by a build-in optical parametric oscillator. The pump and Stokes beams are spatially and temporally overlapped using two dichroic mirrors and a delay stage inside the laser system, and coupled into an inverted laser-scanning multiphoton microscope (FV1200MPE, Olympus) with optimized near-IR throughput.

The lasers are focused on the sample through a 25× water objective (XLPlan N, 1.05 N.A. MP, Olympus) or a 60× water objective (UPlanAPO/IR, 1.2 N.A., Olympus) with high near-IR transmission. The beam sizes of pump and Stokes laser are adjusted to match the back-aperture of the objective. After the sample, both beams are effectively collected by a high N.A. oil condenser lens (1.4 N.A., Olympus) in Kohler illumination and the laser-scanning motion is descanned with a telescope. By blocking the Stokes beam with a high O.D. bandpass filter (890/220 CARS, Chroma Technology), only the pump beam is detected by a large-area (10 mm×10 mm) silicon photodiode (FDS1010, Thorlabs) reverse-biased at 64 DC voltage to maximize saturation threshold and response bandwidth. The output current of photodiode is filtered with a 8 MHz electronic bandpass filter (KR 2724, KR electronics), and terminated with 50Ω before entering a RF lock-in amplifier (SR844, Stanford Research Systems or HF2LI, Zurich instrument).

The stimulated Raman loss signal is extracted from the pump beam by demodulation at the 8 MHz frequency with near short-noise-limited sensitivity. The in-phase signal from the lock-in amplifier at each pixel is sent to the analog interface box (FV10-ANALOG, Olympus) of the microscope to generate the SRS image by scanning across the whole field of view. SRS images are acquired using 25× objective with 30 μs time constant from the lock-in amplifier and 100 μs pixel dwell time (10.2 s per 320×320 frame), unless otherwise specified. Measured after the objective, the pump power is from 12-48 mW and the Stokes power is from 40-120 mW for all cell images (FIG. 4). For bead (FIG. 5d and FIG. 13) and pattern (FIG. 14) imaging, the pump power is from 12-24 mW and the Stokes power is 20 mW. For immuno-imaging of α-tubulin (FIG. 4b), 100 s time constant and 200 μs pixel dwell time is used. 10-color live-cell organelle imaging (FIG. 4i) is performed using 60× objective and 80 s time constant. Photostability experiments (FIG. 10) are performed with 3 μs time constant and 4 μs pixel dwell time with 0.4 s per frame (320×320 pixels). Stimulated Raman scattering spectra are acquired by scanning the pump beam across the selected wavelength range point by point.

All bright-field and fluorescence images are collected using the Olympus FV1200 confocal microscope with CW laser excitation (488, 543 and 635 nm) and standard bandpass filter sets. Two-photon fluorescence images of NucBlue are collected with 780 nm pump laser excitation and detected by non-descanned photomultiplier tubes. All images are analyzed and assigned color by ImageJ.

Spontaneous Raman Spectroscopy

Raman spectra are collected with the LabSpec 6 software on a confocal Raman microscope (Xplora, Horiba Jobin Yvon) at room temperature. The samples are excited through a 50× air objective (MPlan N, 0.75 N.A., Olympus) by a 532-nm diode laser (27 mW after the objective). The acquisition time for bead solution samples (FIG. 12) is 5 s and for beads in live cells (FIG. 5c) is 10 s.

Example 3: Secondary Antibody Conjugation with 4-yne NHS Ester

Goat-anti-Rabbit secondary antibodies (2 mg/mL, Millipore, AP132) are adjusted to pH-8.3 with sodium bicarbonate solution. 50 μL 4 mg/mL 4-yne NHS ester in DMSO solution is added dropwise to 250 μL protein solution while stirring. Reaction is kept under gentle stirring at RT for 1 h. The labeled antibodies are purified using gel permeation chromatography with Sephadex® G-25 (Sigma, G25150). Sephadex® G-25 gel is first swelled in PBS buffer at 90° C. for 1 h and settled down at room temperature. The gel is then exchanged with fresh PBS buffer and stored at 4° C. For gel chromatography, the column (diameter ~1 cm and length >12 cm) is loaded with swelled gels and equilibrated with PBS buffer. The antibody solution is applied and eluted with PBS. The first band with light color for 4-yne conjugated antibodies is collected. The solution is centrifuged briefly and the supernatant is concentrated using Amicon® Ultra Centrifugal Filters (Millipore, UFC501096) to a final concentration of ~2 mg/mL in PBS with 5 mM sodium azide and stored at −20° C.

Example 4: Sample Preparations for SRS and Fluorescence Imaging

HeLa cells are cultured with DMEM medium (Invitrogen, 11965) supplemented with 10% fetal bovine serum (Invitrogen, 16000) and 1% penicillin-streptomycin (Invitrogen, 15140). All cell cultures are maintained in a humidified environment at 37° C. and 5% $CO_2$.

All samples are assembled into a chamber using an imaging spacer (Sigma, GBL654008) filled with PBS solution for imaging.

Immuno-Staining for α-Tubulin Imaging Infixed HeLa Cells (FIG. 4b)

HeLa cells are seeded on a glass coverslip in a 4-well plate with ~1 mL of culture media for 24 h. Cells are fixed with methanol for 25 min, washed with 10% goat serum added with 1% bovine serum albumin (BSA) and 0.3M glycine twice and permeabilized with 0.1% Tween PBS solution for 40 min. Anti-α-tubulin primary antibody in rabbit (Abcam, ab 18251) is added to the cells at 1:50 dilution in 3% BSA solution and incubated overnight at 4° C. The cells are then blocked with 10% goat serum for 30 min and incubated with 4-yne conjugated goat-anti-rabbit secondary antibody by 1:25 dilution in 10% goat serum at 4° C. overnight. The cells are washed with PBS twice before imaging.

15-Color Imaging of Live Hela Cells with Super-Multiplexed Polyynes (FIG. 4c)

HeLa cells are seeded in 15 wells of a 24-well plate for 24 h. Each well is labeled with a single color of fluorescent dyes or polyynes in culture media at 37° C., including 2-yne Mito (5 μM), Carbow2172 (3 μM), Carbow2141 (10 μM), Carbow 2128 (2 μM), Carbow2100 (4 μM), Carbow2086 (10 μM), Carbow2066 (10 μM), Carbow2049 (5 μM), and Carbow2017 (10 μM) for 4 h, 2-yne$_{1213}$ LD (4 μM) for 24 h, MitoTracker Green (100 nM, Invitrogen, M7514), MitoTracker Orange CMTMRos (50 nM, Invitrogen, M7510), and MitoTracker Deep Red (50 nM, Invitrogen, M22426) for 1 h, NucBlue® Live ReadyProbes Reagent (1 drop, Invitrogen, R37605) and FM 4-64 (5 μg/mL, Invitrogen, T3166) for 30 min. Cells are then washed with PBS once, detached from each well with trypsin for 2 min, and mixed together in fresh culture media. The cell mixture is centrifuged at 1000 rpm for 1.5 min and the cell pellet is mixed with PBS. Cells are added to the imaging chamber and settled for 1 h to reduce the movement before imaging, and each cell is maintained with a single color during the imaging period.

Mitochondria Imaging in Live HeLa Cells with Carbow2141 (FIG. 4d)

HeLa cells are cultured on a glass coverslip in a 4-well plate for 24 h, and 2 M Carbow2141 Mito is added in the media for 1 h at 37° C. Cells are washed with PBS for three times before imaging. For co-localization, 100 nM MitoTracker Deep Red is used to stain mitochondria for 1 h.

Lysosome Imaging in Live HeLa Cells with Carbow2141 Lyso (FIG. 4e)

Cells were cultured on a glass coverslip in a 4-well plate for 24 h, and 4 μM Carbow2141 Lyso is added to cells for 30 min at 37° C. Cells are washed with PBS for three times before imaging. For co-localization, 100 nM LysoTracker Red (Invitrogen, L7528) is used to stain lysosome for 30 min.

Plasma Membrane Imaging in Live HeLa Cells with Carbow2141 PM (FIG. 4f)

Cell are incubated with 3 µM Carbow2141 PM in the culture media for 20 min at 37° C. and are washed with PBS for three times before imaging. For co-localization, 0.5 µg/mL CellMask Deep Red (Invitrogen, C10046) is used to stain cell membrane for 5 min.

Endoplasmic Reticulum Imaging in Live HeLa Cells or COS-7 Cells with Carbow2226 ER (FIG. 4g)

Cells were cultured on a glass coverslip in a 4-well plate for 24 h and incubated with 10 µM Carbow2226 ER for 2 h at 37° C. Cells were washed with PBS for three times before imaging. For colocalization, 1 µM ERTracker Green (Invitrogen, E34251) was used to stain endoplasmic reticulum for 2 h.

Lipid Droplets Imaging in Live HeLa Cells or COS-7 Cells with Carbow2202 LD (FIG. 4h)

Cells were cultured on a glass coverslip in a 4-well plate for 24 h, and 10 µM Carbow2202 LD was added to cell media for overnight at 37° C. Cells were washed with PBS for three times before imaging. For colocalization, 1 µM Nile red (Invitrogen, N1142) was used to stain lipid droplets for 10 min.

Ten-Color Organelle-Specific Imaging in Live Hela Cells with Polyyne Probes (FIG. 4i)

HeLa cells were seeded on a glass coverslip in a 4-well plate with culture media for 24 h, and actin-GFP plasmids (Invitrogen, C10582) were transfected into cells for 48 h before imaging according to Invitrogen protocol. 10 M Carbow2202 LD was added in the culture media overnight at 37° C. before imaging. On the day of imaging, cells were incubated with 10 µM Carbow2226 ER and 0.02% Pluronic F-127 (Invitrogen, P3000MP) for 2 h, 2 µM Carbow2086 Lyso, 4 µM Carbow2062 Mito and 1 µM SiR-tubulin (Cytoskeleton, CY-SC002) for 1 h, 3 µM Carbow2141 PM and one drop of NucBlue for 20 min at 37° C. 1 h before imaging, cells were labeled with 5 µM BODIPY TR Ceramide (Invitrogen D7540) and 0.1% Pluronic F-127 in Hanks' buffered salt solution (HBSS, Invitrogen, 14025) for 10 min at 37° C. After the incubation, cells were washed with PBS solution twice, quickly immersed in 5 µg/mL FM 4-64 HBSS solution (without magnesium or calcium) on ice for 1 min before imaging.

Cell Viability Assays (FIG. 11)

HeLa cells are incubated with organelle-targeted polyynes at specified conditions or illuminated by SRS lasers. Cell viability assays are then performed using Live/Dead viability/cytotoxicity kit for mammalian cells (Invitrogen, L3224) by incubating with 2 M calcein AM and 4 µM EthD-1 working solution for 20 min at 37° C.

Example 5: Spectral Barcoding in Polystyrene Beads with Super-Multiplexed Polyynes 10 µL 3.0 µm polystyrene beads (10% in aqueous solution, Sigma, LB30) are mixed with 5 µL Pluronic F-127 (20% in DMSO) and 85 µL deionized water. Selected polyynes (in DMSO) are diluted to designated concentrations (Table 1 and 2) in a solution of 100 µL deionized water and 100 µL THF (Sigma, 401757). The polyyne THF-water solution was then mixed with 100 µL of bead and F-127 solution. After vortexing for 10 min, the mixture was further agitated on a shaker for 2 h at room temperature and then washed with deionized water three times. For live-cell labeling, barcoded beads were incubated in 1 wt % poly-L-lysine aqueous solution (Mw=30,000-70,000, Sigma, P2636) for 30 min at room temperature and washed with water for three times before use.

Example 6: Live-Cell Tagging with Spectral Barcoded Beads

HeLa cells are seeded on a glass coverslip in a 4-well plate with culture media for 24 h. Cell are incubated with barcoded beads for 24 h before confocal Raman measurement (FIG. 5c) or SRS imaging (FIG. 5d and FIG. 13). A custom MATLAB program is used to decode the spectral barcodes of beads in the whole field of view based on the hyperspectral SRS images.

Example 7: Fabrication of Microscopic Pattern and Frequency Encryption with Super-Multiplexed Polyynes PMMA (495K A4+950K A9) is spin coated onto $Si/SiO_2$ substrate and baked at 170° C. for 10 min. The substrate is exposed to e-beam lithography and a solution of developer to generate the microscopic pattern of Columbia logo. The PDMS precursor is prepared using Sylgard 184 Silicone Elastomer Kit. Elastomer and curing agent (10:1 ratio) are mixed and poured onto the patterned $Si/SiO_2$ substrate. After heating at 80° C. for 1 h, the PDMS pattern is peeled off from the substrate.

Frequency encryption is carried out by immersing the PDMS with Columbia logo in ethanol solution (Fisher, BP2818) with selected polyynes (0.2-1.2 mM) at room temperature overnight. After ethanol evaporation, the pattern is rinsed with deionized water before imaging (FIG. 14).

For correlation analysis in spectroscopy measurements (FIGS. 1b and 4a), least-squares regression is applied with Origin software. Reported n values represent the number of compounds (FIG. 1b) and concentrations (FIG. 4a) measured independently in the experiments. For the immunostaining and imaging experiments (FIG. 4b), experiments were repeated four times independently with similar results. For the 15-color imaging experiments (FIG. 4c), experiments were repeated three times independently with similar results. For the live-cell, organelle-targeted experiments (FIG. 4d-h), experiments were repeated five times independently with similar results. For the ten-color organelle-targeted imaging (FIG. 4i), experiments were repeated three times independently with similar results. For the bead labeling in live cells by spontaneous Raman readout (FIG. 5c) or SRS imaging (FIG. 5d), experiments were repeated three times independently with similar results.

Figure 15:
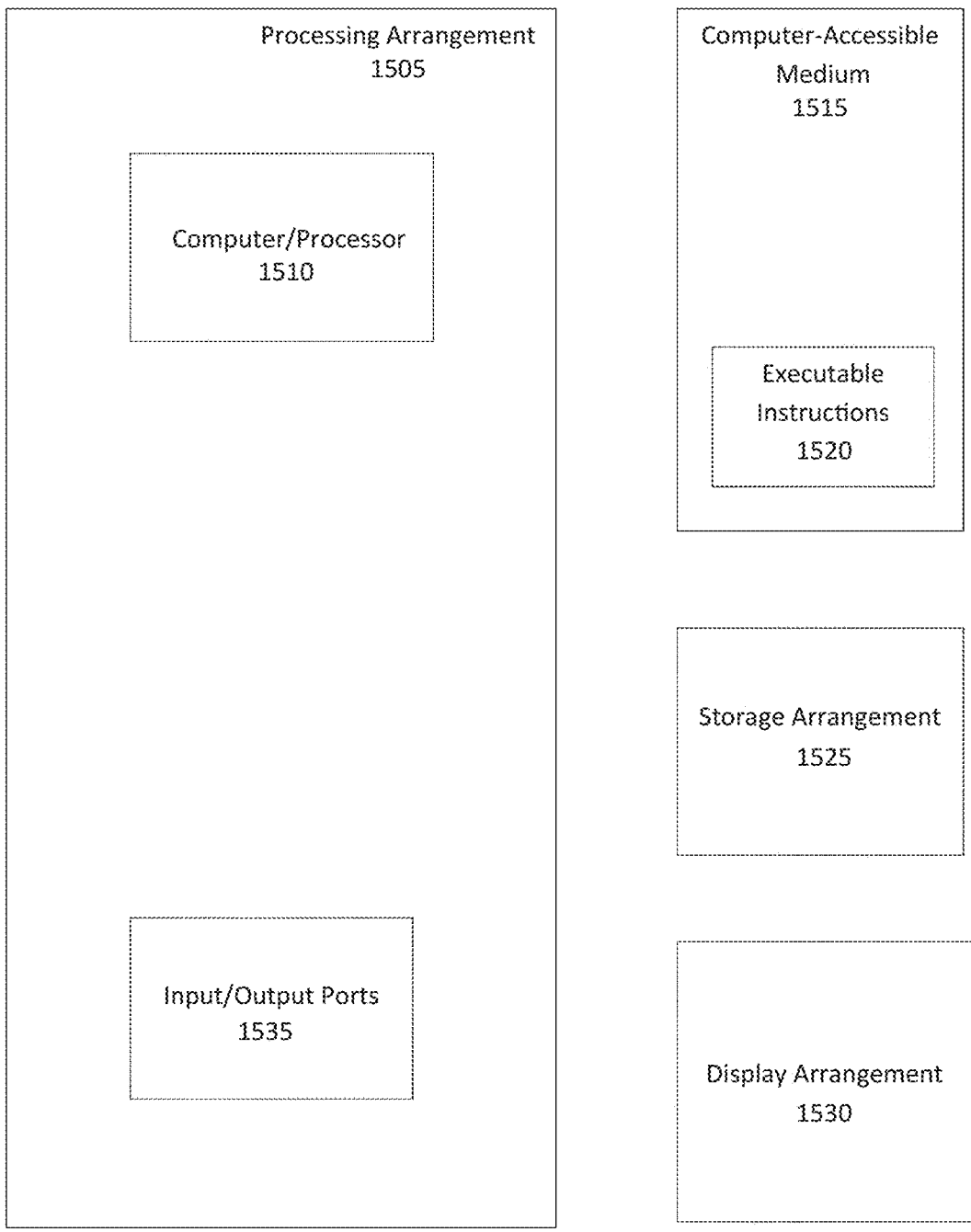
FIG. 15 is an illustration of an exemplary block diagram of an exemplary system in accordance with certain exemplary embodiments of the present disclosure.

FIG. 15 shows a block diagram of an exemplary embodiment of a system according to the present disclosure. For example, exemplary procedures in accordance with the present disclosure described herein can be performed by a processing arrangement and/or a computing arrangement 1505. Such processing/computing arrangement 1505 can be, for example entirely or a part of, or include, but not limited to, a computer/processor 1510 that can include, for example one or more microprocessors, and use instructions stored on a computer-accessible medium (e.g., RAM, ROM, hard drive, or other storage device). As shown in FIG. 15, for example a computer-accessible medium 1515 (e.g., as described herein above, a storage device such as a hard disk, floppy disk, memory stick, CD-ROM, RAM, ROM, etc., or a collection thereof) can be provided (e.g., in communication with the processing arrangement 1505). The computer-accessible medium 1515 can contain executable instructions 1520 thereon. In addition or alternatively, a storage arrangement 1525 can be provided separately from the computer-accessible medium 1515, which can provide the instructions to the processing arrangement 1505 so as to configure the processing arrangement to execute certain exemplary procedures, processes, and methods, as described herein above, for example.

Further, the exemplary processing arrangement 1505 can be provided with or include an input/output arrangement 1535, which can include, for example a wired network, a wireless network, the internet, an intranet, a data collection probe, a sensor, etc. As shown in FIG. 15, the exemplary processing arrangement 1505 can be in communication with an exemplary display arrangement 1530, which, according to certain exemplary embodiments of the present disclosure, can be a touch-screen configured for inputting information to the processing arrangement in addition to outputting information from the processing arrangement, for example. Further, the exemplary display 1530 and/or a storage arrangement 1525 can be used to display and/or store data in a user-accessible format and/or user-readable format.

Example 8: Demonstration of an Amplification Method for SRS Imaging of Proteins

HCR (Hybridization Chain Reaction) system is a cascade amplification method which will trigger self-assembly of stable DNA monomers upon exposure to a target DNA or RNA fragment [37]. It was originally developed to amplify nucleic acid signal. Recently, immunosignal hybridization chain reaction (isHCR) has been reported to combine antibody-antigen interactions with HCR technology, which results in amplification of immunofluorescence signals by up to two to three orders of magnitude with low background [38].

To amplify our SRS signal from low-abundance protein targets, our idea is to employ this isHCR amplification method by conjugating a short DNA sequence to the secondary antibody in immunostaining (FIG. 16a). With this design, we demonstrated the protein imaging with SRS and two vibrational probes (Alexa Fluo 647 and Atto740).

Quantified by fluorescence on Alexa 647, an amplification factor of more than 10-times have been achieved (FIG. 16b-c). This is very exciting, as it will make SRS technique powerful in super-multiplex protein imaging. In FIG. 16b, we presented, without HCR, SRS image on A647 stained-tubulin is very vague with low SNR. Interestingly and remarkably, under the same condition (laser power, time constant, antibody concentration), we easily collected the SRS image after HCR amplification on tubulin-A647. Similarly, for some low abundant targets like transmembrane glycoprotein EpCAM ((a widely used tumor marker), HCR amplification is indeed helpful on signal enhancement and image quality improvement (FIG. 16d).

EXEMPLARY REFERENCES

The following references are hereby incorporated by reference in their entireties:
1. Dean, K. M. & Palmer, A. E. Advances in fluorescence labeling strategies for dynamic cellular imaging. Nat. Chem. Biol. 10, 512-523 (2014).
2. Valm, A. M. et al. Applying systems-level spectral imaging and analysis to reveal the organelle interactome. Nature 546, 162-167 (2017).
3. Niehorster, T. et al. Multi-target spectrally resolved fluorescence lifetime imaging microscopy. Nat. Methods 13, 257-262 (2016).
4. Krutzik, P. O. & Nolan, G. P. Fluorescent cell barcoding in flow cytometry allows high-throughput drug screening and signaling profiling. Nat. Methods 3, 361-368 (2006).
5. Lu, J. et al. MicroRNA expression profiles classify human cancers. Nature 435, 834-838 (2005).
6. Li, Y., Cu, Y. T. H. & Luo, D. Multiplexed detection of pathogen DNA with DNA-based fluorescence nanobarcodes. Nat. Biotechnol. 23, 885-889 (2005).
7. Leng, Y., Sun, K., Chen, X. & Li, W. Suspension arrays based on nanoparticle-encoded microspheres for high-throughput multiplexed detection. Chem. Soc. Rev. 44, 5552-5595 (2015).
8. Zijlstra, P., Chon, J. W. & Gu, M. Five-dimensional optical recording mediated by surface plasmons in gold nanorods. Nature 45 9, 410-413 (2009).
9. Lu, Y. et al. Tunable lifetime multiplexing using luminescent nanocrystals. Nat. Photonics 8, 32-36 (2014).
10. Nguyen, H. Q. et al. Programmable microfluidic synthesis of over one thousand uniquely identifiable spectral codes. Adv. Opt. Mater. 5, 1600548 (2017).
11. Fournier-Bidoz, S. et al. Facile and rapid one-step mass preparation of quantum-dot barcodes. Angew. Chem. Int. Ed. Engl. 47, 5577-5581 (2008).
12. Han, M., Gao, X., Su, J. Z. & Nie, S. Quantum-dot-tagged microbeads for multiplexed optical coding of biomolecules. Nat. Biotechnol. 19, 631-635 (2001).
13. Cao, Y. C., Jin, R. & Mirkin, C. A. Nanoparticles with Raman spectroscopic fingerprints for DNA and RNA detection. Science 297, 1536-1540 (2002).
14. Jin, R., Cao, Y. C., Thaxton, C. S. & Mirkin, C. A. Glass-bead-based parallel detection of DNA using composite Raman labels. Small 2, 375-380 (2006).
15. Casari, C. S., Tommasini, M., Tykwinski, R. R. & Milani, A. Polyynes: 1-D systems with tunable properties. Nanoscale 8, 4414-4435 (2016).
16. Hirsch, A. The era of carbon allotropes. Nat. Mater. 9, 868-871 (2010).
17. Liu, M., Artyukhov, V. I., Lee, H., Xu, F. & Yakobson, B. I. Carbyne from first principles: chain of C atoms, a nanorod or a nanorope. ACS Nano 7, 10075-10082 (2013).
18. Chalifoux, W. A. & Tykwinski, R. R. Synthesis of polyynes to model the sp-carbon allotrope carbyne. Nat. Chem. 2, 967-971 (2010).
19. Luu, T. et al. Synthesis, structure, and nonlinear optical properties of diarylpolyynes. Org. Lett. 7, 51-54 (2005).
20. Milani, A., Tommasini, M., Del Zoppo, M., Castiglioni, C. & Zerbi, G. Carbon nanowires: phonon and pi-electron confinement. Phys. Rev. B 74, 153418 (2006).
21. Lucotti, A. et al. Absolute Raman intensity measurements and determination of the vibrational second hyperpolarizability of adamantyl endcapped polyynes. J. Raman Spectrosc. 43, 1293-1298 (2012).
22. Yamakoshi, H. et al. Alkyne-tag Raman imaging for visualization of mobile small molecules in live cells. J. Am. Chem. Soc. 134, 20681-20689 (2012).
23. Chen, Z. et al. Multicolor live-cell chemical imaging by isotopically edited alkyne vibrational palette. J. Am. Chem. Soc. 136, 8027-8033 (2014).
24. Liu, Z. et al. Multiplexed multicolor Raman imaging of live cells with isotopically modified single walled carbon nanotubes. J. Am. Chem. Soc. 13 0, 13540-13541 (2008).
25. Lucotti, A. et al. Evidence for solution-state nonlinearity of sp-carbon chains based on IR and Raman spectroscopy: violation of mutual exclusion. J. Am. Chem. Soc. 131, 4239-4244 (2009).

26. Wei, L. et al. Super-multiplex vibrational imaging. Nature 544, 465-470 (2017).
27. Freudiger, C. W. et al. Label-free biomedical imaging with high sensitivity by stimulated Raman scattering microscopy. Science 322, 1857-1861 (2008).
28. Wei, L. et al. Live-cell imaging of alkyne-tagged small biomolecules by stimulated Raman scattering. Nat. Methods 11, 410-412 (2014).
29. Yamakoshi, H. et al. A sensitive and specific Raman probe based on bisarylbutadiyne for live cell imaging of mitochondria. Bioorg. Med. Chem. Lett. 25, 664-667 (2015).
30. Wilson, R., Cossins, A. R. & Spiller, D. G. Encoded microcarriers for high-throughput multiplexed detection. Angew. Chem. Int. Ed. Engl. 45, 6104-6117 (2006).
31. Lee, J. H., Gomez, I. J., Sitterle, V. B. & Meredith, J. C. Dye-labeled polystyrene latex microspheres prepared via a combined swelling-diffusion technique. J. Colloid Interface Sci. 363, 137-144 (2011).
32. Humar, M. & Yun, S. H. Intracellular microlasers. Nat. Photonics 9, 572-576 (2015).
33. Agarwal, N. R. et al. Structure and chain polarization of long polyynes investigated with infrared and Raman spectroscopy. J. Raman Spectrosc. 44, 1398-1410 (2013).
34. Ozeki, Y. et al. High-speed molecular spectral imaging of tissue with stimulated Raman scattering. Nat. Photonics 6, 845-851 (2012).
35. Liao, C. S. et al. Microsecond scale vibrational spectroscopic imaging by multiplex stimulated Raman scattering microscopy. Light Sci. Appl. 4, e265 (2015).
36. Zhang, C. et al. Stimulated Raman scattering flow cytometry for label-free single-particle analysis. Optica 4, 103-109 (2017).
37. Choi H M, Beck V A, Pierce N A. Next-generation in situ hybridization chain reaction: higher gain, lower cost, greater durability. ACS Nano. 27, 4284-94 (2014).
38. Lin R, Feng Q, Li P, Zhou P, Wang R, Liu Z, Wang Z, Qi X, Tang N, Shao F, Luo M. A hybridization-chain-reaction-based method for amplifying immunosignals. Nat Methods. 15, 275-278 (2018).

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A library comprising between 2 and about 200 polyynes, comprising polyynes having structures chosen from the following formulae:

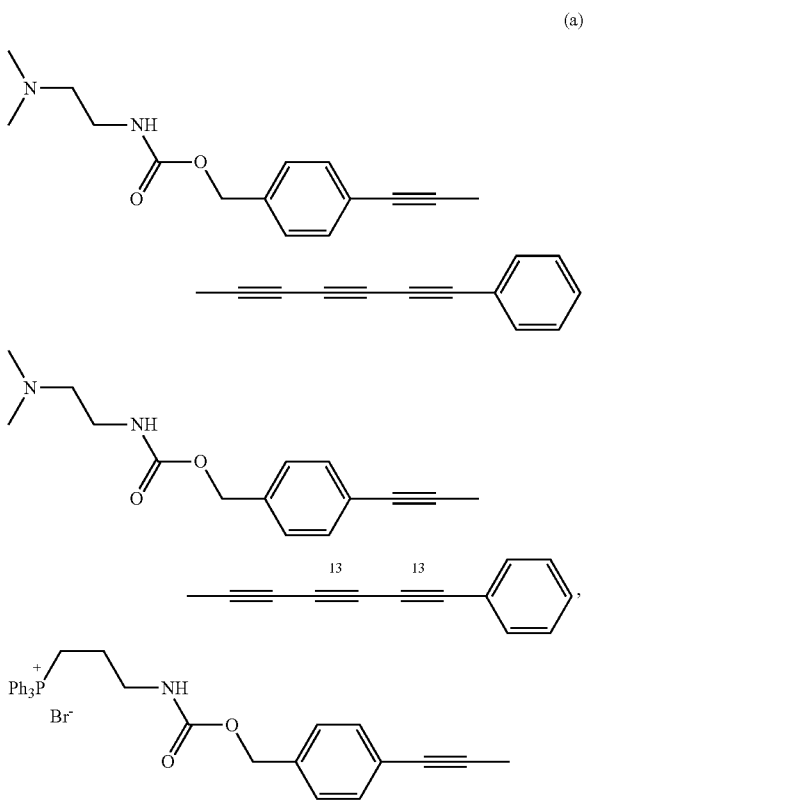

-continued
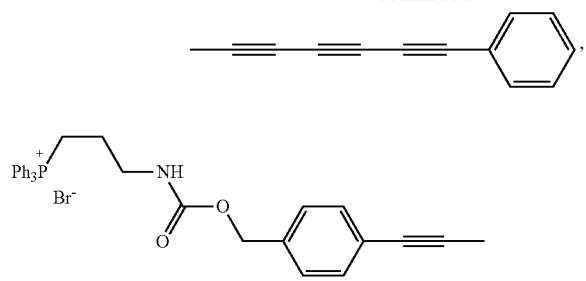
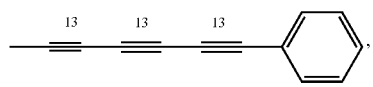
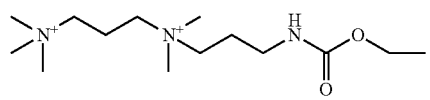
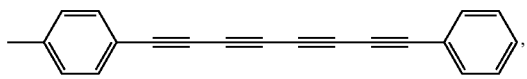
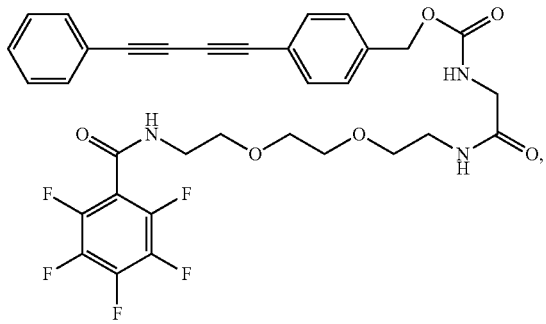
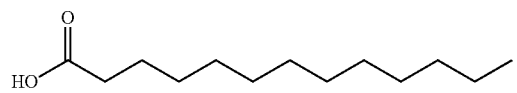
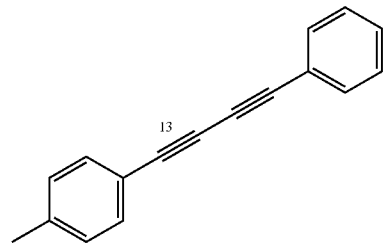
; and/or
(b)
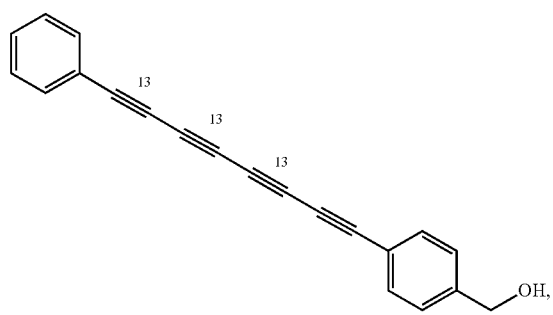

-continued
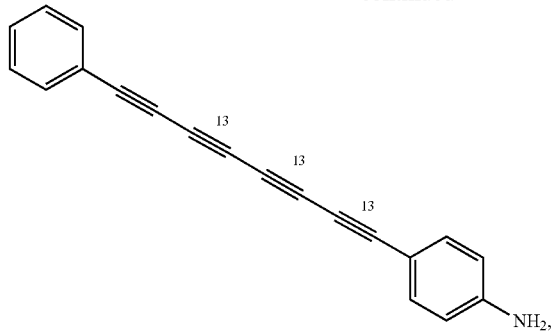
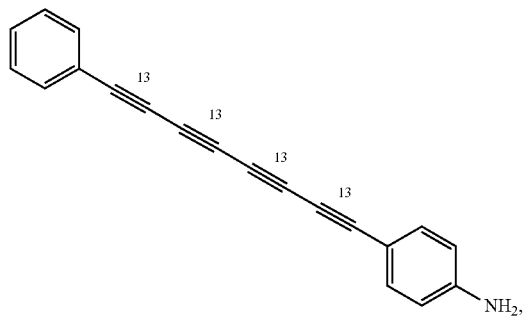
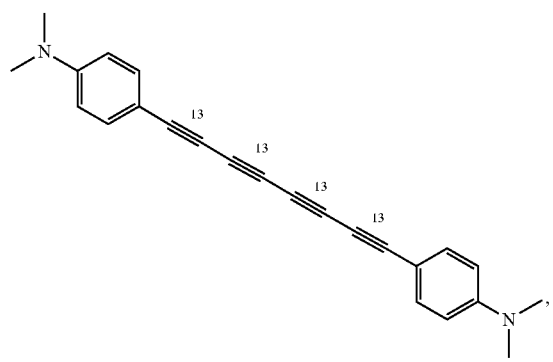
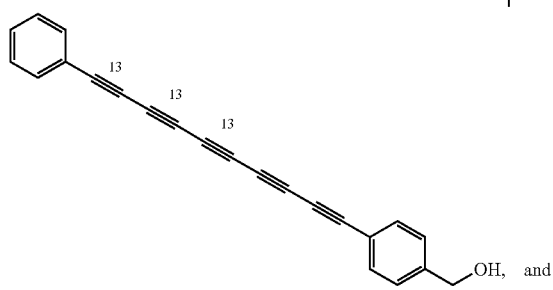
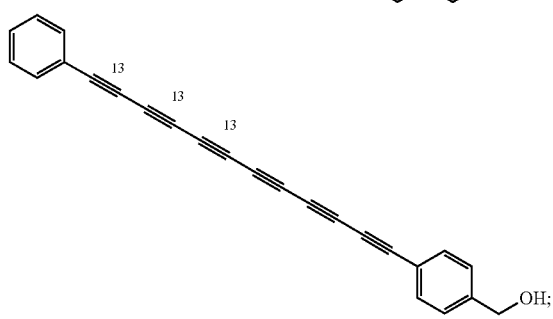
wherein each polyyne of the library is isotope enriched at the atoms specified and optionally conjugated to a solid support.

2. The library of claim 1, wherein the polyynes, have structures chosen from the following formulae:
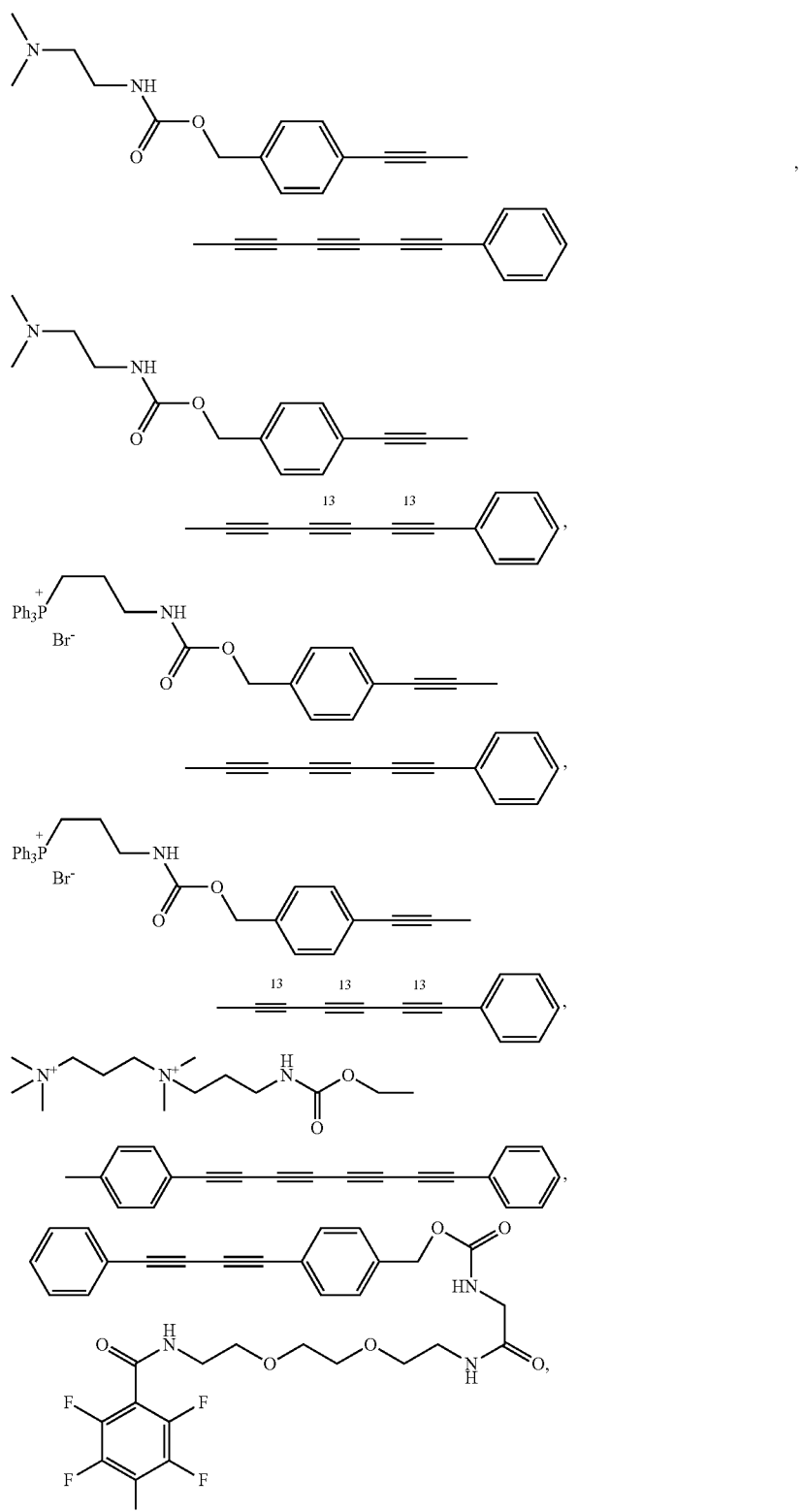
and

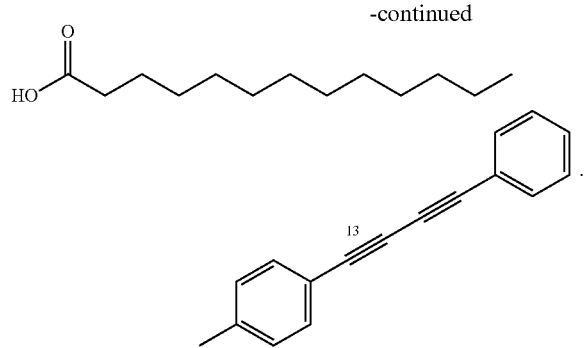

3. The library of claim 1, wherein the polyynes, independently, have structures chosen from the following formulae:

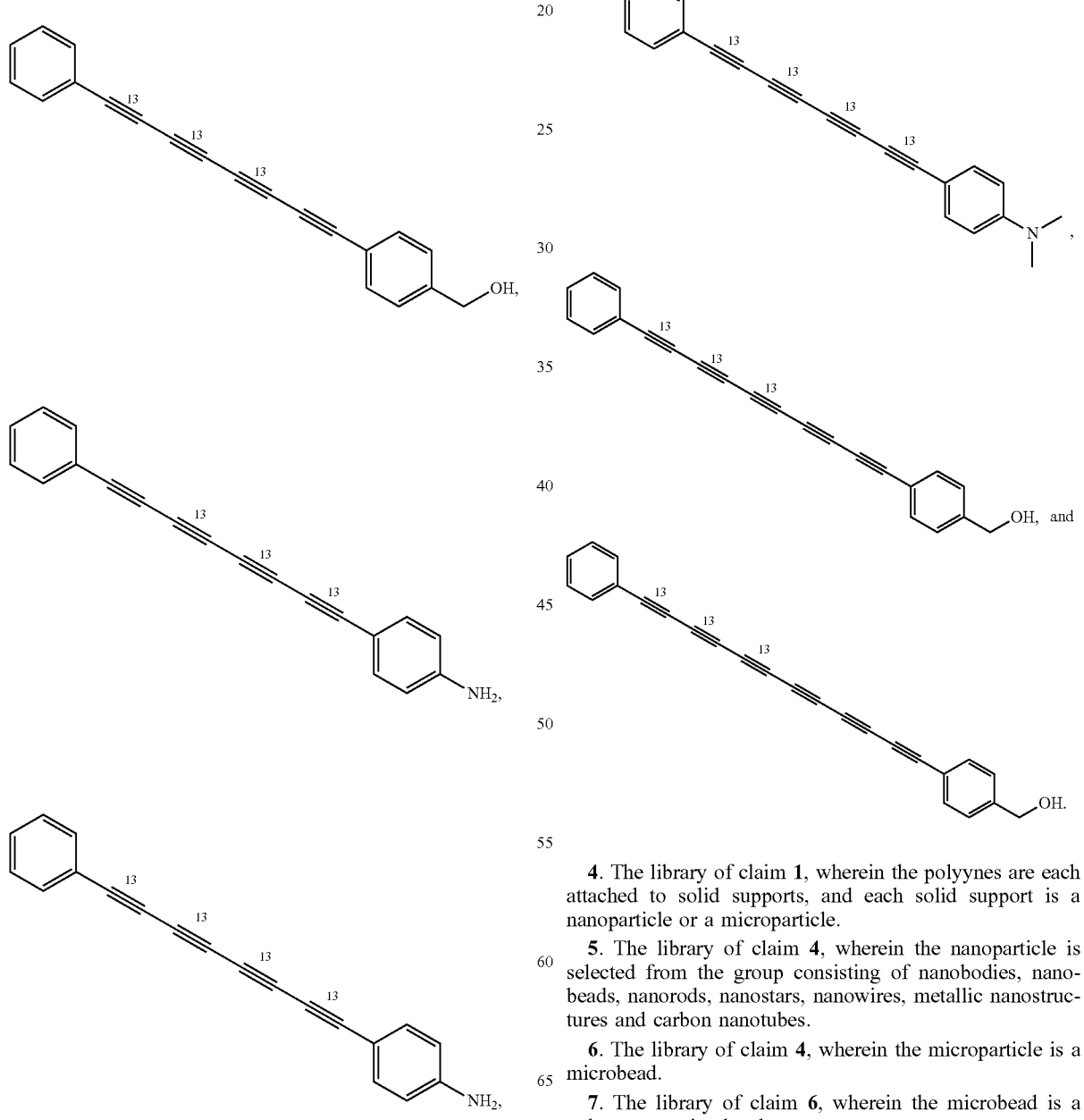

4. The library of claim 1, wherein the polyynes are each attached to solid supports, and each solid support is a nanoparticle or a microparticle.

5. The library of claim 4, wherein the nanoparticle is selected from the group consisting of nanobodies, nanobeads, nanorods, nanostars, nanowires, metallic nanostructures and carbon nanotubes.

6. The library of claim 4, wherein the microparticle is a microbead.

7. The library of claim 6, wherein the microbead is a polystyrene microbead.

8. The library of claim 4, wherein the nanoparticle or microparticle is conjugated to one or fluorescent labels, antigens, antibodies, antibody fragments, antibody mimetics, peptides, proteins, nucleic acids, lipids, carbohydrates, biotin, streptavidin, avidin, anti-biotin, folate, folate-binding protein, IgG, Protein A, Protein G, Protein L, a carbohydrate, lectin, lipid, or nucleic acids.

9. The library of claim 8, wherein the antibodies specifically bind to a stem cell, cancer cell, immune cell, neuron, glia cell, bacteria, fungi, or a virus.

10. The library of claim 1 wherein the nanoparticle or microparticle is formed of a polymer, and two or more polyynes are encapsulated within the polymeric nanoparticle or microparticle.

11. The library of claim 1, wherein the nanoparticle has a diameter between about 2 and about 100 nm, and the microparticle has a diameter greater than about 100 nm and less than about 100 μm.

12. The library of claim 11, wherein the nanoparticle has a diameter between about 5 and about 20 nm.

* * * * *